US010550054B2

(12) United States Patent
Bonnet et al.

(10) Patent No.: US 10,550,054 B2
(45) Date of Patent: *Feb. 4, 2020

(54) COMPOSITION COMPRISING HF AND 3,3,3-TRIFLUOROPROPENE

(71) Applicant: ARKEMA FRANCE, Colombes (FR)

(72) Inventors: Philippe Bonnet, Lyons (FR); Bertrand Collier, Saint-genis-laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 81 days.

This patent is subject to a terminal disclaimer.

(21) Appl. No.: 14/773,645

(22) PCT Filed: Feb. 24, 2014

(86) PCT No.: PCT/FR2014/050371
§ 371 (c)(1),
(2) Date: Sep. 8, 2015

(87) PCT Pub. No.: WO2014/147314
PCT Pub. Date: Sep. 25, 2014

(65) Prior Publication Data
US 2016/0046548 A1    Feb. 18, 2016

(30) Foreign Application Priority Data

Mar. 20, 2013 (FR) .................................. 13 52486

(51) Int. Cl.
*C01B 7/19* (2006.01)
*C07C 21/18* (2006.01)
*C09K 5/04* (2006.01)
*C09K 3/30* (2006.01)

(52) U.S. Cl.
CPC .............. *C07C 21/18* (2013.01); *C01B 7/191* (2013.01); *C09K 3/30* (2013.01); *C09K 5/045* (2013.01)

(58) Field of Classification Search
None
See application file for complete search history.

(56) References Cited

U.S. PATENT DOCUMENTS

| 6,013,846 | A  | * | 1/2000  | Wismer | ................... C07C 17/00 570/164 |
| 6,328,907 | B1 |   | 12/2001 | Nakada et al. | |
| 7,183,448 | B2 |   | 2/2007  | Nakada et al. | |
| 7,423,188 | B2 |   | 9/2008  | Miller et al. | |
| 8,075,797 | B2 |   | 12/2011 | Hulse et al. | |
| 8,273,928 | B2 | * | 9/2012  | Knapp | ................... C07C 17/25 570/134 |
| 8,378,158 | B2 |   | 2/2013  | Hulse et al. | |
| 8,450,537 | B2 | * | 5/2013  | Rao | ........................ C07C 17/10 570/156 |
| 8,858,823 | B2 |   | 10/2014 | Rached et al. | |
| 9,000,238 | B2 | * | 4/2015  | Knapp | ................... C07C 17/25 203/67 |
| 9,889,416 | B2 |   | 2/2018  | Bonnet et al. | |
| 10,029,961 | B2 |  | 7/2018  | Deur-Bert et al. | |
| 10,029,963 | B2 |  | 7/2018  | Bonnet et al. | |
| 10,077,221 | B2 |  | 9/2018  | Bonnet et al. | |
| 10,252,913 | B2 |  | 4/2019  | Bonnet et al. | |
| 10,266,465 | B2 |  | 4/2019  | Bonnet et al. | |
| 10,343,963 | B2 |  | 7/2019  | Bonnet et al. | |
| 2007/0100173 | A1 | * | 5/2007 | Miller | ..................... C01B 7/191 570/178 |
| 2007/0100175 | A1 | * | 5/2007 | Miller | ..................... C01B 7/196 570/178 |
| 2008/0051612 | A1 | * | 2/2008 | Knapp | ..................... C07C 21/18 570/178 |
| 2009/0127496 | A1 | * | 5/2009 | Rao | ......................... B01J 27/125 252/67 |
| 2010/0072415 | A1 | * | 3/2010 | Rao | ......................... B01J 23/26 252/67 |

(Continued)

FOREIGN PATENT DOCUMENTS

JP    H11-279088 A    10/1999
JP    2012-516336 A    7/2012

(Continued)

OTHER PUBLICATIONS

U.S. Appl. No. 15/104,836, Dominique Deur-Bert, filed Jun. 15, 2016.
Deur-Bert, Dominique, U.S. Appl. No. 15/104,836 entitled "Azeotropic Compositions of Hydrogen Flouride and Z-3,3,3-Trifluoro-1-Chloropropene,", filed Jun. 15, 2016.
International Search Report (PCT/ISA/210) dated Jun. 10, 2014, by the France Patent Office as the International Searching Authority for International Application No. PCT/FR2014/050371.
U.S. Appl. No. 16/018,191 Dominique Deur-Bert, Anne Pigamo and Phillipe Bonnet, filed Jun. 26, 2018.
Duer-Bert, Dominique, U.S. Appl. No. 16/018,191 entitled "Azeotropic Compositions of Hydrogen Flouride and Z-3,3,3-Trifluoro-1-Chloropropene," filed Jun. 26, 2018.
U.S. Appl. No. 15/858,005, Phillippe Bonnet, Bertrand Collier, Dominique Deur-Bert and Laurent Wendlinger, filed Dec. 29, 2017. (Cited herein as U.S. Pat. No. 2018/0126348 A1 of May 10, 2018).

Primary Examiner — Joseph D Anthony
(74) Attorney, Agent, or Firm — Buchanan Ingersoll & Rooney P.C.

(57) ABSTRACT

An azeotropic or quasi-azeotropic composition including hydrogen fluoride, 3,3,3-trifluoropropene and one or more (hydro)halogen-carbon compounds including between 1 and 3 carbon atoms. Also, a preferred azeotropic or quasi-azeotropic composition including hydrogen fluoride, 3,3,3-trifluoropropene, and one or more compounds selected from among 1,1,1,2,2-pentafluoropropane, 2,3,3,3-tetrafluoropropene, 1,3,3,3-tetrafluoropropene, 3,3,3-trifluoro-2-chloropropene, E-3,3,3-trifluoro-l-chloropropene, trifluoropropyne, 1,1,1,3,3-pentafluoropropane, 1,1,1,3,3-pentafluoropropane, 1,1,1,3,3-pentafluoropropene, 1,1,1,2,3-pentafluoropropene and 2-chloro, 1,1,1,2-tetrafluoropropane.

16 Claims, No Drawings

(56) References Cited

U.S. PATENT DOCUMENTS

| | | | |
|---|---|---|---|
| 2010/0187088 A1* | 7/2010 | Merkel | B01D 3/36 203/50 |
| 2010/0237279 A1* | 9/2010 | Hulse | C07C 17/206 252/182.12 |
| 2011/0112340 A1* | 5/2011 | Smith | C07C 17/04 570/169 |
| 2011/0218369 A1* | 9/2011 | Elsheikh | C07C 17/206 570/151 |
| 2011/0218370 A1 | 9/2011 | Elsheikh et al. | |
| 2012/0010449 A1 | 1/2012 | Wismer et al. | |
| 2012/0041239 A1* | 2/2012 | Suzuki | C07C 17/206 570/160 |
| 2012/0053369 A1* | 3/2012 | Hulse | C07C 17/206 570/135 |
| 2012/0053372 A1 | 3/2012 | Hulse et al. | |
| 2012/0056122 A1* | 3/2012 | Hulse | C01B 7/191 252/67 |
| 2012/0138841 A1* | 6/2012 | Hulse | A62D 1/0057 252/2 |
| 2012/0222448 A1* | 9/2012 | Chaki | C07C 17/383 62/617 |
| 2012/0305382 A1* | 12/2012 | Knapp | C07C 21/18 203/67 |
| 2013/0105296 A1* | 5/2013 | Chaki | C01B 7/196 203/60 |
| 2014/0012052 A1* | 1/2014 | Pham | C07C 17/38 570/160 |
| 2014/0024575 A1 | 1/2014 | Rached | |
| 2015/0105596 A1 | 4/2015 | Wang | |
| 2015/0197467 A1 | 7/2015 | Pigamo | |
| 2016/0009555 A1* | 1/2016 | Bonnet | C07C 21/18 252/182.12 |
| 2016/0023176 A1* | 1/2016 | Bonnet | C01B 7/191 51/307 |
| 2016/0023974 A1* | 1/2016 | Bonnet | C07C 21/18 252/182.12 |
| 2016/0031773 A1* | 2/2016 | Bonnet | C01B 7/195 252/182.12 |
| 2016/0046548 A1* | 2/2016 | Bonnet | C01B 7/19 252/182.12 |
| 2017/0297982 A1 | 10/2017 | Deur-Bert et al. | |
| 2018/0126348 A1 | 5/2018 | Bonnet et al. | |
| 2018/0297919 A1 | 10/2018 | Deur-Bert et al. | |
| 2018/0312453 A1 | 11/2018 | Bonnet et al. | |
| 2018/0354875 A1 | 12/2018 | Bonnet et al. | |

FOREIGN PATENT DOCUMENTS

| | | |
|---|---|---|
| JP | 2012-521430 A | 9/2012 |
| WO | WO 97/27163 A1 | 7/1997 |
| WO | WO 00/29361 A1 | 5/2000 |
| WO | WO 2007/053736 A2 | 5/2007 |
| WO | WO 2008/002500 A1 | 1/2008 |
| WO | WO 2009/105517 A2 | 8/2009 |
| WO | WO 2010/059493 A1 | 5/2010 |
| WO | WO 2010/088196 A2 | 8/2010 |
| WO | WO 2010/088196 A3 | 8/2010 |
| WO | WO 2010/111067 A1 | 9/2010 |
| WO | WO 2012/075283 A2 | 6/2012 |
| WO | WO 2014/147310 A1 | 9/2014 |
| WO | WO 2014/147311 A1 | 9/2014 |
| WO | WO 2014/147312 A1 | 9/2014 |
| WO | WO 2014/147313 A1 | 9/2014 |
| WO | WO 2014/147314 A1 | 9/2014 |

* cited by examiner

COMPOSITION COMPRISING HF AND 3,3,3-TRIFLUOROPROPENE

The present invention relates to azeotropic or quasi-azeotropic compositions comprising 3,3,3-trifluoropropene and hydrogen fluoride. These compositions may originate from intermediate compositions in the production of 3,3,3-trifluoropropene and are generally useful in processes for recycling hydrogen fluoride.

The manufacture of 3,3,3-trifluoropropene accompanied by a multitude of by-products, having a boiling point close to HFO-1243zf, leads to relatively complex and expensive purification steps. The difficulty encountered during the purification of HFO-1243zf generally implies an appreciable loss of desired product. Furthermore, these by-products may form azeotropic compositions with 1,3,3,3-tetrafluoropropene, making separation by distillation simple, very difficult, or even impossible.

Fluids based on 3,3,3-trifluoropropene have found numerous applications in varied industrial fields, especially as heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

The subject of the present invention is an azeotropic or quasi-azeotropic composition comprising hydrogen fluoride, 3,3,3-trifluoropropene and one or more (hydro)halocarbon compounds comprising between 1 and 3 carbon atoms. According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

The compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2=CF-CF_3$
HFC-245cb: 1,1,1,2,2-pentafluoropropane or $CF_3-CF_2-CH_3$
HFO-1234zeE: E-1,3,3,3-tetrafluoropropene or E-$CF_3-CH=CHF$
HFO-1234zeZ: Z-1,3,3,3-tetrafluoropropene or Z-$CF_3-CH=CHF$
HFO-1243zf: 3,3,3-trifluoropropene or $CF_3-CH=CH_2$
HCFO-1233xf: 3,3,3-trifluoro-2-chloropropene or $CF_3-CCl=CH_2$
HCFO-1233zdE: E-3,3,3-trifluoro-1-chloropropene or E-$CF_3-CH=CHCl$
HCFO-1233zdZ: Z-3,3,3-trifluoro-1-chloropropene or Z-$CF_3-CH=CHCl$
HFO-1225yeZ: Z-1,1,1,2,3-pentafluoropropene or Z-$CHF=CF-CF_3$
HFO-1225yeE: E-1,1,1,2,3-pentafluoropropene or E-$CHF=CF-CF_3$
HFO-1225zc: 1,1,3,3,3-pentafluoropropene or $CF_2=CH-CF_3$
HFO-1225yc: 1,1,2,3,3-pentafluoropropene or $CF_2=CF-CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F-CCl=CF_2$
HCFO-1233xe: 1,3,3-trifluoro-2-chloropropene or $CHF_2-CCl=CHF$
HCFO-1233yb: 1,2,3-trifluoro-1-chloropropene or $CH_2F-CF=CFCl$
HCFO-1233yc: 1,1,2-trifluoro-3-chloropropene or $CH_2Cl-CF=CF_2$
HCFO-1233yd: 2,3,3-trifluoro-1-chloropropene or $CHF_2-CF=CHCl$
HCFO-1233ye: 1,2,3-trifluoro-3-chloropropene or $CHClF-CF=CHF$
HCFO-1233yf: 2,3,3-trifluoro-3-chloropropene or $CClF_2-CF=CH_2$
HCFO-1233zb: 1,3,3-trifluoro-1-chloropropene or $CHF_2-CH=CFCl$
HCFO-1233zc: 1,1,3-trifluoro-3-chloropropene or $CHClF-CH=CF_2$
HCFO-1233ze: 1,3,3-trifluoro-3-chloropropene or $CClF_2-CH=CHF$
HFO-1234yc: 1,2,3-tetrafluoropropene or $CF_2=CF-CH_2F$
HFO-1234ye: 2,3,3-tetrafluoropropene or $CHF=CF-CHF_2$
HFO-1234zc: 1,3,3-tetrafluoropropene or $CF_2=CH-CHF_2$
HCFO-1242: chlorodifluoropropene, or $C_3H_3F_2Cl$
HFO-1243yc: 1,1,2-trifluoropropene or $CH_3-CF=CF_2$
HFO-1243ye: 1,2,3-trifluoropropene or $CH_2F-CF=CHF$
HFO-1243yf: 2,3,3-trifluoropropene or $CHF_2-CF=CH_2$
HFO-1243zc: 1,1,3-trifluoropropene or $CH_2F-CH=CF_2$ HFO-1243ze: 1,3,3-trifluoropropene or CHF$_2$—CH=CHF HCFO-1251: chlorofluoropropene, or C$_3$H$_4$FCl HFO-1252: difluoropropene, or C$_3$H$_4$F$_2$ HFO-216: hexafluoropropene, or C$_3$F$_6$Cl$_2$ HCFO-217: chloroheptafluoropropane, or C$_3$F$_7$Cl HFC-218: octafluoropropane, or C$_3$F$_8$ HCFC-225: dichloropentafluoropropane, or C$_3$HF$_5$Cl$_2$ HCFC-226: chlorohexafluoropropane, or C$_3$HF$_6$Cl HFC-227: heptafluoropropane, or C$_3$HF$_7$ HCFC-234: dichlorotetrafluoropropane, or C$_3$H$_2$F$_4$Cl$_2$ HCFC-235: chloropentafluoropropane, or C$_3$H$_2$F$_5$Cl HFC-236: hexafluoropropane, or C$_3$H$_2$F$_6$ HCFC-243: dichlorotrifluoropropane, or C$_3$H$_3$F$_3$Cl$_2$ HCFC-244: chlorotetrafluoropropane, or C$_3$H$_3$F$_4$Cl HCFC-244bb: 2-chloro-1,1,1,2-tetrafluoropropane or CF$_3$—CFCl—CH$_3$ HFC-245fa: 1,1,1,3,3-pentafluoropropane or CF$_3$—CH$_2$—CHF$_2$ HFC-245ea: 1,1,2,3,3-pentafluoropropane or CHF$_2$—CHF—CHF$_2$ HFC-245eb: 1,1,1,2,3-pentafluoropropane or CF$_3$—CHF—CH$_2$F HFC-245ca: 1,1,2,2,3-pentafluoropropane or CHF$_2$—CF$_2$—CH$_2$F HCFC-253: chlorotrifluoropropane, or C$_3$H$_4$F$_3$Cl HFC-254: tetrafluoropropane, or C$_3$H$_4$F$_4$ HCFC-262: chlorodifluoropropane, or C$_3$H$_5$F$_2$Cl HFC-263: trifluoropropane, or C$_3$H$_5$F$_3$ trifluoropropyne: CF$_3$—C≡CH The composition according to the invention may optionally be a mixture of one or more azeotropes and/or heteroazeotropes of ternary, quaternary, penternary systems, systems with six compounds, systems with seven compounds, systems with eight or more compounds.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,2,3,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,1,2-tetrafluoropropane, 1-chloro-1,1,2,3-tetrafluoropropane, 3-chloro-1,1,1,3-tetrafluoropropane, 1-chloro-1,1,3,3-tetrafluoropropane, pentafluoropropane, 1,1,2,2,3-pentafluoropropane, 1,1,2,3,3-pentafluoropropane, 1,1,1,2,3-pentafluoropropane, 1,1,1,3,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,3-trifluoropropane, 3-chloro-1,1,1-trifluoropropane, 1-chloro-1,3,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

A subject of the present invention is also an azeotropic or quasi-azeotropic composition comprising hydrogen fluoride, 3,3,3-trifluoropropene, and one or more compounds chosen from 1,1,1,2,2-pentafluoropropane, 2,3,3,3-tetrafluoropropene, E-3,3,3-trifluoro-1-chloropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also a composition comprising hydrogen fluoride, 3,3,3-trifluoropropene and at least one or more organic compounds chosen from E-1,3,3,3-tetrafluoropropene, Z-1,3,3,3-tetrafluoropropene, 3,3,3-trifluoro-2-chloropropene, E-3,3,3-trifluoro-1-chloropropene, 1,1,1,2,2-pentafluoropropane and 2,3,3,3-tetrafluoropropene.

According to one embodiment, the composition according to the invention comprises hydrogen fluoride, 3,3,3-trifluoropropene, 1,1,1,2,2-heptafluoropropane and optionally one or more compounds chosen from 2,3,3,3-tetrafluoropropene, E-3,3,3-trifluoro-1-chloropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, 2,3,3,3-tetrafluoropropene and optionally one or more compounds chosen from E-3,3,3-trifluoro-1-chloropropene, 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 3,3,3-trifluoropropene, E-3,3,3-trifluoro-1-chloropropene and optionally one or more compounds chosen from 3,3,3-trifluoro-2-chloropropene, 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, 3,3,3-trifluoro-2-chloropropene and optionally one or more compounds chosen from 1,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 3,3,3-trifluoropropene, 1,3,3,3-tetrafluoropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, trifluoropropyne and optionally one or more compounds chosen from 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 3,3,3-trifluoropropene, 1,1,1,3,3-pentafluoropropane and optionally one or more compounds chosen from 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, 1,1,1,3,3-pentafluoropropene and optionally one or more compounds chosen from 1,1,1,2,3-pentafluoropropene and 2-chloro-1,1,1,2-tetrafluoropropane.

According to one embodiment, the composition according to the invention comprises hydrogen fluoride, 3,3,3-trifluoropropene, 1,1,1,2,3-pentafluoropropene and optionally 2-chloro-1,1,1,2-tetrafluoropropane.

According to another embodiment, the composition according to the invention comprises hydrogen fluoride, 3,3,3-trifluoropropene and 2-chloro-1,1,1,2-tetrafluoropropane.

According to another embodiment, the composition according to the invention comprises hydrogen fluoride, 3,3,3-trifluoropropene, E-1,3,3,3-tetrafluoropropene and optionally one or more compounds chosen from Z-1,3,3,3-tetrafluoropropene, 3,3,3-trifluoro-2-chloropropene, E-3,3,3-trifluoro-1-chloropropene, 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment of the invention, the composition comprises hydrogen fluoride, 3,3,3-trifluoropropene, Z-1,3,3,3-tetrafluoropropene and optionally one or more compounds chosen from 3,3,3-trifluoro-2-chloropropene, E-3,3,3-trifluoro-1-chloropropene, 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, 3,3,3-trifluoro-2-chloropropene and optionally one or more compounds chosen from E-3,3,3-trifluoro-1-chloropropene, 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment of the invention, the composition comprises hydrogen fluoride, 3,3,3-trifluoropropene, E-3,3,3-trifluoro-1-chloropropene and optionally one or more compounds chosen from 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 3,3,3-trifluoropropene, 1,1,1,2,2-pentafluoropropane and optionally one or more compounds chosen from 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment of the invention, the composition comprises hydrogen fluoride, 3,3,3-trifluoropropene, 2,3,3,3-tetrafluoropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

Irrespective of the embodiment, the composition preferably comprises from 1% to 95% and advantageously from 5% to 80% by weight of hydrogen fluoride and from 99% to 5% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1243zf and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, 3,3,3-trifluoropropene and a compound chosen from 1,1,1,2,2-pentafluoropropane, 2,3,3,3-tetrafluoropropene, 3,3,3-trifluoro-2-chloropropene, 1,3,3,3-tetrafluoropropene and E-3,3,3-trifluoro-1-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, 3,3,3-trifluoropropene and a compound chosen from trifluoropropyne, 1,1,1,3,3-pentafluoropropane, 1,1,1,3,3-pentafluoropropene, Z-1,1,1,2,3-pentafluoropropene and 2-chloro-1,1,1,2-tetrafluoropropane are characterized by a phase depleted in HF and a phase enriched in HF for at least isotherms at 0° C., 25° C. and 40° C.

An azeotropic or quasi-azeotropic composition that is preferred according to the invention comprises from 1% to 85% by weight of hydrogen fluoride and from 99% to 15% by weight of the sum of HFO-1243zf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1243zf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 1% to 85% by weight of hydrogen fluoride and from 99% to 15% by weight of the sum of HFO-1243zf, of HCFC-244bb, of HFC-245fa, of trifluoropropyne, of HFO-1225yeZ and of HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 80% by weight of hydrogen fluoride and from 95% to 20% by weight of the sum of HFO-1243zf, of HCFC-244bb, of HFC-245fa, of trifluoropropyne, of HFO-1225yeZ and of HFO-1225zc, the boiling point of this preferred composition is between 0 and 40° C. at a pressure of between 0.7 and 18 bar absolute.

The pressure characteristics of the mixtures of Examples 1, 4, 7, 10, 13, 16 and 19 were calculated for an isotherm at 25° C.

Examples 2, 5, 8, 11, 14, 17 and 20 represent the boiling point and pressure ranges of the mixtures and Examples 3, 6, 9, 12, 15, 18 and 21 represent the decantation ranges of the mixtures of Examples 1, 4, 7, 10, 13, 16 and 19 as a function of the mass percentage of HF characterized for isotherms at 0° C., 25° C. and 40° C. The decantation ranges of Examples 3, 6, 9, 12, 15, 18 and 21 are calculated for mixtures of organic compounds having equal-mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at the liquid-vapor equilibrium, under azeotropic conditions.

EXAMPLE 1: TERNARY MIXTURES, ISOTHERM AT 25° C.

HF-HFO-1243zf-HFC-245cb    HF-HFO-1234yf-HFO-1243zf

| Organics 0.95 F1243zf + 0.05 F245cb | | Organics 0.5 F1243zf + 0.5 F245cb | | Organics 0.05 F1243zf + 0.95 F245cb | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 5.8 | 0 | 5.4 | 0 | 4.7 |
| 0.05 | 6.7 | 0.05 | 6.4 | 0.05 | 5.9 |
| 0.1 | 6.8 | 0.1 | 6.4 | 0.1 | 5.9 |
| 0.15 | 6.8 | 0.15 | 6.4 | 0.15 | 5.9 |
| 0.2 | 6.8 | 0.2 | 6.4 | 0.2 | 5.9 |
| 0.25 | 6.8 | 0.25 | 6.4 | 0.25 | 5.9 |
| 0.3 | 6.8 | 0.3 | 6.4 | 0.3 | 5.9 |
| 0.35 | 6.8 | 0.35 | 6.4 | 0.35 | 5.9 |
| 0.4 | 6.8 | 0.4 | 6.4 | 0.4 | 5.9 |
| 0.45 | 6.8 | 0.45 | 6.4 | 0.45 | 5.9 |
| 0.5 | 6.7 | 0.5 | 6.4 | 0.5 | 5.9 |
| 0.55 | 6.7 | 0.55 | 6.4 | 0.55 | 5.9 |
| 0.6 | 6.7 | 0.6 | 6.4 | 0.6 | 5.9 |
| 0.65 | 6.7 | 0.65 | 6.4 | 0.65 | 5.9 |
| 0.7 | 6.6 | 0.7 | 6.4 | 0.7 | 5.9 |
| 0.75 | 6.4 | 0.75 | 6.3 | 0.75 | 5.9 |
| 0.8 | 6.1 | 0.8 | 6.2 | 0.8 | 5.9 |
| 0.85 | 5.6 | 0.85 | 5.7 | 0.85 | 5.9 |
| 0.9 | 4.8 | 0.9 | 4.9 | 0.9 | 5.0 |
| 0.95 | 3.4 | 0.95 | 3.5 | 0.95 | 3.6 |
| 1 | 1.2 | 1 | 1.2 | 1 | 1.2 |

| Organics 0.95 F1243zf + 0.05 F1234yf | | Organics 0.5 F1243zf + 0.5 F1234yf | | Organics 0.05 F1243zf + 0.95 F1234yf | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 5.9 | 0 | 6.3 | 0 | 6.7 |
| 0.05 | 6.8 | 0.05 | 7.2 | 0.05 | 7.7 |
| 0.1 | 6.9 | 0.1 | 7.3 | 0.1 | 7.7 |
| 0.15 | 6.9 | 0.15 | 7.3 | 0.15 | 7.7 |
| 0.2 | 6.8 | 0.2 | 7.2 | 0.2 | 7.7 |
| 0.25 | 6.8 | 0.25 | 7.2 | 0.25 | 7.7 |
| 0.3 | 6.8 | 0.3 | 7.2 | 0.3 | 7.7 |
| 0.35 | 6.8 | 0.35 | 7.2 | 0.35 | 7.7 |
| 0.4 | 6.8 | 0.4 | 7.2 | 0.4 | 7.7 |
| 0.45 | 6.8 | 0.45 | 7.2 | 0.45 | 7.7 |
| 0.5 | 6.8 | 0.5 | 7.2 | 0.5 | 7.7 |
| 0.55 | 6.8 | 0.55 | 7.2 | 0.55 | 7.7 |
| 0.6 | 6.8 | 0.6 | 7.2 | 0.6 | 7.7 |
| 0.65 | 6.7 | 0.65 | 7.2 | 0.65 | 7.7 |
| 0.7 | 6.6 | 0.7 | 7.1 | 0.7 | 7.7 |
| 0.75 | 6.5 | 0.75 | 7.0 | 0.75 | 7.5 |
| 0.8 | 6.2 | 0.8 | 6.7 | 0.8 | 7.2 |
| 0.85 | 5.7 | 0.85 | 6.1 | 0.85 | 6.6 |
| 0.9 | 4.8 | 0.9 | 5.2 | 0.9 | 5.6 |
| 0.95 | 3.4 | 0.95 | 3.6 | 0.95 | 3.8 |
| 1 | 1.2 | 1 | 1.2 | 1 | 1.2 |

HF-HCFO-1233xf-HFO-1243zf    HF-HCFO-1233zdE-HFO-1243zf

| Organics 0.95 F1243zf + 0.05 F1233xf | | Organics 0.5 F1243zf + 0.5 F1233xf | | Organics 0.05 F1243zf + 0.95 F1233xf | |
|---|---|---|---|---|---|
| MASS-FRAC HF | TOTAL PRES bar | MASS-FRAC HF | TOTAL PRES bar | MASS-FRAC HF | TOTAL PRES bar |
| 0 | 5.7 | 0 | 4.0 | 0 | 1.8 |
| 0.05 | 6.6 | 0.05 | 5.0 | 0.05 | 2.9 |
| 0.1 | 6.7 | 0.1 | 5.0 | 0.1 | 2.9 |
| 0.15 | 6.6 | 0.15 | 5.0 | 0.15 | 2.9 |
| 0.2 | 6.6 | 0.2 | 5.0 | 0.2 | 2.9 |
| 0.25 | 6.6 | 0.25 | 5.0 | 0.25 | 2.9 |
| 0.3 | 6.6 | 0.3 | 5.0 | 0.3 | 2.9 |
| 0.35 | 6.6 | 0.35 | 5.0 | 0.35 | 2.9 |
| 0.4 | 6.6 | 0.4 | 5.0 | 0.4 | 2.9 |
| 0.45 | 6.6 | 0.45 | 5.0 | 0.45 | 2.9 |
| 0.5 | 6.6 | 0.5 | 5.0 | 0.5 | 2.9 |
| 0.55 | 6.6 | 0.55 | 5.0 | 0.55 | 2.9 |
| 0.6 | 6.6 | 0.6 | 5.0 | 0.6 | 2.9 |
| 0.65 | 6.5 | 0.65 | 4.9 | 0.65 | 2.9 |
| 0.7 | 6.4 | 0.7 | 4.9 | 0.7 | 2.9 |
| 0.75 | 6.3 | 0.75 | 4.7 | 0.75 | 2.9 |
| 0.8 | 6.0 | 0.8 | 4.5 | 0.8 | 2.7 |
| 0.85 | 5.5 | 0.85 | 4.1 | 0.85 | 2.5 |
| 0.9 | 4.7 | 0.9 | 3.5 | 0.9 | 2.2 |
| 0.95 | 3.3 | 0.95 | 2.6 | 0.95 | 1.8 |
| 1 | 1.2 | 1 | 1.2 | 1 | 1.2 |

| Organics 0.95 F1243zf + 0.05 F1233zdE | | Organics 0.5 F1243zf + 0.5 F1233zdE | | Organics 0.05 F1243zf + 0.95 F1233zdE | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 5.7 | 0 | 3.9 | 0 | 1.6 |
| 0.05 | 6.6 | 0.05 | 5.0 | 0.05 | 2.7 |
| 0.1 | 6.6 | 0.1 | 4.9 | 0.1 | 2.7 |
| 0.15 | 6.6 | 0.15 | 4.9 | 0.15 | 2.7 |
| 0.2 | 6.6 | 0.2 | 4.9 | 0.2 | 2.7 |
| 0.25 | 6.6 | 0.25 | 4.9 | 0.25 | 2.7 |
| 0.3 | 6.6 | 0.3 | 4.9 | 0.3 | 2.7 |
| 0.35 | 6.6 | 0.35 | 4.9 | 0.35 | 2.7 |
| 0.4 | 6.6 | 0.4 | 4.9 | 0.4 | 2.7 |
| 0.45 | 6.6 | 0.45 | 4.9 | 0.45 | 2.7 |
| 0.5 | 6.6 | 0.5 | 4.9 | 0.5 | 2.7 |
| 0.55 | 6.6 | 0.55 | 4.9 | 0.55 | 2.7 |
| 0.6 | 6.6 | 0.6 | 4.9 | 0.6 | 2.7 |
| 0.65 | 6.5 | 0.65 | 4.8 | 0.65 | 2.7 |
| 0.7 | 6.4 | 0.7 | 4.8 | 0.7 | 2.7 |
| 0.75 | 6.3 | 0.75 | 4.6 | 0.75 | 2.7 |
| 0.8 | 6.0 | 0.8 | 4.4 | 0.8 | 2.5 |
| 0.85 | 5.5 | 0.85 | 4.0 | 0.85 | 2.4 |
| 0.9 | 4.6 | 0.9 | 3.4 | 0.9 | 2.1 |
| 0.95 | 3.3 | 0.95 | 2.5 | 0.95 | 1.7 |
| 1 | 1.2 | 1 | 1.2 | 1 | 1.2 |

HF-HFO-1234zeE-HFO-1243zf    HF-HFO-1234zeZ-HFO-1243zf

| Organics 0.95 F1243zf + 0.05 F1234zeE | | Organics 0.5 F1243zf + 0.5 F1234zeE | | Organics 0.05 F1243zf + 0.95 F1234zeE | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 5.8 | 0 | 5.4 | 0 | 4.9 |
| 0.05 | 6.7 | 0.05 | 6.3 | 0.05 | 5.9 |
| 0.1 | 6.8 | 0.1 | 6.4 | 0.1 | 5.9 |
| 0.15 | 6.8 | 0.15 | 6.4 | 0.15 | 5.9 |
| 0.2 | 6.8 | 0.2 | 6.4 | 0.2 | 5.9 |
| 0.25 | 6.8 | 0.25 | 6.4 | 0.25 | 5.9 |
| 0.3 | 6.8 | 0.3 | 6.4 | 0.3 | 5.9 |
| 0.35 | 6.8 | 0.35 | 6.4 | 0.35 | 5.9 |
| 0.4 | 6.7 | 0.4 | 6.4 | 0.4 | 5.9 |
| 0.45 | 6.7 | 0.45 | 6.4 | 0.45 | 5.9 |
| 0.5 | 6.7 | 0.5 | 6.3 | 0.5 | 5.8 |
| 0.55 | 6.7 | 0.55 | 6.3 | 0.55 | 5.8 |
| 0.6 | 6.7 | 0.6 | 6.3 | 0.6 | 5.7 |
| 0.65 | 6.6 | 0.65 | 6.2 | 0.65 | 5.6 |
| 0.7 | 6.5 | 0.7 | 6.1 | 0.7 | 5.5 |
| 0.75 | 6.4 | 0.75 | 5.8 | 0.75 | 5.2 |
| 0.8 | 6.1 | 0.8 | 5.5 | 0.8 | 4.9 |
| 0.85 | 5.6 | 0.85 | 5.0 | 0.85 | 4.4 |
| 0.9 | 4.7 | 0.9 | 4.2 | 0.9 | 3.6 |
| 0.95 | 3.4 | 0.95 | 3.0 | 0.95 | 2.6 |
| 1 | 1.2 | 1 | 1.2 | 1 | 1.2 |

| Organics 0.95 F1243zf + 0.05 F1234zeZ | | Organics 0.5 F1243zf + 0.5 F1234zeZ | | Organics 0.05 F1243zf + 0.95 F1234zeZ | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 5.7 | 0 | 4.0 | 0 | 2.0 |
| 0.05 | 6.6 | 0.05 | 5.0 | 0.05 | 3.1 |
| 0.1 | 6.6 | 0.1 | 5.0 | 0.1 | 3.1 |
| 0.15 | 6.6 | 0.15 | 5.0 | 0.15 | 3.1 |
| 0.2 | 6.6 | 0.2 | 5.0 | 0.2 | 3.1 |
| 0.25 | 6.6 | 0.25 | 5.0 | 0.25 | 3.1 |
| 0.3 | 6.6 | 0.3 | 5.0 | 0.3 | 3.1 |
| 0.35 | 6.6 | 0.35 | 5.0 | 0.35 | 3.1 |
| 0.4 | 6.6 | 0.4 | 5.0 | 0.4 | 3.1 |
| 0.45 | 6.6 | 0.45 | 5.0 | 0.45 | 3.1 |
| 0.5 | 6.6 | 0.5 | 5.0 | 0.5 | 3.1 |
| 0.55 | 6.6 | 0.55 | 5.0 | 0.55 | 3.1 |
| 0.6 | 6.6 | 0.6 | 5.0 | 0.6 | 3.1 |
| 0.65 | 6.5 | 0.65 | 5.0 | 0.65 | 3.1 |
| 0.7 | 6.4 | 0.7 | 4.9 | 0.7 | 3.1 |
| 0.75 | 6.3 | 0.75 | 4.8 | 0.75 | 3.1 |
| 0.8 | 6.0 | 0.8 | 4.5 | 0.8 | 3.0 |
| 0.85 | 5.5 | 0.85 | 4.2 | 0.85 | 2.8 |
| 0.9 | 4.7 | 0.9 | 3.6 | 0.9 | 2.4 |
| 0.95 | 3.3 | 0.95 | 2.6 | 0.95 | 1.9 |
| 1 | 1.2 | 1 | 1.2 | 1 | 1.2 |

EXAMPLE 2: TEMPERATURE AND PRESSURE RANGE OF TERNARY MIXTURES

| | Boiling point range | |
|---|---|---|
| Ternary | Temperature ° C. | Pressure bar abs |
| HF-HFO-1243zf-HFC-245cb | 0 to 40 | ~2.5 to ~10.4 |
| HF-HFO-1234yf-HFO-1243zf | 0 to 40 | ~3.0 to ~11.7 |
| HF-HCFO-1233xf-HFO-1243zf | 0 to 40 | ~1.1 to ~10.2 |
| HF-HFO-1234zeE-HFO-1243zf | 0 to 40 | ~2.5 to ~10.4 |
| HF-HFO-1234zeZ-HFO-1243zf | 0 to 40 | ~1.2 to ~10.2 |
| HF-HCFO-1233zdE-HFO-1243zf | 0 to 40 | ~1.1 to ~10.2 |

EXAMPLE 3: DECANTATION RANGE OF TERNARY MIXTURES

| | Decantation ranges Mass percentage of HF | | |
|---|---|---|---|
| Ternary | Isotherm 0° C. | Isotherm 25° C. | Isotherm 40° C. |
| HF-HFO-1243zf-HFC-245cb | 5-75 | 10-75 | 40-70 |
| HF-HFO-1234yf-HFO-1243zf | 5-70 | * | * |
| HF-HCFO-1233xf-HFO-1243zf | 5-75 | 10-65 | 20-40 |
| HF-HFO-1234zeE-HFO-1243zf | 5-65 | * | * |
| HF-HFO-1234zeZ-HFO-1243zf | 5-75 | 10-65 | * |
| HF-HCFO-1233zdE-HFO-1243zf | 5-75 | 5-65 | 15-45 |

EXAMPLE 4: QUATERNARY MIXTURES, ISOTHERM AT 25° C.

HF-HCFO-1233xf-HFO-1243zf-HFC-245cb

| Organics 0.9 F1233xf + 0.05 F1243zf + 0.05 F245cb | | Organics 0.4 F1233xf + 0.3 F1243zf + 0.3 F245cb | | Organics 0.05 F1233xf + 0.9 F1243zf + 0.05 F245cb | | Organics 0.05 F1233xf + 0.05 F1243zf + 0.9 F245cb | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 2.0 | 0 | 4.0 | 0 | 5.6 | 0 | 4.6 |
| 0.05 | 3.1 | 0.05 | 5.1 | 0.05 | 6.6 | 0.05 | 5.7 |
| 0.1 | 3.1 | 0.1 | 5.1 | 0.1 | 6.6 | 0.1 | 5.7 |
| 0.15 | 3.1 | 0.15 | 5.1 | 0.15 | 6.6 | 0.15 | 5.7 |
| 0.2 | 3.1 | 0.2 | 5.1 | 0.2 | 6.6 | 0.2 | 5.7 |
| 0.25 | 3.1 | 0.25 | 5.1 | 0.25 | 6.6 | 0.25 | 5.7 |
| 0.3 | 3.1 | 0.3 | 5.1 | 0.3 | 6.6 | 0.3 | 5.7 |
| 0.35 | 3.1 | 0.35 | 5.1 | 0.35 | 6.6 | 0.35 | 5.7 |

-continued

| Organics 0.9 F1233xf + 0.05 F1243zf + 0.05 F245cb | | Organics 0.4 F1233xf + 0.3 F1243zf + 0.3 F245cb | | Organics 0.05 F1233xf + 0.9 F1243zf + 0.05 F245cb | | Organics 0.05 F1233xf + 0.05 F1243zf + 0.9 F245cb | |
|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0.4 | 3.1 | 0.4 | 5.1 | 0.4 | 6.6 | 0.4 | 5.8 |
| 0.45 | 3.1 | 0.45 | 5.1 | 0.45 | 6.6 | 0.45 | 5.8 |
| 0.5 | 3.1 | 0.5 | 5.1 | 0.5 | 6.6 | 0.5 | 5.8 |
| 0.55 | 3.1 | 0.55 | 5.1 | 0.55 | 6.6 | 0.55 | 6.8 |
| 0.6 | 3.1 | 0.6 | 5.1 | 0.6 | 6.5 | 0.6 | 5.8 |
| 0.65 | 3.1 | 0.65 | 5.1 | 0.65 | 6.5 | 0.65 | 5.8 |
| 0.7 | 3.1 | 0.7 | 5.1 | 0.7 | 6.4 | 0.7 | 5.8 |
| 0.75 | 3.1 | 0.75 | 5.1 | 0.75 | 6.3 | 0.75 | 5.8 |
| 0.8 | 2.9 | 0.8 | 4.8 | 0.8 | 6.0 | 0.8 | 5.8 |
| 0.85 | 2.7 | 0.85 | 4.5 | 0.85 | 5.5 | 0.85 | 5.7 |
| 0.9 | 2.4 | 0.9 | 3.8 | 0.9 | 4.7 | 0.9 | 4.5 |
| 0.95 | 1.9 | 0.95 | 2.8 | 0.95 | 3.3 | 0.95 | 3.5 |
| 1 | 1.2 | 1 | 1.2 | 1 | 1.2 | 1 | 1.2 |

HF-HCFO-1233xf-HCFO-1233zdE-HFO-1243zf

| Organics 0.9 F1233xf + 0.05 F1233zdE + 0.05 F1243zf | | Organics 0.05 F1233xf + 0.9 F1233zdE + 0.05 F1243zf | | Organics 0.05 F1233xf + 0.05 F1233zdE + 0.3 F1243zf | | Organics 0.4 F1233xf + 0.3 F1233zdE + 0.3 F1243zf | |
|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 1.8 | 0 | 1.6 | 0 | 5.5 | 0 | 3.0 |
| 0.05 | 2.9 | 0.05 | 2.7 | 0.05 | 6.4 | 0.05 | 4.1 |
| 0.1 | 2.9 | 0.1 | 2.7 | 0.1 | 6.5 | 0.1 | 4.1 |
| 0.15 | 2.9 | 0.15 | 2.7 | 0.15 | 6.5 | 0.15 | 4.1 |
| 0.2 | 2.9 | 0.2 | 2.7 | 0.2 | 6.5 | 0.2 | 4.1 |
| 0.25 | 2.9 | 0.25 | 2.7 | 0.25 | 6.5 | 0.25 | 4.1 |
| 0.3 | 2.9 | 0.3 | 2.7 | 0.3 | 6.5 | 0.3 | 4.1 |
| 0.35 | 2.9 | 0.35 | 2.7 | 0.35 | 6.5 | 0.35 | 4.1 |
| 0.4 | 2.9 | 0.4 | 2.7 | 0.4 | 6.5 | 0.4 | 4.1 |
| 0.45 | 2.9 | 0.45 | 2.7 | 0.45 | 6.5 | 0.45 | 4.1 |
| 0.5 | 2.9 | 0.5 | 2.7 | 0.5 | 6.4 | 0.5 | 4.1 |
| 0.55 | 2.9 | 0.55 | 2.7 | 0.55 | 6.4 | 0.55 | 4.1 |
| 0.6 | 2.9 | 0.6 | 2.7 | 0.6 | 6.4 | 0.6 | 4.0 |
| 0.65 | 2.9 | 0.65 | 2.7 | 0.65 | 6.4 | 0.65 | 4.0 |
| 0.7 | 2.9 | 0.7 | 2.7 | 0.7 | 6.3 | 0.7 | 4.0 |
| 0.75 | 2.9 | 0.75 | 2.7 | 0.75 | 6.1 | 0.75 | 3.9 |
| 0.8 | 2.7 | 0.8 | 2.6 | 0.8 | 5.8 | 0.8 | 3.7 |
| 0.85 | 2.5 | 0.85 | 2.4 | 0.85 | 5.3 | 0.85 | 3.4 |
| 0.9 | 2.2 | 0.9 | 2.1 | 0.9 | 4.5 | 0.9 | 2.9 |
| 0.95 | 1.8 | 0.95 | 1.7 | 0.95 | 3.2 | 0.95 | 2.2 |
| 1 | 1.2 | 1 | 1.2 | 1 | 1.2 | 1 | 1.2 |

HF-HCFO-1233xf-HFO-1234zeE-HFO-1243zf

| Organics 0.9 F1233xf + 0.05 F1234zeE + 0.05 F1243zf | | Organics 0.05 F1233xf + 0.9 F1234zeE + 0.05 F1243zf | | Organics 0.05 F1233xf + 0.05 F1234zeE + 0.9 F1243zf | | Organics 0.4 F1233xf + 0.3 F1234zeE + 0.3 F1243zf | |
|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 2.0 | 0 | 4.8 | 0 | 5.6 | 0 | 4.0 |
| 0.05 | 3.1 | 0.05 | 5.7 | 0.05 | 6.6 | 0.05 | 5.1 |
| 0.1 | 3.1 | 0.1 | 5.8 | 0.1 | 6.6 | 0.1 | 5.1 |

| Organics 0.9 F1233xf + 0.05 F1234zeE + 0.05 F1243zf | | Organics 0.05 F1233xf + 0.9 F1234zeE + 0.05 F1243zf | | Organics 0.05 F1233xf + 0.05 F1234zeE + 0.9 F1243zf | | Organics 0.4 F1233xf + 0.3 F1234zeE + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0.15 | 3.1 | 0.15 | 5.8 | 0.15 | 6.6 | 0.15 | 5.1 |
| 0.2  | 3.1 | 0.2  | 5.8 | 0.2  | 6.6 | 0.2  | 5.1 |
| 0.25 | 3.1 | 0.25 | 5.8 | 0.25 | 6.6 | 0.25 | 5.1 |
| 0.3  | 3.1 | 0.3  | 5.8 | 0.3  | 6.6 | 0.3  | 5.0 |
| 0.35 | 3.1 | 0.35 | 5.7 | 0.35 | 6.6 | 0.35 | 5.0 |
| 0.4  | 3.1 | 0.4  | 5.7 | 0.4  | 6.6 | 0.4  | 5.0 |
| 0.45 | 3.1 | 0.45 | 5.7 | 0.45 | 6.6 | 0.45 | 5.0 |
| 0.5  | 3.1 | 0.5  | 5.7 | 0.5  | 6.6 | 0.5  | 5.0 |
| 0.55 | 3.1 | 0.55 | 5.7 | 0.55 | 6.6 | 0.55 | 5.0 |
| 0.6  | 3.1 | 0.6  | 5.6 | 0.6  | 6.5 | 0.6  | 5.0 |
| 0.65 | 3.1 | 0.65 | 5.5 | 0.65 | 6.5 | 0.65 | 4.9 |
| 0.7  | 3.0 | 0.7  | 5.3 | 0.7  | 6.4 | 0.7  | 4.8 |
| 0.75 | 3.0 | 0.75 | 5.1 | 0.75 | 6.2 | 0.75 | 4.7 |
| 0.8  | 2.9 | 0.8  | 4.8 | 0.8  | 5.9 | 0.8  | 4.4 |
| 0.85 | 2.6 | 0.85 | 4.3 | 0.85 | 5.4 | 0.85 | 4.0 |
| 0.9  | 2.3 | 0.9  | 3.6 | 0.9  | 4.6 | 0.9  | 3.4 |
| 0.95 | 1.8 | 0.95 | 2.6 | 0.95 | 3.3 | 0.95 | 2.5 |
| 1    | 1.2 | 1    | 1.2 | 1    | 1.2 | 1    | 1.2 |

HF-HCFO-1233xf-HFO-1234zeZ-HFO-1243zf

| Organics 0.9 F1233xf + 0.05 F1234zeZ + 0.05 F1243zf | | Organics 0.05 F1233xf + 0.9 F1234zeZ + 0.05 F1243zf | | Organics 0.05 F1233xf + 0.05 F1234zeZ + 0.9 F1243zf | | Organics 0.4 F1233xf + 0.3 F1234zeZ + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0    | 1.8 | 0    | 2.0 | 0    | 5.5 | 0    | 3.1 |
| 0.05 | 2.9 | 0.05 | 3.1 | 0.05 | 6.4 | 0.05 | 4.2 |
| 0.1  | 2.9 | 0.1  | 3.1 | 0.1  | 6.5 | 0.1  | 4.2 |
| 0.15 | 2.9 | 0.15 | 3.1 | 0.15 | 6.5 | 0.15 | 4.2 |
| 0.2  | 2.9 | 0.2  | 3.1 | 0.2  | 6.5 | 0.2  | 4.2 |
| 0.25 | 2.9 | 0.25 | 3.1 | 0.25 | 6.5 | 0.25 | 4.2 |
| 0.3  | 2.9 | 0.3  | 3.1 | 0.3  | 6.5 | 0.3  | 4.2 |
| 0.35 | 2.9 | 0.35 | 3.1 | 0.35 | 6.5 | 0.35 | 4.2 |
| 0.4  | 2.9 | 0.4  | 3.1 | 0.4  | 6.5 | 0.4  | 4.2 |
| 0.45 | 2.9 | 0.45 | 3.1 | 0.45 | 6.5 | 0.45 | 4.2 |
| 0.5  | 2.9 | 0.5  | 3.1 | 0.5  | 6.4 | 0.5  | 4.2 |
| 0.55 | 2.9 | 0.55 | 3.1 | 0.55 | 6.4 | 0.55 | 4.2 |
| 0.6  | 2.9 | 0.6  | 3.1 | 0.5  | 6.4 | 0.6  | 4.1 |
| 0.65 | 2.9 | 0.65 | 3.1 | 0.65 | 6.4 | 0.65 | 4.1 |
| 0.7  | 2.9 | 0.7  | 3.1 | 0.7  | 6.3 | 0.7  | 4.1 |
| 0.75 | 2.9 | 0.75 | 3.1 | 0.75 | 6.1 | 0.75 | 4.0 |
| 0.8  | 2.8 | 0.8  | 3.0 | 0.8  | 5.8 | 0.8  | 3.8 |
| 0.85 | 2.5 | 0.85 | 2.7 | 0.85 | 5.3 | 0.85 | 3.5 |
| 0.9  | 2.2 | 0.9  | 2.4 | 0.9  | 4.5 | 0.9  | 3.0 |
| 0.95 | 1.8 | 0.95 | 1.9 | 0.95 | 3.2 | 0.95 | 2.3 |
| 1    | 1.2 | 1    | 1.2 | 1    | 1.2 | 1    | 1.2 |

HF-HCFO-1233xf-HFO-1234yf-HFO-1243zf

| Organics 0.9 F1233xf + 0.05 F1234yf + 0.05 F1243zf | | Organics 0.05 F1233xf + 0.9 F1234yf + 0.05 F1243zf | | Organics 0.05 F1233xf + 0.05 F1234yf + 0.9 F1243zf | | Organics 0.4 F1233xf + 0.3 F1234yf + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 2.1 | 0 | 6.5 | 0 | 5.8 | 0 | 4.6 |
| 0.05 | 3.2 | 0.05 | 7.5 | 0.05 | 5.8 | 0.05 | 5.6 |
| 0.1 | 3.2 | 0.1 | 7.5 | 0.1 | 8.8 | 0.1 | 5.7 |
| 0.15 | 3.2 | 0.15 | 7.5 | 0.15 | 5.8 | 0.15 | 5.6 |
| 0.2 | 3.2 | 0.2 | 7.5 | 0.2 | 6.8 | 0.2 | 5.6 |
| 0.25 | 3.2 | 0.25 | 7.5 | 0.25 | 6.8 | 0.25 | 5.6 |
| 0.3 | 3.2 | 0.3 | 7.5 | 0.3 | 6.8 | 0.3 | 5.6 |
| 0.35 | 3.2 | 0.35 | 7.5 | 0.35 | 6.8 | 0.35 | 5.6 |
| 0.4 | 3.2 | 0.4 | 7.5 | 0.4 | 6.8 | 0.4 | 5.6 |
| 0.45 | 3.2 | 0.45 | 7.5 | 0.45 | 6.8 | 0.45 | 5.6 |
| 0.5 | 3.2 | 0.5 | 7.5 | 0.5 | 6.8 | 0.5 | 5.6 |
| 0.55 | 3.2 | 0.55 | 7.5 | 0.55 | 6.7 | 0.55 | 5.6 |
| 0.6 | 3.2 | 0.6 | 7.5 | 0.6 | 6.7 | 0.6 | 5.6 |
| 0.65 | 3.2 | 0.65 | 7.5 | 0.65 | 6.7 | 0.65 | 5.6 |
| 0.7 | 3.2 | 0.7 | 7.4 | 0.7 | 6.6 | 0.7 | 5.6 |
| 0.75 | 3.2 | 0.75 | 7.3 | 0.75 | 6.4 | 0.75 | 5.4 |
| 0.8 | 3.0 | 0.8 | 7.0 | 0.8 | 6.1 | 0.8 | 5.1 |
| 0.85 | 2.8 | 0.85 | 6.4 | 0.85 | 5.6 | 0.85 | 4.7 |
| 0.9 | 2.4 | 0.9 | 5.4 | 0.9 | 4.8 | 0.9 | 4.0 |
| 0.95 | 1.9 | 0.95 | 3.7 | 0.95 | 3.4 | 0.95 | 2.9 |
| 1 | 1.2 | 1 | 1.2 | 1 | 1.2 | 1 | 1.2 |

HF-HFC-245cb-HCFO-1233zdE-HFO-1243zf

| Organics 0.9 F245cb + 0.05 F1233zdE + 0.05 F1243zf | | Organics 0.05 F245cb + 0.9 F1233zdE + 0.05 F1243zf | | Organics 0.05 F245cb + 0.05 F1233zdE + 0.9 F1243zf | | Organics 0.4 F245cb + 0.3 F1233zdE + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.6 | 0 | 1.9 | 0 | 5.6 | 0 | 4.2 |
| 0.05 | 5.7 | 0.05 | 2.9 | 0.05 | 6.6 | 0.05 | 5.3 |
| 0.1 | 5.7 | 0.1 | 2.9 | 0.1 | 5.6 | 0.1 | 5.3 |
| 0.15 | 5.7 | 0.15 | 2.9 | 0.15 | 6.6 | 0.15 | 5.3 |
| 0.2 | 5.7 | 0.2 | 2.9 | 0.2 | 6.6 | 0.2 | 5.3 |
| 0.25 | 5.7 | 0.25 | 2.9 | 0.25 | 6.6 | 0.25 | 5.3 |
| 0.3 | 5.7 | 0.3 | 2.9 | 0.3 | 6.6 | 0.3 | 5.3 |
| 0.35 | 5.7 | 0.35 | 2.9 | 0.35 | 6.6 | 0.35 | 5.3 |
| 0.4 | 5.7 | 0.4 | 2.9 | 0.4 | 6.6 | 0.4 | 5.3 |
| 0.45 | 5.7 | 0.45 | 2.9 | 0.45 | 6.6 | 0.45 | 5.3 |
| 0.5 | 5.7 | 0.5 | 2.9 | 0.5 | 6.6 | 0.5 | 5.3 |
| 0.55 | 5.7 | 0.55 | 2.9 | 0.55 | 6.6 | 0.55 | 5.3 |
| 0.6 | 5.7 | 0.6 | 2.9 | 0.6 | 6.5 | 0.6 | 5.3 |
| 0.65 | 5.7 | 0.65 | 2.9 | 0.65 | 6.5 | 0.65 | 5.3 |
| 0.7 | 5.8 | 0.7 | 2.9 | 0.7 | 6.4 | 0.7 | 5.3 |
| 0.75 | 5.8 | 0.75 | 2.9 | 0.75 | 6.2 | 0.75 | 5.3 |
| 0.8 | 5.8 | 0.8 | 2.8 | 0.8 | 6.0 | 0.8 | 5.1 |
| 0.85 | 5.7 | 0.85 | 2.6 | 0.85 | 5.5 | 0.85 | 4.7 |
| 0.9 | 4.9 | 0.9 | 2.3 | 0.9 | 4.7 | 0.9 | 4.1 |
| 0.95 | 3.5 | 0.95 | 1.8 | 0.95 | 3.3 | 0.95 | 2.9 |
| 1 | 1.2 | 1 | 1.2 | 1 | 1.2 | 1 | 1.2 |

HF-HCFO-1233zdE-HFO-1234zeE-HFO-1243zf

| Organics 0.9 F1233zdE + 0.05 F1234zeE + 0.05 F1243zf | | Organics 0.05 F1233zdE + 0.9 F1234zeE + 0.05 F1243zf | | Organics 0.05 F1233zdE + 0.05 F1234zeE + 0.9 F1243zf | | Organics 0.4 F1233zdE + 0.3 F1234zeE + 0.3 F1243zf | |
|---|---|---|---|---|---|---|---|
| HF HF | PRESSURE PRES bar | HF HF | PRESSURE PRES bar | HF HF | PRESSURE PRES bar | HF HF | PRESSURE PRES bar |
| 0 | 1.8 | 0 | 4.8 | 0 | 5.6 | 0 | 3.9 |
| 0.05 | 2.9 | 0.05 | 5.7 | 0.05 | 6.6 | 0.05 | 5.0 |
| 0.1 | 2.9 | 0.1 | 5.7 | 0.1 | 6.6 | 0.1 | 5.0 |
| 0.15 | 2.9 | 0.15 | 5.7 | 0.15 | 6.6 | 0.15 | 5.0 |
| 0.2 | 2.9 | 0.2 | 5.7 | 0.2 | 6.6 | 0.1 | 5.0 |
| 0.25 | 2.9 | 0.25 | 5.7 | 0.25 | 6.6 | 0.25 | 5.0 |
| 0.3 | 2.9 | 0.3 | 5.7 | 0.3 | 6.6 | 0.3 | 5.0 |
| 0.35 | 2.9 | 0.35 | 5.7 | 0.35 | 6.6 | 0.35 | 5.0 |
| 0.4 | 2.9 | 0.4 | 5.7 | 0.4 | 6.6 | 0.4 | 4.9 |
| 0.45 | 2.9 | 0.45 | 5.7 | 0.45 | 6.6 | 0.45 | 4.9 |
| 0.5 | 2.9 | 0.5 | 5.7 | 0.5 | 6.6 | 0.5 | 4.9 |
| 0.55 | 2.9 | 0.55 | 5.6 | 0.55 | 6.5 | 0.55 | 4.9 |
| 0.6 | 2.9 | 0.6 | 5.6 | 0.6 | 6.5 | 0.6 | 4.9 |
| 0.65 | 2.9 | 0.65 | 5.5 | 0.65 | 6.5 | 0.65 | 4.9 |
| 0.7 | 2.8 | 0.7 | 5.3 | 0.7 | 6.4 | 0.7 | 4.8 |
| 0.75 | 2.8 | 0.75 | 5.1 | 0.75 | 6.2 | 0.75 | 4.6 |
| 0.8 | 2.7 | 0.8 | 4.8 | 0.8 | 5.9 | 0.8 | 4.3 |
| 0.85 | 2.5 | 0.85 | 4.3 | 0.85 | 5.4 | 0.85 | 3.9 |
| 0.9 | 2.2 | 0.9 | 3.6 | 0.9 | 4.6 | 0.9 | 3.3 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF-HCFO-1233zdE-HFO-1234zeZ-HFO-1243zf

| Organics 0.9 F1233zdE + 0.05 F1234zeZ + 0.05 F1243zf | | Organics 0.05 F1233zdE + 0.9 F1234zeZ + 0.05 F1243zf | | Organics 0.05 F1233zdE + 0.05 F1234zeZ + 0.9 F1243zf | | Organics 0.4 F1233zdE + 0.3 F1234zeZ + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 1.6 | 0 | 2.0 | 0 | 5.5 | 0 | 3.0 |
| 0.05 | 2.7 | 0.05 | 3.1 | 0.05 | 6.4 | 0.05 | 4.1 |
| 0.1 | 2.7 | 0.1 | 3.1 | 0.1 | 6.5 | 0.1 | 4.1 |
| 0.15 | 2.7 | 0.15 | 3.1 | 0.15 | 6.5 | 0.15 | 4.1 |
| 0.2 | 2.7 | 0.2 | 3.1 | 0.2 | 6.5 | 0.2 | 4.1 |
| 0.25 | 2.7 | 0.25 | 3.1 | 0.25 | 6.5 | 0.25 | 4.1 |
| 0.3 | 2.7 | 0.3 | 3.1 | 0.3 | 6.4 | 0.3 | 4.1 |
| 0.35 | 2.7 | 0.35 | 3.1 | 0.35 | 6.4 | 0.35 | 4.1 |
| 0.4 | 2.7 | 0.4 | 3.1 | 0.4 | 6.4 | 0.4 | 4.1 |
| 0.45 | 2.7 | 0.45 | 3.1 | 0.45 | 6.4 | 0.45 | 4.1 |
| 0.5 | 2.7 | 0.5 | 3.1 | 0.5 | 6.4 | 0.5 | 4.1 |
| 0.55 | 2.7 | 0.55 | 3.1 | 0.55 | 6.4 | 0.55 | 4.1 |
| 0.6 | 2.7 | 0.6 | 3.1 | 0.6 | 6.4 | 0.6 | 4.1 |
| 0.65 | 2.7 | 0.65 | 3.1 | 0.65 | 6.3 | 0.65 | 4.0 |
| 0.7 | 2.7 | 0.7 | 3.1 | 0.7 | 6.3 | 0.7 | 4.0 |
| 0.75 | 2.7 | 0.75 | 3.1 | 0.75 | 6.1 | 0.75 | 3.9 |
| 0.8 | 2.6 | 0.8 | 3.0 | 0.8 | 5.8 | 0.8 | 3.7 |
| 0.85 | 2.4 | 0.85 | 2.7 | 0.85 | 5.3 | 0.85 | 3.4 |
| 0.9 | 2.1 | 0.9 | 2.4 | 0.9 | 4.5 | 0.9 | 2.9 |
| 0.95 | 1.7 | 0.95 | 1.9 | 0.95 | 3.2 | 0.95 | 2.2 |
| 1 | 1.2 | 1 | 1.2 | 1 | 1.2 | 1 | 1.2 |

HF-HFO-1234yf-HCFO-1233zdE-HFO-1243zf

| Organics 0.9 F1234yf + 0.05 F1233zdE + 0.05 F1243zf | | Organics 0.05 F1234yf + 0.9 F1233zdE + 0.05 F1243zf | | Organics 0.05 F1234yf + 0.05 F1233zdE + 0.9 F1243zf | | Organics 0.4 F1234yf + 0.3 F1233zdE + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 1.9 | 0 | 5.7 | 0 | 5.0 |
| 0.05 | 7.5 | 0.05 | 3.0 | 0.05 | 6.7 | 0.05 | 6.0 |
| 0.1 | 7.5 | 0.1 | 3.0 | 0.1 | 6.7 | 0.1 | 6.0 |
| 0.15 | 7.5 | 0.15 | 3.0 | 0.15 | 6.7 | 0.15 | 6.0 |
| 0.2 | 7.4 | 0.2 | 3.0 | 0.2 | 6.7 | 0.2 | 6.0 |
| 0.25 | 7.4 | 0.25 | 3.0 | 0.25 | 6.7 | 0.25 | 6.0 |
| 0.3 | 7.5 | 0.3 | 3.0 | 0.3 | 6.7 | 0.3 | 6.0 |
| 0.35 | 7.5 | 0.35 | 3.0 | 0.35 | 6.7 | 0.35 | 6.0 |
| 0.4 | 7.5 | 0.4 | 3.0 | 0.4 | 6.7 | 0.4 | 6.0 |
| 0.45 | 7.5 | 0.45 | 3.0 | 0.45 | 6.7 | 0.45 | 6.0 |
| 0.5 | 7.5 | 0.5 | 3.0 | 0.5 | 6.6 | 0.5 | 6.0 |
| 0.55 | 7.5 | 0.55 | 3.0 | 0.55 | 6.6 | 0.55 | 6.0 |
| 0.6 | 7.5 | 0.6 | 3.0 | 0.6 | 6.6 | 0.6 | 6.0 |
| 0.65 | 7.5 | 0.65 | 3.0 | 0.65 | 6.6 | 0.65 | 6.0 |
| 0.7 | 7.4 | 0.7 | 3.0 | 0.7 | 6.5 | 0.7 | 6.0 |
| 0.75 | 7.3 | 0.75 | 3.0 | 0.75 | 6.3 | 0.75 | 5.8 |
| 0.8 | 7.0 | 0.8 | 2.8 | 0.8 | 6.0 | 0.8 | 5.5 |
| 0.05 | 6.4 | 0.85 | 2.6 | 0.85 | 5.5 | 0.85 | 5.1 |
| 0.9 | 5.4 | 0.9 | 2.3 | 0.9 | 4.7 | 0.9 | 4.3 |
| 0.95 | 3.7 | 0.95 | 1.8 | 0.95 | 3.3 | 0.95 | 3.1 |
| 1 | 1.2 | 1 | 1.2 | 1 | 1.2 | 1 | 1.2 |

HF-HFO-1234zeE-HFO-1234zeZ-HFO-1243zf

| Organics 0.9 F1234zeE + 0.05 F1234zeZ + 0.05 F1243zf | | Organics 0.05 F1234zeE + 0.9 F1234zeZ + 0.05 F1243zf | | Organics 0.05 F1234zeE + 0.05 F1234zeZ + 0.9 F1243zf | | Organics 0.4 F1234zeE + 0.3 F1234zeZ + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.8 | 0 | 2.2 | 0 | 5.6 | 0 | 4.3 |
| 0.05 | 5.7 | 0.05 | 3.3 | 0.05 | 6.6 | 0.05 | 5.3 |
| 0.1 | 5.8 | 0.1 | 3.3 | 0.1 | 6.6 | 0.1 | 5.3 |
| 0.15 | 5.8 | 0.15 | 3.3 | 0.15 | 6.6 | 0.15 | 5.3 |
| 0.2 | 5.7 | 0.2 | 3.3 | 0.2 | 6.6 | 0.2 | 5.3 |
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.7 | 0.55 | 3.3 | 0.55 | 6.5 | 0.55 | 5.3 |
| 0.6 | 5.6 | 0.6 | 3.3 | 0.6 | 6.5 | 0.6 | 5.3 |
| 0.65 | 5.5 | 0.65 | 3.3 | 0.65 | 6.5 | 0.65 | 5.2 |
| 0.7 | 5.3 | 0.7 | 3.3 | 0.7 | 6.4 | 0.7 | 5.1 |
| 0.75 | 5.1 | 0.75 | 3.2 | 0.75 | 6.2 | 0.75 | 4.9 |
| 0.8 | 4.8 | 0.8 | 3.1 | 0.8 | 5.9 | 0.8 | 4.6 |
| 0.85 | 4.3 | 0.85 | 2.8 | 0.85 | 5.4 | 0.85 | 4.2 |
| 0.9 | 3.6 | 0.9 | 2.5 | 0.9 | 4.6 | 0.9 | 3.6 |
| 0.95 | 2.6 | 0.95 | 2.0 | 0.95 | 3.3 | 0.95 | 2.6 |
| 1 | 1.2 | 1 | 1.2 | 1 | 1.2 | 1 | 1.2 |

HF-HFO-1234yf-HFO-1234zeE-HFO-1243zf

| Organics 0.9 F1234yf + 0.05 F1234zeE + 0.05 F1243zf | | Organics 0.05 F1234yf + 0.9 F1234zeE + 0.05 F1243zf | | Organics 0.05 F1234yf + 0.05 F1234zeE + 0.9 F1243zf | | Organics 0.4 F1234yf + 0.3 F1234zeE + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.7 | 0 | 5.0 | 0 | 5.8 | 0 | 5.9 |
| 0.05 | 7.6 | 0.05 | 6.0 | 0.05 | 6.8 | 0.05 | 6.9 |
| 0.1 | 7.6 | 0.1 | 6.0 | 0.1 | 6.8 | 0.1 | 6.9 |
| 0.15 | 7.6 | 0.15 | 6.0 | 0.15 | 6.8 | 0.15 | 6.9 |
| 0.2 | 7.6 | 0.2 | 6.0 | 0.2 | 6.8 | 0.2 | 6.9 |
| 0.25 | 7.5 | 0.25 | 6.0 | 0.25 | 6.8 | 0.25 | 6.9 |
| 0.3 | 7.6 | 0.3 | 6.0 | 0.3 | 6.8 | 0.3 | 6.9 |
| 0.35 | 7.6 | 0.35 | 6.0 | 0.35 | 6.8 | 0.35 | 6.9 |
| 0.4 | 7.6 | 0.4 | 6.0 | 0.4 | 6.8 | 0.4 | 6.9 |
| 0.45 | 7.6 | 0.45 | 6.0 | 0.45 | 6.8 | 0.45 | 6.9 |
| 0.5 | 7.6 | 0.5 | 6.0 | 0.5 | 6.8 | 0.5 | 6.9 |
| 0.55 | 7.6 | 0.55 | 5.9 | 0.55 | 6.8 | 0.55 | 6.9 |
| 0.6 | 7.6 | 0.6 | 5.8 | 0.6 | 6.7 | 0.5 | 6.9 |
| 0.65 | 7.6 | 0.65 | 5.7 | 0.65 | 6.7 | 0.65 | 6.8 |
| 0.7 | 7.6 | 0.7 | 5.6 | 0.7 | 6.6 | 0.7 | 6.7 |
| 0.75 | 7.4 | 0.75 | 5.4 | 0.75 | 6.4 | 0.75 | 6.5 |
| 0.8 | 7.1 | 0.8 | 5.0 | 0.8 | 6.1 | 0.8 | 6.2 |
| 0.85 | 6.5 | 0.85 | 4.5 | 0.85 | 5.6 | 0.85 | 5.7 |
| 0.9 | 5.5 | 0.9 | 3.8 | 0.9 | 4.8 | 0.9 | 4.8 |
| 0.95 | 3.8 | 0.95 | 2.7 | 0.95 | 3.4 | 0.95 | 3.3 |
| 1 | 1.2 | 1 | 1.2 | 1 | 1.2 | 1 | 1.2 |

HF-HFO-1234yf-HFO-1234zeZ-HFO-1243zf

| Organics 0.9 F1234yf + 0.05 F1234zeZ + 0.05 F1243zf | | Organics 0.05 F1234yf + 0.9 F1234zeZ + 0.05 F1243zf | | Organics 0.05 F1234yf + 0.05 F1234zeZ + 0.9 F1243zf | | Organics 0.4 F1234yf + 0.3 F1234zeZ + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 2.3 | 0 | 5.7 | 0 | 5.0 |
| 0.05 | 7.5 | 0.05 | 3.4 | 0.05 | 6.7 | 0.05 | 6.0 |
| 0.1 | 7.5 | 0.1 | 3.4 | 0.1 | 6.7 | 0.1 | 6.1 |
| 0.15 | 7.5 | 0.15 | 3.4 | 0.15 | 6.7 | 0.15 | 6.1 |
| 0.2 | 7.4 | 0.2 | 3.4 | 0.2 | 6.7 | 0.2 | 6.1 |
| 0.25 | 7.4 | 0.25 | 3.4 | 0.25 | 6.7 | 0.25 | 6.1 |
| 0.3 | 7.4 | 0.3 | 3.4 | 0.3 | 6.7 | 0.3 | 6.1 |
| 0.35 | 7.5 | 0.35 | 3.4 | 0.35 | 6.7 | 0.35 | 6.1 |
| 0.4 | 7.5 | 0.4 | 3.4 | 0.4 | 6.7 | 0.4 | 6.1 |
| 0.45 | 7.5 | 0.45 | 3.4 | 0.45 | 6.7 | 0.45 | 6.1 |
| 0.5 | 7.5 | 0.5 | 3.4 | 0.5 | 6.7 | 0.5 | 6.1 |
| 0.55 | 7.5 | 0.55 | 3.4 | 0.55 | 6.6 | 0.55 | 6.1 |
| 0.6 | 7.5 | 0.6 | 3.4 | 0.6 | 6.6 | 0.6 | 6.1 |
| 0.65 | 7.5 | 0.65 | 3.4 | 0.65 | 6.6 | 0.55 | 6.1 |
| 0.7 | 7.4 | 0.7 | 3.4 | 0.7 | 6.5 | 0.7 | 6.0 |
| 0.75 | 7.3 | 0.75 | 3.3 | 0.75 | 6.3 | 0.75 | 5.9 |
| 0.8 | 7.0 | 0.8 | 3.2 | 0.8 | 6.0 | 0.8 | 5.6 |
| 0.85 | 6.4 | 0.85 | 3.0 | 0.85 | 5.5 | 0.85 | 5.1 |
| 0.9 | 5.4 | 0.9 | 2.6 | 0.9 | 4.7 | 0.9 | 4.4 |
| 0.95 | 3.7 | 0.95 | 2.0 | 0.95 | 3.3 | 0.95 | 3.1 |
| 1 | 1.2 | 1 | 1.2 | 1 | 1.2 | 1 | 1.2 |

HF-HFO-1234yf-HFO-1243zf-HFC-245cb

| Organics 0.9 F1234yf + 0.05 F1243zf + 0.05 F245cb | | Organics 0.4 F1234yf + 0.3 F1243zf + 0.3 F245cb | | Organics 0.05 F1234yf + 0.9 F1243zf + 0.05 F245cb | | Organics 0.05 F1234yf + 0.05 F1243zf + 0.9 F245cb | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.7 | 0 | 5.9 | 0 | 5.8 | 0 | 4.9 |
| 0.05 | 7.6 | 0.05 | 6.9 | 0.05 | 6.8 | 0.05 | 6.0 |
| 0.1 | 7.6 | 0.1 | 7.0 | 0.1 | 6.8 | 0.1 | 6.0 |
| 0.15 | 7.6 | 0.15 | 6.9 | 0.15 | 6.8 | 0.15 | 6.0 |
| 0.2 | 7.6 | 0.2 | 6.9 | 0.2 | 6.8 | 0.2 | 6.0 |
| 0.25 | 7.6 | 0.25 | 6.9 | 0.25 | 6.8 | 0.25 | 6.0 |
| 0.3 | 7.6 | 0.3 | 6.9 | 0.3 | 6.8 | 0.3 | 6.0 |
| 0.35 | 7.6 | 0.35 | 6.9 | 0.35 | 6.8 | 0.35 | 6.0 |
| 0.4 | 7.6 | 0.4 | 6.9 | 0.4 | 6.8 | 0.4 | 6.0 |
| 0.45 | 7.6 | 0.45 | 6.9 | 0.45 | 6.8 | 0.45 | 6.0 |
| 0.5 | 7.6 | 0.5 | 6.9 | 0.5 | 6.8 | 0.5 | 6.0 |
| 0.55 | 7.6 | 0.55 | 6.9 | 0.55 | 6.8 | 0.55 | 6.0 |
| 0.6 | 7.6 | 0.6 | 6.9 | 0.6 | 6.8 | 0.6 | 6.0 |
| 0.65 | 7.6 | 0.65 | 6.9 | 0.65 | 6.7 | 0.65 | 6.0 |
| 0.7 | 7.6 | 0.7 | 6.9 | 0.7 | 6.6 | 0.7 | 6.0 |
| 0.75 | 7.5 | 0.75 | 6.9 | 0.75 | 6.5 | 0.75 | 6.0 |
| 0.8 | 7.2 | 0.8 | 6.6 | 0.8 | 6.2 | 0.8 | 6.0 |
| 0.85 | 6.6 | 0.85 | 6.1 | 0.85 | 5.7 | 0.85 | 5.9 |
| 0.9 | 5.5 | 0.9 | 5.2 | 0.9 | 4.8 | 0.9 | 5.1 |
| 0.95 | 3.8 | 0.95 | 3.6 | 0.95 | 3.4 | 0.95 | 3.6 |
| 1 | 1.2 | 1 | 1.2 | 1 | 1.2 | 1 | 1.2 |

HF-HFC-245th-HFO-1234zeE-HFO-1243zf

| Organics 0.9 F245cb + 0.05 F1234zeE + 0.05 F1243zf | | Organics 0.05 F245cb + 0.9 F1234zeE + 0.05 F1243zf | | Organics 0.05 F245cb + 0.05 F1234zeE + 0.9 F1243zf | | Organics 0.4 F245cb + 0.3 F1234zeE + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.8 | 0 | 4.9 | 0 | 5.8 | 0 | 5.2 |
| 0.05 | 5.9 | 0.05 | 5.9 | 0.05 | 6.7 | 0.05 | 6.2 |
| 0.1 | 5.9 | 0.1 | 5.9 | 0.1 | 6.7 | 0.1 | 6.2 |
| 0.15 | 5.9 | 0.15 | 5.9 | 0.15 | 6.7 | 0.15 | 6.2 |
| 0.2 | 5.9 | 0.2 | 5.9 | 0.2 | 6.7 | 0.2 | 6.2 |
| 0.25 | 5.9 | 0.25 | 5.9 | 0.25 | 6.7 | 0.25 | 6.2 |
| 0.3 | 5.9 | 0.3 | 5.9 | 0.3 | 6.7 | 0.3 | 6.2 |
| 0.35 | 5.9 | 0.35 | 5.9 | 0.35 | 6.7 | 0.35 | 6.2 |
| 0.4 | 5.9 | 0.4 | 5.9 | 0.4 | 6.7 | 0.4 | 6.2 |
| 0.45 | 5.9 | 0.45 | 5.9 | 0.45 | 6.7 | 0.45 | 6.2 |
| 0.5 | 5.9 | 0.5 | 5.9 | 0.5 | 6.7 | 0.5 | 6.2 |
| 0.55 | 5.9 | 0.55 | 5.8 | 0.55 | 6.7 | 0.55 | 6.2 |
| 0.6 | 5.9 | 0.6 | 5.8 | 0.6 | 6.7 | 0.6 | 6.2 |
| 0.05 | 5.9 | 0.65 | 5.7 | 0.65 | 6.6 | 0.65 | 6.2 |
| 0.7 | 5.9 | 0.7 | 5.5 | 0.7 | 6.5 | 0.7 | 6.2 |
| 0.75 | 5.9 | 0.75 | 5.3 | 0.75 | 6.4 | 0.75 | 6.1 |
| 0.8 | 5.9 | 0.8 | 5.0 | 0.8 | 6.1 | 0.8 | 5.8 |
| 0.85 | 5.8 | 0.85 | 4.5 | 0.85 | 5.6 | 0.85 | 5.3 |
| 0.9 | 5.0 | 0.9 | 3.7 | 0.9 | 4.7 | 0.9 | 4.5 |
| 0.95 | 3.5 | 0.95 | 2.7 | 0.95 | 3.4 | 0.95 | 3.2 |
| 1 | 1.2 | 1 | 1.2 | 1 | 1.2 | 1 | 1.2 |

HF-HFC-245cb-HFO-1234zeZ-HFO-1243zf

| Organics 0.9 F245cb + 0.05 F1234zeZ + 0.05 F1243zf | | Organics 0.05 F245cb + 0.9 F1234zeZ + 0.05 F1243zf | | Organics 0.05 F245cb + 0.05 F1234zeZ + 0.9 F1243zf | | Organics 0.4 F245cb + 0.3 F1234zeZ + 0.3 F1243zf | |
|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.6 | 0 | 2.2 | 0 | 5.6 | 0 | 4.2 |
| 0.05 | 5.7 | 0.05 | 3.3 | 0.05 | 6.6 | 0.05 | 5.3 |
| 0.1 | 5.7 | 0.1 | 3.3 | 0.1 | 6.6 | 0.1 | 5.3 |
| 0.15 | 5.7 | 0.15 | 3.3 | 0.15 | 6.6 | 0.15 | 5.3 |
| 0.2 | 5.7 | 0.2 | 3.3 | 0.2 | 6.6 | 0.2 | 5.3 |
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.7 | 0.55 | 3.3 | 0.55 | 6.6 | 0.55 | 5.3 |
| 0.6 | 5.8 | 0.6 | 3.3 | 0.6 | 6.5 | 0.6 | 5.3 |
| 0.65 | 5.8 | 0.65 | 3.3 | 0.65 | 6.5 | 0.65 | 5.3 |
| 0.7 | 5.8 | 0.7 | 3.3 | 0.7 | 6.4 | 0.7 | 5.4 |
| 0.75 | 5.8 | 0.75 | 3.3 | 0.75 | 6.3 | 0.75 | 5.4 |
| 0.8 | 5.8 | 0.8 | 3.1 | 0.8 | 6.0 | 0.8 | 5.2 |
| 0.85 | 5.7 | 0.85 | 2.9 | 0.85 | 5.5 | 0.85 | 4.8 |
| 0.9 | 4.9 | 0.9 | 2.6 | 0.9 | 4.7 | 0.9 | 4.1 |
| 0.95 | 3.5 | 0.95 | 2.0 | 0.95 | 3.3 | 0.95 | 3.0 |
| 1 | 1.2 | 1 | 1.2 | 1 | 1.2 | 1 | 1.2 |

EXAMPLE 5: TEMPERATURE AND PRESSURE RANGE OF QUATERNARY MIXTURES

| Quaternary | Boiling point range | |
|---|---|---|
| | Temperature ° C. | Pressure bar abs |
| HF-HCFO-1233xf-HFC-245cb-HFO-1243zf | 0 to 40 | ~1.2 to ~10.1 |
| HF-HFO-1234yf-HFC-245cb-HFO-1243zf | 0 to 40 | ~2.5 to ~11.6 |
| HF-HCFO-1233xf-HFO-1234yf-HFO-1243zf | 0 to 40 | ~1.3 to ~11.3 |
| HF-HCFO-1233xf-HCFO-1233zdE-HFO-1243zf | 0 to 40 | ~1.0 to ~9.9 |
| HF-HCFO-1233xf-HFO-1234zeE-HFO-1243zf | 0 to 40 | ~1.2 to ~10.1 |
| HF-HCFO-1233xf-HFO-1234zeZ-HFO-1243zf | 0 to 40 | ~1.1 to ~9.9 |
| HF-HFO-1234yf-HFO-1234zeE-HFO-1243zf | 0 to 40 | ~3.0 to ~11.6 |
| HF-HFO-1234yf-HFO-1234zeZ-HFO-1243zf | 0 to 40 | ~1.3 to ~11.3 |
| HF-HFC-245cb-HCFO-1233zdE-HFO-1243zf | 0 to 40 | ~1.1 to ~10.1 |
| HF-HFC-245cb-HFO-1234zeE-HFO-1243zf | 0 to 40 | ~2.5 to ~10.3 |
| HF-HFC-245cb-HFO-1234zeZ-HFO-1243zf | 0 to 40 | ~1.3 to ~10.1 |
| HF-HCFO-1233zdE-HFO-1234zeE-HFO-1243zf | 0 to 40 | ~1.1 to ~10.1 |
| HF-HCFO-1233zdE-HFO-1234zeZ-HFO-1243zf | 0 to 40 | ~1.0 to ~9.9 |
| HF-HFO-1234zeE-HFO-1234zeZ-HFO-1243zf | 0 to 40 | ~1.3 to ~10.1 |
| HF-HFO-1234yf-HCFO-1233zdE-HFO-1243zf | 0 to 40 | ~1.2 to ~11.3 |

EXAMPLE 6: DECANTATION RANGE OF QUATERNARY MIXTURES

| Quaternary | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HFO-1243zf | 5-75 | 5-70 | 15-60 |
| HF-HFO-1234yf-HFC-245cb-HFO-1243zf | 5-75 | 15-70 | 45-70 |
| HF-HCFO-1233xf-HFO-1234yf-HFO-1243zf | 5-75 | 10-65 | * |
| HF-HCFO-1233xf-HCFO-1233zdE-HFO-1243zf | 5-75 | 5-70 | 10-60 |
| HF-HCFO-1233xf-HFO-1234zeE-HFO-1243zf | 5-70 | 10-60 | * |
| HF-HCFO-1233xf-HFO-1234zeZ-HFO-1243zf | 5-75 | 5-70 | 10-55 |
| HF-HFO-1234yf-HFO-1234zeE-HFO-1243zf | 5-65 | * | * |
| HF-HFO-1234yf-HFO-1234zeZ-HFO-1243zf | 5-75 | 10-65 | * |
| HF-HFC-245cb-HCFO-1233zdE-HFO-1243zf | 5-75 | 5-70 | 15-65 |
| HF-HFC-245cb-HFO-1234zeE-HFO-1243zf | 5-75 | 15-65 | * |
| HF-HFC-245cb-HFO-1234zeZ-HFO-1243zf | 5-75 | 10-70 | 20-60 |
| HF-HCFO-1233zdE-HFO-1234zeE-HFO-1243zf | 5-70 | 10-60 | * |
| HF-HCFO-1233zdE-HFO-1234zeZ-HFO-1243zf | 5-75 | 5-70 | 10-55 |
| HF-HFO-1234zeE-HFO-1234zeZ-HFO-1243zf | 5-70 | 10-60 | * |
| HF-HFO-1234yf-HCFO-1233zdE-HFO-1243zf | 5-75 | 10-65 | * |

EXAMPLE 7: PENTERNARY MIXTURES, ISOTHERM AT 25° C.

HF-HCFO-1233xf-HFC-245cb-HCFO-1233zdE-HFO-1243zf

| Organics 0.9 F1233xf + 0.033 F1233zdE + 0.033 F245cb + 0.034 F1243zf | | Organics 0.033 F1233xf + 0.9 F1233zdE + 0.033 F245cb + 0.034 F1243zf | | Organics 0.033 F1233xf + 0.033 F1233zdE + 0.9 F245cb + 0.034 F1243zf | | Organics 0.034 F1233xf + 0.033 F1233zdE + 0.033 F245cb + 0.9 F1243zf | | Organics 0.25 F1233xf + 0.25 F1233zdE + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 1.8 | 0 | 1.6 | 0 | 4.5 | 0 | 5.6 | 0 | 3.5 |
| 0.05 | 3.0 | 0.05 | 2.8 | 0.05 | 5.7 | 0.05 | 6.5 | 0.05 | 4.6 |
| 0.1 | 3.0 | 0.1 | 2.8 | 0.1 | 5.7 | 0.1 | 6.6 | 0.1 | 4.6 |
| 0.15 | 3.0 | 0.15 | 2.8 | 0.15 | 5.7 | 0.15 | 6.6 | 0.15 | 4.6 |
| 0.2 | 3.0 | 0.2 | 2.8 | 0.2 | 5.7 | 0.2 | 6.5 | 0.2 | 4.6 |
| 0.25 | 3.0 | 0.25 | 2.8 | 0.25 | 5.7 | 0.25 | 6.5 | 0.25 | 4.6 |
| 0.3 | 3.0 | 0.3 | 2.8 | 0.3 | 5.7 | 0.3 | 6.5 | 0.3 | 4.6 |
| 0.35 | 2.9 | 0.35 | 2.8 | 0.35 | 5.7 | 0.35 | 6.5 | 0.35 | 4.6 |
| 0.4 | 2.9 | 0.4 | 2.8 | 0.4 | 5.7 | 0.4 | 6.5 | 0.4 | 4.6 |
| 0.45 | 2.9 | 0.45 | 2.7 | 0.45 | 5.7 | 0.45 | 6.5 | 0.45 | 4.6 |
| 0.5 | 2.9 | 0.5 | 2.7 | 0.5 | 5.7 | 0.5 | 6.5 | 0.5 | 4.6 |
| 0.55 | 2.9 | 0.55 | 2.7 | 0.55 | 5.7 | 0.55 | 6.5 | 0.55 | 4.6 |
| 0.6 | 2.9 | 0.6 | 2.7 | 0.6 | 5.7 | 0.6 | 6.5 | 0.6 | 4.6 |
| 0.65 | 2.9 | 0.65 | 2.7 | 0.65 | 5.7 | 0.65 | 6.4 | 0.65 | 4.6 |
| 0.7 | 2.9 | 0.7 | 2.7 | 0.7 | 5.7 | 0.7 | 6.4 | 0.7 | 4.7 |
| 0.75 | 2.9 | 0.75 | 2.7 | 0.75 | 5.7 | 0.75 | 6.2 | 0.75 | 4.6 |
| 0.8 | 2.8 | 0.8 | 2.6 | 0.8 | 5.7 | 0.8 | 5.9 | 0.8 | 4.4 |
| 0.85 | 2.6 | 0.85 | 2.4 | 0.85 | 5.6 | 0.85 | 5.4 | 0.85 | 4.1 |
| 0.9 | 2.3 | 0.9 | 2.2 | 0.9 | 4.8 | 0.9 | 4.6 | 0.9 | 3.5 |
| 0.95 | 1.8 | 0.95 | 1.8 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF-HCFO-1233xf-HFC-245cb-HFO-1234zeE-HFO-1243zf

| Organics 0.9 F1233xf + 0.033 F1234zeE + 0.033 F245cb + 0.034 F1243zf | | Organics 0.033 F1233xf + 0.9 F1234zeE + 0.033 F245cb + 0.034 F1243zf | | Organics 0.033 F1233xf + 0.033 F1234zeE + 0.9 F245cb + 0.034 F1243zf | | Organics 0.034 F1233xf + 0.033 F1234zeE + 0.033 F245cb + 0.9 F1243zf | | Organics 0.25 F1233xf + 0.25 F1234zeE + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 2.0 | 0 | 4.8 | 0 | 4.6 | 0 | 5.7 | 0 | 4.4 |
| 0.05 | 3.1 | 0.05 | 5.8 | 0.05 | 5.8 | 0.05 | 6.6 | 0.05 | 5.4 |
| 0.1 | 3.1 | 0.1 | 5.8 | 0.1 | 5.8 | 0.1 | 6.7 | 0.1 | 5.4 |
| 0.15 | 3.1 | 0.15 | 5.8 | 0.15 | 5.8 | 0.15 | 6.6 | 0.15 | 5.4 |
| 0.2 | 3.1 | 0.2 | 5.8 | 0.2 | 5.8 | 0.2 | 6.6 | 0.2 | 5.4 |
| 0.25 | 3.1 | 0.25 | 5.8 | 0.25 | 5.8 | 0.25 | 6.6 | 0.25 | 5.4 |
| 0.3 | 3.1 | 0.3 | 5.8 | 0.3 | 5.8 | 0.3 | 6.6 | 0.3 | 5.4 |
| 0.35 | 3.1 | 0.35 | 5.8 | 0.35 | 5.8 | 0.35 | 6.6 | 0.35 | 5.4 |
| 0.4 | 3.1 | 0.4 | 5.8 | 0.4 | 5.8 | 0.4 | 6.6 | 0.4 | 5.4 |
| 0.45 | 3.1 | 0.45 | 5.8 | 0.45 | 5.8 | 0.45 | 6.6 | 0.45 | 5.4 |
| 0.5 | 3.1 | 0.5 | 5.7 | 0.5 | 5.8 | 0.5 | 6.6 | 0.5 | 5.4 |
| 0.55 | 3.1 | 0.55 | 5.7 | 0.55 | 5.8 | 0.55 | 6.6 | 0.55 | 5.4 |
| 0.6 | 3.1 | 0.6 | 5.6 | 0.6 | 5.8 | 0.6 | 6.6 | 0.6 | 5.4 |
| 0.65 | 3.1 | 0.65 | 5.5 | 0.65 | 5.8 | 0.65 | 6.5 | 0.65 | 5.4 |
| 0.7 | 3.1 | 0.7 | 5.4 | 0.7 | 5.8 | 0.7 | 6.4 | 0.7 | 5.4 |
| 0.75 | 3.0 | 0.75 | 5.2 | 0.75 | 5.8 | 0.75 | 6.3 | 0.75 | 5.3 |
| 0.8 | 2.9 | 0.8 | 4.8 | 0.8 | 5.8 | 0.8 | 6.0 | 0.8 | 5.0 |
| 0.85 | 2.7 | 0.85 | 4.3 | 0.85 | 5.7 | 0.85 | 5.5 | 0.85 | 4.6 |
| 0.9 | 2.3 | 0.9 | 3.6 | 0.9 | 4.9 | 0.9 | 4.7 | 0.9 | 3.9 |
| 0.95 | 1.9 | 0.95 | 2.6 | 0.95 | 3.5 | 0.95 | 3.3 | 0.95 | 2.8 |
| 1 | 1.2 | 1 | 1.2 | 1 | 1.2 | 1 | 1.2 | 1 | 1.2 |

HF-HCFO-1233xf-HFC-245cb-HFO-1234zeZ-HFO-1243zf

| Organics 0.9 F1233xf + 0.033 F1234zeZ + 0.033 F245cb + 0.034 F1243zf | | Organics 0.033 F1233xf + 0.9 F1234zeZ + 0.033 F245cb + 0.034 F1243zf | | Organics 0.033 F1233xf + 0.033 F1234zeZ + 0.9 F245cb + 0.034 F1243zf | | Organics 0.034 F1233xf + 0.033 F1234zeZ + 0.033 F245cb + 0.9 F1243zf | | Organics 0.25 F1233xf + 0.25 F1234zeZ + 0.25 F245cb + 0.25 F1243zf | |
|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 1.9 | 0 | 2.1 | 0 | 4.5 | 0 | 5.6 | 0 | 3.6 |
| 0.05 | 3.0 | 0.05 | 3.2 | 0.05 | 5.7 | 0.05 | 6.5 | 0.05 | 4.7 |
| 0.1 | 3.0 | 0.1 | 3.2 | 0.1 | 5.7 | 0.1 | 6.6 | 0.1 | 4.7 |
| 0.15 | 3.0 | 0.15 | 3.2 | 0.15 | 5.7 | 0.15 | 6.6 | 0.15 | 4.7 |
| 0.2 | 3.0 | 0.2 | 3.2 | 0.2 | 5.7 | 0.2 | 6.6 | 0.2 | 4.7 |
| 0.25 | 3.0 | 0.25 | 3.2 | 0.25 | 5.7 | 0.25 | 6.5 | 0.25 | 4.7 |
| 0.3 | 3.0 | 0.3 | 3.2 | 0.3 | 5.7 | 0.3 | 6.5 | 0.3 | 4.7 |
| 0.35 | 3.0 | 0.35 | 3.2 | 0.35 | 5.7 | 0.35 | 6.5 | 0.35 | 4.7 |
| 0.4 | 3.0 | 0.4 | 3.2 | 0.4 | 5.7 | 0.4 | 6.5 | 0.4 | 4.7 |
| 0.45 | 3.0 | 0.45 | 3.2 | 0.45 | 5.7 | 0.45 | 6.5 | 0.45 | 4.7 |
| 0.5 | 3.0 | 0.5 | 3.2 | 0.5 | 5.7 | 0.5 | 6.5 | 0.5 | 4.7 |
| 0.55 | 3.0 | 0.55 | 3.2 | 0.55 | 5.7 | 0.55 | 6.5 | 0.55 | 4.7 |
| 0.6 | 3.0 | 0.6 | 3.2 | 0.6 | 5.7 | 0.6 | 6.5 | 0.6 | 4.7 |
| 0.65 | 3.0 | 0.65 | 3.2 | 0.65 | 5.7 | 0.65 | 6.5 | 0.65 | 4.7 |
| 0.7 | 3.0 | 0.7 | 3.2 | 0.7 | 5.7 | 0.7 | 6.4 | 0.7 | 4.7 |
| 0.75 | 3.0 | 0.75 | 3.2 | 0.75 | 5.7 | 0.75 | 6.2 | 0.75 | 4.7 |
| 0.8 | 2.8 | 0.8 | 3.0 | 0.8 | 5.7 | 0.8 | 5.9 | 0.8 | 4.5 |
| 0.85 | 2.6 | 0.85 | 2.8 | 0.85 | 5.6 | 0.85 | 5.4 | 0.85 | 4.2 |
| 0.9 | 2.3 | 0.9 | 2.5 | 0.9 | 4.8 | 0.9 | 4.6 | 0.9 | 3.6 |
| 0.95 | 1.8 | 0.95 | 1.9 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

HF-HCFO-1233xf-HCFO-1233zdE-HFO-1234zeE-HFO-1243zf

| Organics 0.9 F1233xf + 0.033 F1234zeE + 0.033 F1233zdE + 0.034 F1243zf | | Organics 0.033 F1233xf + 0.9 F1234zeE + 0.033 F1233zdE + 0.034 F1243zf | | Organics 0.033 F1233xf + 0.033 F1234zeE + 0.9 F1233zdE + 0.034 F1243zf | | Organics 0.034 F1233xf + 0.033 F1234zeE + 0.033 F1233zdE + 0.9 F1243zf | | Organics 0.25 F1233xf + 0.25 1234zeE + 0.25 F1233zdE + 0.25 F1243zf | |
|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.6 | 0.1 | 4.7 |
| 0.15 | 3.0 | 0.15 | 5.7 | 0.15 | 2.8 | 0.15 | 6.6 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.8 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |

HF-HCFO-1233xf-HCFO-1233zdE-HFO-1234zeZ-HFO-1243zf

| Organics 0.9 F1233xf + 0.033 F1234zeZ + 0.033 F1233zdE + 0.034 F1243zf | | Organics 0.033 F1233xf + 0.9 F1234zeZ + 0.033 F1233zdE + 0.034 F1243zf | | Organics 0.033 F1233xf + 0.033 F1234zeZ + 0.9 F1233zdE + 0.034 F1243zf | | Organics 0.034 F1233xf + 0.033 F1234zeZ + 0.033 F1233zdE + 0.9 F1243zf | | Organics 0.25 F1233xf + 0.25 F1234zeZ + 0.25 F1233zdE + 0.25 F1243zf | |
|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

HF-HCFO-1233xf-HFO-1234zeE-HFO-1234zeZ-HFO-1243zf

| Organics 0.9 F1233xf + 0.033 F1234zeE + 0.033 F1234zeZ + 0.034 F1243zf | | Organics 0.033 F1233xf + 0.9 F1234zeE + 0.033 F1234zeZ + 0.034 F1243zf | | Organics 0.033 F1233xf + 0.033 F1234zeE + 0.9 F1234zeZ + 0.034 F1243zf | | Organics 0.034 F1233xf + 0.033 F1234zeE + 0.033 F1234zeZ + 0.9 F1243zf | | Organics 0.25 F1233xf + 0.25 F1234zeE + 0.25 F1234zeZ + 0.25 F1243zf | |
|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 1.9 | 0 | 4.7 | 0 | 2.1 | 0 | 5.6 | 0 | 3.7 |
| 0.05 | 3.0 | 0.05 | 5.7 | 0.05 | 3.2 | 0.05 | 6.5 | 0.05 | 4.7 |
| 0.1 | 3.0 | 0.1 | 5.7 | 0.1 | 3.2 | 0.1 | 6.6 | 0.1 | 4.7 |
| 0.15 | 3.0 | 0.15 | 5.7 | 0.15 | 3.2 | 0.15 | 6.6 | 0.15 | 4.7 |
| 0.2 | 3.0 | 0.2 | 5.7 | 0.2 | 3.2 | 0.2 | 6.5 | 0.2 | 4.7 |
| 0.25 | 3.0 | 0.25 | 5.7 | 0.25 | 3.2 | 0.25 | 6.5 | 0.25 | 4.7 |
| 0.3 | 3.0 | 0.3 | 5.7 | 0.3 | 3.2 | 0.3 | 6.5 | 0.3 | 4.7 |
| 0.35 | 3.0 | 0.35 | 5.7 | 0.35 | 3.2 | 0.35 | 6.5 | 0.35 | 4.7 |
| 0.4 | 3.0 | 0.4 | 5.7 | 0.4 | 3.2 | 0.4 | 6.5 | 0.4 | 4.7 |
| 0.45 | 3.0 | 0.45 | 5.7 | 0.45 | 3.2 | 0.45 | 6.5 | 0.45 | 4.7 |
| 0.5 | 3.0 | 0.5 | 5.6 | 0.5 | 3.2 | 0.5 | 6.5 | 0.5 | 4.7 |
| 0.55 | 2.9 | 0.55 | 5.6 | 0.55 | 3.1 | 0.55 | 6.5 | 0.55 | 4.6 |
| 0.6 | 2.9 | 0.6 | 5.5 | 0.6 | 3.1 | 0.6 | 6.5 | 0.6 | 4.6 |
| 0.65 | 2.9 | 0.65 | 5.4 | 0.65 | 3.1 | 0.65 | 6.4 | 0.65 | 4.6 |
| 0.7 | 2.9 | 0.7 | 5.3 | 0.7 | 3.1 | 0.7 | 6.3 | 0.7 | 4.5 |
| 0.75 | 2.9 | 0.75 | 5.0 | 0.75 | 3.1 | 0.75 | 6.2 | 0.75 | 4.4 |
| 0.8 | 2.8 | 0.8 | 4.7 | 0.8 | 3.0 | 0.8 | 5.9 | 0.8 | 4.1 |
| 0.85 | 2.6 | 0.85 | 4.2 | 0.85 | 2.7 | 0.85 | 5.4 | 0.85 | 3.8 |
| 0.0 | 2.2 | 0.9 | 3.5 | 0.9 | 2.1 | 0.9 | 4.6 | 0.9 | 3.2 |
| 0.95 | 1.8 | 0.95 | 2.5 | 0.95 | 1.9 | 0.95 | 3.3 | 0.95 | 2.4 |
| 1 | 1.2 | 1 | 1.2 | 1 | 1.2 | 1 | 1.2 | 1 | 1.2 |

HF-HCFO-1233xf-HFC-245cb-HFO-1234yf-HFO-1243zf

| Organics 0.9 F1233xf + 0.033 F1234yf + 0.033 F245cb + 0.034 F1243zf | | Organics 0.033 F1233xf + 0.9 F1234yf + 0.033 F245cb + 0.034 F1243zf | | Organics 0.033 F1233xf + 0.033 F1234yf + 0.9 F245cb + 0.034 F1243zf | | Organics 0.034 F1233xf + 0.033 F1234yf + 0.033 F245cb + 0.9 F1243zf | | Organics 0.25 F1233xf + 0.25 F1234yf + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 2.0 | 0 | 6.5 | 0 | 4.7 | 0 | 5.7 | 0 | 4.8 |
| 0.05 | 3.2 | 0.05 | 7.5 | 0.05 | 5.8 | 0.05 | 6.7 | 0.05 | 5.9 |
| 0.1 | 3.2 | 0.1 | 7.5 | 0.1 | 5.9 | 0.1 | 6.7 | 0.1 | 5.9 |
| 0.15 | 3.2 | 0.15 | 7.5 | 0.15 | 5.9 | 0.15 | 6.7 | 0.15 | 5.9 |
| 0.2 | 3.2 | 0.2 | 7.5 | 0.2 | 5.9 | 0.2 | 6.7 | 0.2 | 5.9 |
| 0.25 | 3.2 | 0.25 | 7.5 | 0.25 | 5.9 | 0.25 | 6.7 | 0.25 | 5.9 |
| 0.3 | 3.2 | 0.3 | 7.5 | 0.3 | 5.9 | 0.3 | 6.7 | 0.3 | 5.9 |
| 0.35 | 3.2 | 0.35 | 7.5 | 0.35 | 5.9 | 0.35 | 6.7 | 0.35 | 5.9 |
| 0.4 | 3.2 | 0.4 | 7.5 | 0.4 | 5.9 | 0.4 | 6.7 | 0.4 | 5.9 |
| 0.45 | 3.2 | 0.45 | 7.5 | 0.45 | 5.9 | 0.45 | 6.7 | 0.45 | 5.9 |
| 0.5 | 3.1 | 0.5 | 7.5 | 0.5 | 5.9 | 0.5 | 6.7 | 0.5 | 5.9 |
| 0.55 | 3.1 | 0.55 | 7.5 | 0.55 | 5.9 | 0.55 | 6.7 | 0.55 | 5.9 |
| 0.6 | 3.1 | 0.6 | 7.5 | 0.6 | 5.9 | 0.6 | 6.6 | 0.6 | 5.9 |
| 0.65 | 3.1 | 0.65 | 7.5 | 0.65 | 5.9 | 0.65 | 6.6 | 0.65 | 5.9 |
| 0.7 | 3.1 | 0.7 | 7.5 | 0.7 | 5.9 | 0.7 | 6.5 | 0.7 | 5.9 |
| 0.75 | 3.1 | 0.75 | 7.4 | 0.75 | 5.9 | 0.75 | 6.3 | 0.75 | 5.9 |
| 0.8 | 3.0 | 0.8 | 7.0 | 0.8 | 5.9 | 0.8 | 6.1 | 0.8 | 5.6 |
| 0.85 | 2.7 | 0.85 | 6.5 | 0.85 | 5.8 | 0.85 | 5.6 | 0.85 | 5.2 |
| 0.9 | 2.4 | 0.9 | 5.4 | 0.9 | 5.0 | 0.9 | 4.7 | 0.9 | 4.4 |
| 0.95 | 1.9 | 0.95 | 3.8 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

HF-HCFO-1233xf-HFO-1234yf-HFO-1234zeE-HFO-1243zf

| Organics 0.9 F1233xf + 0.033 F1234zeE + 0.033 F1243zf + 0.034 F1234yf | | Organics 0.033 F1233xf + 0.9 F1234zeE + 0.033 F1243zf + 0.034 F1234yf | | Organics 0.033 F1233xf + 0.033 F1234zeE + 0.9 F1243zf + 0.034 F1234yf | | Organics 0.034 F1233xf + 0.033 F1234zeE + 0.033 F1243zf + 0.9 F1234yf | | Organics 0.25 F1233xf + 0.25 F1234zeE + 0.25 F1243zf + 0.25 F1234yf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 2.1 | 0 | 4.9 | 0 | 5.7 | 0 | 6.5 | 0 | 4.9 |
| 0.05 | 3.2 | 0.05 | 5.8 | 0.05 | 6.7 | 0.05 | 7.5 | 0.05 | 5.9 |
| 0.1 | 3.2 | 0.1 | 5.9 | 0.1 | 6.7 | 0.1 | 7.5 | 0.1 | 5.9 |
| 0.15 | 3.2 | 0.15 | 5.9 | 0.15 | 6.7 | 0.15 | 7.5 | 0.15 | 5.9 |
| 0.2 | 3.2 | 0.2 | 5.9 | 0.2 | 6.7 | 0.2 | 7.5 | 0.2 | 5.9 |
| 0.25 | 3.2 | 0.25 | 5.9 | 0.25 | 6.7 | 0.25 | 7.5 | 0.25 | 5.9 |
| 0.3 | 3.2 | 0.3 | 5.9 | 0.3 | 6.7 | 0.3 | 7.5 | 0.3 | 5.9 |
| 0.35 | 3.2 | 0.35 | 5.9 | 0.35 | 6.7 | 0.35 | 7.5 | 0.35 | 5.9 |
| 0.4 | 3.1 | 0.4 | 5.8 | 0.4 | 6.7 | 0.4 | 7.5 | 0.4 | 5.9 |
| 0.45 | 3.1 | 0.45 | 5.8 | 0.45 | 6.7 | 0.45 | 7.5 | 0.45 | 5.9 |
| 0.5 | 3.1 | 0.5 | 5.8 | 0.5 | 6.7 | 0.5 | 7.5 | 0.5 | 5.9 |
| 0.55 | 3.1 | 0.55 | 5.8 | 0.55 | 6.7 | 0.55 | 7.5 | 0.55 | 5.9 |
| 0.6 | 3.1 | 0.6 | 5.7 | 0.6 | 6.6 | 0.6 | 7.5 | 0.6 | 5.9 |
| 0.65 | 3.1 | 0.65 | 5.6 | 0.65 | 6.6 | 0.65 | 7.5 | 0.65 | 5.8 |
| 0.7 | 3.1 | 0.7 | 5.4 | 0.7 | 6.5 | 0.7 | 7.5 | 0.7 | 5.7 |
| 0.75 | 3.1 | 0.75 | 5.2 | 0.75 | 6.3 | 0.75 | 7.3 | 0.75 | 5.6 |
| 0.8 | 2.9 | 0.8 | 4.9 | 0.8 | 6.0 | 0.8 | 7.0 | 0.8 | 5.3 |
| 0.85 | 2.7 | 0.85 | 4.4 | 0.85 | 5.5 | 0.85 | 6.4 | 0.85 | 4.8 |
| 0.9 | 2.4 | 0.9 | 3.6 | 0.9 | 4.7 | 0.9 | 5.4 | 0.9 | 4.0 |
| 0.95 | 1.9 | 0.95 | 2.6 | 0.95 | 3.3 | 0.95 | 3.7 | 0.95 | 2.9 |
| 1 | 1.2 | 1 | 1.2 | 1 | 1.2 | 1 | 1.2 | 1 | 1.2 |

HF-HCFO-1233xf-HFO-1234yf-HFO-1234zeZ-HFO-1243zf

| Organics 0.9 F1233xf + 0.033 F1234zeZ + 0.033 F1243zf + 0.034 F1234yf | | Organics 0.033 F1233xf + 0.9 F1234zeZ + 0.033 F1243zf + 0.034 F1234yf | | Organics 0.033 F1233xf + 0.033 F1234zeZ + 0.9 F1243zf + 0.034 F1234yf | | Organics 0.034 F1233xf + 0.033 F1234zeZ + 0.033 F1243zf + 0.9 F1234yf | | Organics 0.25 F1233xf + 0.25 F1234zeZ + 0.25 F1243zf + 0.25 F1234yf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 1.9 | 0 | 2.1 | 0 | 5.6 | 0 | 6.4 | 0 | 4.1 |
| 0.05 | 3.1 | 0.05 | 3.2 | 0.05 | 6.6 | 0.05 | 7.4 | 0.05 | 5.2 |
| 0.1 | 3.1 | 0.1 | 3.2 | 0.1 | 6.6 | 0.1 | 7.4 | 0.1 | 5.2 |
| 0.15 | 3.1 | 0.15 | 3.2 | 0.15 | 6.6 | 0.15 | 7.4 | 0.15 | 5.2 |
| 0.2 | 3.1 | 0.2 | 3.2 | 0.2 | 6.6 | 0.2 | 7.4 | 0.2 | 5.2 |
| 0.25 | 3.1 | 0.25 | 3.2 | 0.25 | 6.6 | 0.25 | 7.4 | 0.25 | 5.2 |
| 0.3 | 3.1 | 0.3 | 3.2 | 0.3 | 6.6 | 0.3 | 7.4 | 0.3 | 5.2 |
| 0.35 | 3.0 | 0.35 | 3.2 | 0.35 | 6.6 | 0.35 | 7.4 | 0.35 | 5.2 |
| 0.4 | 3.0 | 0.4 | 3.2 | 0.4 | 6.6 | 0.4 | 7.4 | 0.4 | 5.2 |
| 0.45 | 3.0 | 0.45 | 3.2 | 0.45 | 6.6 | 0.45 | 7.4 | 0.45 | 5.2 |
| 0.5 | 3.0 | 0.5 | 3.2 | 0.5 | 6.6 | 0.5 | 7.4 | 0.5 | 5.2 |
| 0.55 | 3.0 | 0.55 | 3.2 | 0.55 | 6.6 | 0.55 | 7.4 | 0.55 | 5.2 |
| 0.5 | 3.0 | 0.6 | 3.2 | 0.6 | 6.5 | 0.6 | 7.4 | 0.6 | 5.2 |
| 0.65 | 3.0 | 0.65 | 3.2 | 0.65 | 6.5 | 0.65 | 7.4 | 0.65 | 5.2 |
| 0.7 | 3.0 | 0.7 | 3.2 | 0.7 | 6.4 | 0.7 | 7.4 | 0.7 | 5.1 |
| 0.75 | 3.0 | 0.75 | 3.2 | 0.75 | 6.2 | 0.75 | 7.2 | 0.75 | 5.0 |
| 0.8 | 2.9 | 0.8 | 3.1 | 0.8 | 6.0 | 0.8 | 6.9 | 0.8 | 4.8 |
| 0.85 | 2.6 | 0.85 | 2.8 | 0.85 | 5.5 | 0.85 | 6.3 | 0.85 | 4.4 |
| 0.9 | 2.3 | 0.9 | 2.5 | 0.9 | 4.6 | 0.9 | 5.3 | 0.9 | 3.7 |
| 0.95 | 1.8 | 0.95 | 2.0 | 0.95 | 3.3 | 0.95 | 3.7 | 0.95 | 2.7 |
| 1 | 1.2 | 1 | 1.2 | 1 | 1.2 | 1 | 1.2 | 1 | 1.2 |

HF-HCFO-1233xf-HFO-1234yf-HCFO-1233zdE-HFO-1243zf

| Organics 0.9 F1233xf + 0.033 F1243zf + 0.033 F1233zdE + 0.034 F1234yf | | Organics 0.033 F1233xf + 0.9 F1243zf + 0.033 F1233zdE + 0.034 F1234yf | | Organics 0.033 F1233xf + 0.033 F1243zf + 0.9 F1233zdE + 0.034 F1234yf | | Organics 0.034 F1233xf + 0.033 F1243zf + 0.033 F1233zdE + 0.9 F1234yf | | Organics 0.25 F1233xf + 0.25 F1243zf + 0.25 F1233zdE + 0.25 F1234yf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 1.9 | 0 | 5.6 | 0 | 1.7 | 0 | 6.4 | 0 | 4.1 |
| 0.05 | 3.0 | 0.05 | 6.6 | 0.05 | 2.8 | 0.05 | 7.4 | 0.05 | 5.2 |
| 0.1 | 3.0 | 0.1 | 6.6 | 0.1 | 2.8 | 0.1 | 7.4 | 0.1 | 5.2 |
| 0.15 | 3.0 | 0.15 | 6.6 | 0.15 | 2.8 | 0.15 | 7.4 | 0.15 | 5.2 |
| 0.2 | 3.0 | 0.2 | 6.6 | 0.2 | 2.8 | 0.2 | 7.4 | 0.2 | 5.2 |
| 0.25 | 3.0 | 0.25 | 6.6 | 0.25 | 2.8 | 0.25 | 7.4 | 0.25 | 5.2 |
| 0.3 | 3.0 | 0.3 | 6.6 | 0.3 | 2.8 | 0.3 | 7.4 | 0.3 | 5.2 |
| 0.35 | 3.0 | 0.35 | 6.6 | 0.35 | 2.8 | 0.35 | 7.4 | 0.35 | 5.2 |
| 0.4 | 3.0 | 0.4 | 6.6 | 0.4 | 2.8 | 0.4 | 7.4 | 0.4 | 5.2 |
| 0.45 | 3.0 | 0.45 | 6.6 | 0.45 | 2.8 | 0.45 | 7.4 | 0.45 | 5.2 |
| 0.5 | 3.0 | 0.5 | 6.6 | 0.5 | 2.8 | 0.5 | 7.4 | 0.5 | 5.1 |
| 0.55 | 3.0 | 0.55 | 6.6 | 0.55 | 2.8 | 0.55 | 7.4 | 0.55 | 5.1 |
| 0.6 | 3.0 | 0.6 | 6.5 | 0.6 | 2.8 | 0.6 | 7.4 | 0.6 | 5.1 |
| 0.65 | 3.0 | 0.65 | 6.5 | 0.65 | 2.8 | 0.65 | 7.4 | 0.65 | 5.1 |
| 0.7 | 3.0 | 0.7 | 6.4 | 0.7 | 2.8 | 0.7 | 7.4 | 0.7 | 5.1 |
| 0.75 | 3.0 | 0.75 | 6.2 | 0.75 | 2.8 | 0.75 | 7.2 | 0.75 | 4.9 |
| 0.8 | 2.8 | 0.8 | 6.0 | 0.8 | 2.7 | 0.8 | 6.9 | 0.8 | 4.7 |
| 0.85 | 2.6 | 0.85 | 5.5 | 0.85 | 2.5 | 0.85 | 6.3 | 0.85 | 4.3 |
| 0.9 | 2.3 | 0.9 | 4.6 | 0.9 | 2.2 | 0.9 | 5.3 | 0.9 | 3.7 |
| 0.95 | 1.8 | 0.95 | 3.3 | 0.95 | 1.8 | 0.95 | 3.7 | 0.95 | 2.7 |
| 1 | 1.2 | 1 | 1.2 | 1 | 1.2 | 1 | 1.2 | 1 | 1.2 |

HF-HFO-1234yf-HFO-1234zeE-HFO-1234zeZ-HFO-1243zf

| Organics 0.9 F1234yf + 0.033 F1234zeZ + 0.033 F1234zeE + 0.034 F1243zf | | Organics 0.033 F1234yf + 0.9 F1234zeZ + 0.033 F1234zeE + 0.034 F1243zf | | Organics 0.033 F1234yf + 0.033 F1234zeZ + 0.9 F1234zeE + 0.034 F1243zf | | Organics 0.034 F1234yf + 0.033 F1234zeZ + 0.033 F1234zeE + 0.9 F1243zf | | Organics 0.25 F1234yf + 0.25 F1234zeZ + 0.25 F1234zeE + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 2.2 | 0 | 4.9 | 0 | 5.7 | 0 | 4.9 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.9 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.7 | 0.6 | 6.6 | 0.6 | 5.9 |
| 0.65 | 7.5 | 0.65 | 3.3 | 0.65 | 5.6 | 0.65 | 6.6 | 0.65 | 5.8 |
| 0.7 | 7.5 | 0.7 | 3.3 | 0.7 | 5.4 | 0.7 | 6.5 | 0.7 | 5.7 |
| 0.75 | 7.3 | 0.75 | 3.3 | 0.75 | 5.2 | 0.75 | 6.3 | 0.75 | 5.6 |
| 0.8 | 7.0 | 0.8 | 3.1 | 0.8 | 4.9 | 0.8 | 6.0 | 0.8 | 5.3 |
| 0.85 | 6.4 | 0.85 | 2.9 | 0.85 | 4.4 | 0.85 | 5.6 | 0.85 | 4.8 |
| 0.9 | 5.4 | 0.9 | 2.5 | 0.9 | 3.7 | 0.9 | 4.7 | 0.9 | 4.1 |
| 0.95 | 3.7 | 0.95 | 2.0 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeE-HCFO-1233zdE-HFO-1243zf

| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1243zf | | Organics 0.033 F1234yf + 0.033 F1233zdE + 0.9 F1234zeE + 0.034 F1243zf | | Organics 0.034 F1234yf + 0.033 F1233zdE + 0.033 F1234zeE + 0.9 F1243zf | | Organics 0.25 F1234yf + 0.25 F1233zdE + 0.25 F1234zeE + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.0 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

HF-HFO-1234yf-HFO-1234zeZ-HCFO-1233zdE-HFO-1243zf

| Organics 0.9 F1234yf + 0.033 F1233zdE + 0.033 F1234zeZ + 0.034 F1243zf | | Organics 0.033 F1234yf + 0.9 F1233zdE + 0.033 F1234zeZ + 0.034 F1243zf | | Organics 0.033 F1234yf + 0.033 F1233zdE + 0.9 F1234zeZ + 0.034 F1243zf | | Organics 0.034 F1234yf + 0.033 F1233zdE + 0.033 F1234zeZ + 0.9 F1243zf | | Organics 0.25 F1234yf + 0.25 F1233zdE + 0.25 F1234zeZ + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1243zf

| Organics 0.9 F1234yf + 0.033 F1234zeE + 0.033 F245cb + 0.034 F1243zf | | Organics 0.033 F1234yf + 0.9 F1234zeE + 0.033 F245cb + 0.034 F1243zf | | Organics 0.033 F1234yf + 0.033 F1234zeE + 0.09 F245cb + 0.034 F1243zf | | Organics 0.034 F1234yf + 0.033 F1234zeE + 0.033 F245cb + 0.09 F1243zf | | Organics 0.25 F1234yf + 0.25 F1234zeE + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.6 | 0 | 5.0 | 0 | 4.8 | 0 | 5.8 | 0 | 5.6 |
| 0.05 | 7.6 | 0.05 | 5.9 | 0.05 | 6.0 | 0.05 | 6.8 | 0.05 | 6.6 |
| 0.1 | 7.6 | 0.1 | 6.0 | 0.1 | 6.0 | 0.1 | 6.8 | 0.1 | 6.6 |
| 0.15 | 7.6 | 0.15 | 6.0 | 0.15 | 6.0 | 0.15 | 6.8 | 0.15 | 6.6 |
| 0.2 | 7.6 | 0.2 | 6.0 | 0.2 | 6.0 | 0.2 | 6.8 | 0.2 | 6.6 |
| 0.25 | 7.6 | 0.25 | 6.0 | 0.25 | 6.0 | 0.25 | 6.8 | 0.25 | 6.6 |
| 0.3 | 7.6 | 0.3 | 6.0 | 0.3 | 6.0 | 0.3 | 6.8 | 0.3 | 6.6 |
| 0.35 | 7.6 | 0.35 | 6.0 | 0.35 | 6.0 | 0.35 | 6.8 | 0.35 | 6.6 |
| 0.4 | 7.6 | 0.4 | 6.0 | 0.4 | 6.0 | 0.4 | 6.8 | 0.4 | 6.6 |
| 0.45 | 7.6 | 0.45 | 5.9 | 0.45 | 6.0 | 0.45 | 6.8 | 0.45 | 6.6 |
| 0.5 | 7.6 | 0.5 | 5.9 | 0.5 | 6.0 | 0.5 | 6.8 | 0.5 | 6.6 |
| 0.55 | 7.6 | 0.55 | 5.9 | 0.55 | 6.0 | 0.55 | 6.7 | 0.55 | 6.6 |
| 0.6 | 7.6 | 0.6 | 5.8 | 0.6 | 6.0 | 0.6 | 6.7 | 0.6 | 6.6 |
| 0.65 | 7.6 | 0.65 | 5.7 | 0.65 | 5.9 | 0.65 | 6.7 | 0.65 | 6.6 |
| 0.7 | 7.6 | 0.7 | 5.6 | 0.7 | 5.9 | 0.7 | 6.6 | 0.7 | 6.6 |
| 0.75 | 7.4 | 0.75 | 5.3 | 0.75 | 5.9 | 0.75 | 6.4 | 0.75 | 6.4 |
| 0.8 | 7.1 | 0.8 | 5.0 | 0.8 | 5.9 | 0.8 | 6.1 | 0.8 | 6.1 |
| 0.85 | 6.5 | 0.85 | 4.5 | 0.85 | 5.8 | 0.85 | 5.6 | 0.85 | 5.6 |
| 0.9 | 5.5 | 0.9 | 3.7 | 0.9 | 5.0 | 0.9 | 4.8 | 0.9 | 4.8 |
| 0.95 | 3.8 | 0.95 | 2.7 | 0.95 | 3.5 | 0.95 | 3.4 | 0.95 | 3.4 |
| 1 | 1.2 | 1 | 1.2 | 1 | 1.2 | 1 | 1.2 | 1 | 1.2 |

HF-HFO-1234yf-HFC-245cb-HFO-1234zeZ-HFO-1243zf

| Organics 0.9 F1234yf + 0.033 F1234zeZ + 0.033 F245cb + 0.034 F1243zf | | Organics 0.033 F1234yf + 0.9 F1234zeZ + 0.033 F245cb + 0.034 F1243zf | | Organics 0.033 F1234yf + 0.033 F1234zeZ + 0.9 F245cb + 0.034 F1243zf | | Organics 0.034 F1234yf + 0.033 F1234zeZ + 0.033 F245cb + 0.9 F1243zf | | Organics 0.25 F1234yf + 0.25 F1234zeZ + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 2.2 | 0 | 4.7 | 0 | 5.7 | 0 | 4.8 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.8 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.8 | 0.6 | 6.6 | 0.6 | 5.9 |
| 0.65 | 7.5 | 0.65 | 3.3 | 0.65 | 5.8 | 0.65 | 6.6 | 0.65 | 5.9 |
| 0.7 | 7.5 | 0.7 | 3.3 | 0.7 | 5.9 | 0.7 | 6.5 | 0.7 | 5.9 |
| 0.75 | 7.3 | 0.75 | 3.3 | 0.75 | 5.9 | 0.75 | 6.3 | 0.75 | 5.9 |
| 0.8 | 7.0 | 0.8 | 3.2 | 0.8 | 5.9 | 0.8 | 6.1 | 0.8 | 5.6 |
| 0.85 | 6.5 | 0.85 | 2.9 | 0.85 | 5.8 | 0.85 | 5.6 | 0.85 | 5.2 |
| 0.9 | 5.4 | 0.9 | 2.6 | 0.9 | 5.0 | 0.9 | 4.7 | 0.9 | 4.4 |
| 0.95 | 3.8 | 0.95 | 2.0 | 0.95 | 3.5 | 0.95 | 3.4 | 0.95 | 3.2 |
| 1 | 1.2 | 1 | 1.2 | 1 | 1.2 | 1 | 1.2 | 1 | 1.2 |

HF-HFO-1234yf-HFC-245cb-HCFO-1233zdE-HFO-1243zf

| Organics 0.9 F1234yf + 0.033 F1233zdE + 0.033 F245cb + 0.034 F1243zf | | Organics 0.033 F1234yf + 0.9 F1233zdE + 0.033 F245cb + 0.034 F1243zf | | Organics 0.033 F1234yf + 0.033 F1233zdE + 0.9 F245cb + 0.034 F1243zf | | Organics 0.034 F1234yf + 0.033 F1233zdE + 0.033 F245cb + 0.9 F1243zf | | Organics 0.25 F1234yf + 0.25 F1233zdE + 0.25 F245cb + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 6.5 | 0 | 1.8 | 0 | 4.7 | 0 | 5.7 | 0 | 4.8 |
| 0.05 | 7.5 | 0.05 | 2.9 | 0.05 | 5.8 | 0.05 | 6.7 | 0.05 | 5.9 |
| 0.1 | 7.5 | 0.1 | 2.9 | 0.1 | 5.8 | 0.1 | 6.7 | 0.1 | 5.9 |
| 0.15 | 7.5 | 0.15 | 2.9 | 0.15 | 5.8 | 0.15 | 6.7 | 0.15 | 5.9 |
| 0.2 | 7.5 | 0.2 | 2.9 | 0.2 | 5.8 | 0.2 | 6.7 | 0.2 | 5.9 |
| 0.25 | 7.5 | 0.25 | 2.9 | 0.25 | 5.8 | 0.25 | 6.7 | 0.25 | 5.9 |
| 0.3 | 7.5 | 0.3 | 2.9 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.9 |
| 0.55 | 7.5 | 0.55 | 2.9 | 0.55 | 5.8 | 0.55 | 6.7 | 0.55 | 5.9 |
| 0.6 | 7.5 | 0.6 | 2.9 | 0.6 | 5.8 | 0.6 | 6.6 | 0.6 | 5.9 |
| 0.65 | 7.5 | 0.65 | 2.9 | 0.65 | 5.8 | 0.55 | 6.6 | 0.65 | 5.9 |
| 0.7 | 7.5 | 0.7 | 2.9 | 0.7 | 5.8 | 0.7 | 6.5 | 0.7 | 5.9 |
| 0.75 | 7.3 | 0.75 | 2.9 | 0.75 | 5.8 | 0.75 | 6.3 | 0.75 | 5.8 |
| 0.8 | 7.0 | 0.8 | 2.8 | 0.8 | 5.8 | 0.8 | 6.1 | 0.8 | 5.6 |
| 0.85 | 6.5 | 0.85 | 2.6 | 0.85 | 5.8 | 0.85 | 5.6 | 0.85 | 5.1 |
| 0.9 | 5.4 | 0.9 | 2.3 | 0.9 | 5.0 | 0.9 | 4.7 | 0.9 | 4.4 |
| 0.95 | 3.8 | 0.95 | 1.3 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1243zf

| Organics 0.9 F245cb + 0.033 F1234zeE + 0.033 F1233zdE + 0.034 F1243zf | | Organics 0.033 F245cb + 0.9 F1234zeE + 0.033 F1233zdE + 0.033 F1243zf | | Organics 0.033 F245cb + 0.033 F1234zeE + 0.9 F1233zdE + 0.034 F1243zf | | Organics 0.034 F245cb + 0.033 F1234zeE + 0.033 F1233zdE + 0.9 F1243zf | | Organics 0.25 F245cb + 0.25 F1234zeE + 0.25 F1233zdE + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.6 | 0 | 4.8 | 0 | 1.8 | 0 | 5.7 | 0 | 4.3 |
| 0.05 | 5.8 | 0.05 | 5.8 | 0.05 | 2.9 | 0.05 | 6.6 | 0.05 | 5.4 |
| 0.1 | 5.8 | 0.1 | 5.8 | 0.1 | 2.9 | 0.1 | 6.6 | 0.1 | 5.4 |
| 0.15 | 5.8 | 0.15 | 5.8 | 0.15 | 2.9 | 0.15 | 6.6 | 0.15 | 5.4 |
| 0.2 | 5.8 | 0.2 | 5.8 | 0.2 | 2.9 | 0.2 | 6.6 | 0.2 | 5.4 |
| 0.25 | 5.8 | 0.25 | 5.8 | 0.25 | 2.9 | 0.25 | 6.6 | 0.25 | 5.4 |
| 0.3 | 5.8 | 0.3 | 5.8 | 0.3 | 2.9 | 0.3 | 6.6 | 0.3 | 5.4 |
| 0.35 | 5.8 | 0.35 | 5.8 | 0.35 | 2.9 | 0.35 | 6.6 | 0.35 | 5.4 |
| 0.4 | 5.8 | 0.4 | 5.8 | 0.4 | 2.9 | 0.4 | 6.6 | 0.4 | 5.4 |
| 0.45 | 5.8 | 0.45 | 5.8 | 0.45 | 2.9 | 0.45 | 6.6 | 0.45 | 5.4 |
| 0.5 | 5.8 | 0.5 | 5.7 | 0.5 | 2.9 | 0.5 | 6.6 | 0.5 | 5.4 |
| 0.55 | 5.8 | 0.55 | 5.7 | 0.55 | 2.9 | 0.55 | 6.6 | 0.55 | 5.4 |
| 0.6 | 5.8 | 0.6 | 5.6 | 0.6 | 2.9 | 0.6 | 6.6 | 0.6 | 5.4 |
| 0.65 | 5.8 | 0.65 | 5.5 | 0.65 | 2.8 | 0.65 | 6.5 | 0.65 | 5.4 |
| 0.7 | 5.8 | 0.7 | 5.4 | 0.7 | 2.8 | 0.7 | 6.4 | 0.7 | 5.4 |
| 0.75 | 5.8 | 0.75 | 5.2 | 0.75 | 5.8 | 0.75 | 6.3 | 0.75 | 5.2 |
| 0.8 | 5.8 | 0.8 | 4.8 | 0.8 | 2.7 | 0.8 | 6.0 | 0.8 | 5.0 |
| 0.85 | 5.7 | 0.85 | 4.3 | 0.85 | 2.5 | 0.85 | 5.5 | 0.85 | 4.5 |
| 0.9 | 4.9 | 0.9 | 3.6 | 0.9 | 2.2 | 0.9 | 4.7 | 0.9 | 3.9 |
| 0.95 | 3.5 | 0.95 | 2.6 | 0.95 | 1.8 | 0.95 | 3.3 | 0.95 | 2.8 |
| 1 | 1.2 | 1 | 1.2 | 1 | 1.2 | 1 | 1.2 | 1 | 1.2 |

HF-HFC-245cb-HCFO-1233zdE-HFO-1234zeZ-HFO-1243zf

| Organics 0.9 F245cb + 0.033 F1234zeZ + 0.033 F1233zdE + 0.034 F1243zf | | Organics 0.033 F245cb + 0.9 F1234zeZ + 0.033 F1233zdE + 0.034 F1243zf | | Organics 0.033 F245cb + 0.033 F1234zeZ + 0.9 F1233zdE + 0.034 F1243zf | | Organics 0.034 F245cb + 0.033 F1234zeZ + 0.033 F1233zdE + 0.9 F1243zf | | Organics 0.25 F245cb + 0.25 F1234zeZ + 0.25 F1233zdE + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.5 | 0 | 2.0 | 0 | 1.7 | 0 | 5.6 | 0 | 3.5 |
| 0.05 | 5.7 | 0.05 | 3.2 | 0.05 | 2.8 | 0.05 | 6.5 | 0.05 | 4.6 |
| 0.1 | 5.7 | 0.1 | 3.2 | 0.1 | 2.8 | 0.1 | 6.6 | 0.1 | 4.6 |
| 0.15 | 5.7 | 0.15 | 3.2 | 0.15 | 2.8 | 0.15 | 6.6 | 0.15 | 4.6 |
| 0.2 | 5.7 | 0.2 | 3.2 | 0.2 | 2.8 | 0.2 | 6.5 | 0.2 | 4.6 |
| 0.25 | 5.7 | 0.25 | 3.2 | 0.25 | 2.8 | 0.25 | 6.5 | 0.25 | 4.6 |
| 0.3 | 5.7 | 0.3 | 3.2 | 0.3 | 2.8 | 0.3 | 6.5 | 0.3 | 4.6 |
| 0.35 | 5.7 | 0.35 | 3.2 | 0.35 | 2.8 | 0.35 | 6.5 | 0.35 | 4.6 |
| 0.4 | 5.7 | 0.4 | 3.2 | 0.4 | 2.8 | 0.4 | 6.5 | 0.4 | 4.6 |
| 0.45 | 5.7 | 0.45 | 3.2 | 0.45 | 2.8 | 0.45 | 6.5 | 0.45 | 4.6 |
| 0.5 | 5.7 | 0.5 | 3.2 | 0.5 | 2.8 | 0.5 | 6.5 | 0.5 | 4.7 |
| 0.55 | 5.7 | 0.55 | 3.2 | 0.55 | 2.8 | 0.55 | 6.5 | 0.55 | 4.7 |
| 0.6 | 5.7 | 0.6 | 3.2 | 0.6 | 2.8 | 0.6 | 6.5 | 0.6 | 4.7 |
| 0.65 | 5.7 | 0.65 | 3.2 | 0.65 | 2.8 | 0.65 | 6.4 | 0.65 | 4.7 |
| 0.7 | 5.7 | 0.7 | 3.2 | 0.7 | 2.8 | 0.7 | 6.4 | 0.7 | 4.7 |
| 0.75 | 5.7 | 0.75 | 3.1 | 0.75 | 2.8 | 0.75 | 6.2 | 0.75 | 4.7 |
| 0.8 | 5.7 | 0.8 | 3.0 | 0.8 | 2.6 | 0.8 | 5.9 | 0.8 | 4.5 |
| 0.85 | 5.6 | 0.85 | 2.8 | 0.85 | 2.4 | 0.85 | 5.4 | 0.85 | 4.1 |
| 0.9 | 4.8 | 0.9 | 2.5 | 0.9 | 2.2 | 0.9 | 4.6 | 0.9 | 3.5 |
| 0.95 | 3.4 | 0.95 | 1.9 | 0.95 | 1.8 | 0.95 | 3.3 | 0.95 | 2.6 |
| 1 | 1.2 | 1 | 1.2 | 1 | 1.2 | 1 | 1.2 | 1 | 1.2 |

HF-HCFO-1233zdE-HFO-1234zeE-HFO-1234zeZ-HFO-1243zf

| Organics 0.9 F1234zeE + 0.033 F1234zeZ + 0.033 F1233zdE + 0.034 F1243zf | | Organics 0.033 F1234zeE + 0.9 F1234zeZ + 0.033 F1233zdE + 0.034 F1243zf | | Organics 0.033 F1234zeE + 0.033 F1234zeZ + 0.9 F1233zdE + 0.034 F1243zf | | Organics 0.034 F1234zeE + 0.033 F1234zeZ + 0.033 F1233zdE + 0.9 F1243zf | | Organics 0.25 F1234zeE + 0.25 F1234zeZ + 0.25 F1233zdE + 0.25 F1243zf | |
|---|---|---|---|---|---|---|---|---|---|
| MASS-FRAC HF | TOTAL PRES bar | MASS-FRAC HF | TOTAL PRES bar | MASS-FRAC HF | TOTAL PRES bar | MASS-FRAC HF | TOTAL PRES bar | MASS-FRAC HF | TOTAL PRES bar |
| 0 | 4.7 | 0 | 2.1 | 0 | 1.7 | 0 | 5.6 | 0 | 3.6 |
| 0.05 | 5.7 | 0.05 | 3.2 | 0.05 | 2.8 | 0.05 | 6.5 | 0.05 | 4.7 |
| 0.1 | 5.7 | 0.1 | 3.2 | 0.1 | 2.8 | 0.1 | 6.6 | 0.1 | 4.7 |
| 0.15 | 5.7 | 0.15 | 3.2 | 0.15 | 2.8 | 0.15 | 6.5 | 0.15 | 4.7 |
| 0.2 | 5.7 | 0.2 | 3.2 | 0.2 | 2.8 | 0.2 | 6.5 | 0.2 | 4.7 |
| 0.25 | 5.7 | 0.25 | 3.2 | 0.25 | 2.8 | 0.25 | 6.5 | 0.25 | 4.7 |
| 0.3 | 5.7 | 0.3 | 3.2 | 0.3 | 2.8 | 0.3 | 6.5 | 0.3 | 4.6 |
| 0.35 | 5.7 | 0.35 | 3.1 | 0.35 | 2.8 | 0.35 | 6.5 | 0.35 | 4.6 |
| 0.4 | 5.7 | 0.4 | 3.1 | 0.4 | 2.8 | 0.4 | 6.5 | 0.4 | 4.6 |
| 0.45 | 5.7 | 0.45 | 3.1 | 0.45 | 2.7 | 0.45 | 6.5 | 0.45 | 4.6 |
| 0.5 | 5.6 | 0.5 | 3.1 | 0.5 | 2.7 | 0.5 | 6.5 | 0.5 | 4.6 |
| 0.55 | 5.6 | 0.55 | 3.1 | 0.55 | 2.7 | 0.55 | 6.5 | 0.55 | 4.6 |
| 0.6 | 5.5 | 0.6 | 3.1 | 0.6 | 2.7 | 0.6 | 6.5 | 0.6 | 4.6 |
| 0.65 | 5.4 | 0.65 | 3.1 | 0.65 | 2.7 | 0.65 | 6.4 | 0.65 | 4.6 |
| 0.7 | 5.3 | 0.7 | 3.1 | 0.7 | 2.7 | 0.7 | 6.3 | 0.7 | 4.5 |
| 0.75 | 5.0 | 0.75 | 3.1 | 0.75 | 2.7 | 0.75 | 6.2 | 0.75 | 4.3 |
| 0.8 | 4.7 | 0.8 | 3.0 | 0.8 | 2.6 | 0.8 | 5.9 | 0.8 | 4.1 |
| 0.85 | 4.2 | 0.85 | 2.7 | 0.85 | 2.4 | 0.85 | 5.4 | 0.85 | 3.7 |
| 0.9 | 3.5 | 0.9 | 2.4 | 0.9 | 2.1 | 0.9 | 4.6 | 0.0 | 3.2 |
| 0.95 | 2.5 | 0.95 | 1.9 | 0.95 | 1.7 | 0.95 | 3.3 | 0.95 | 2.4 |
| 1 | 1.2 | 1 | 1.2 | 1 | 1.2 | 1 | 1.2 | 1 | 1.2 |

HF-HFC-245cb-HFO-1234zeE-HFO-1234zeZ-HFO-1243zf

| Organics 0.9 F245cb + 0.033 F1234zeE + 0.033 F1234zeZ + 0.034 F1243zf | | Organics 0.033 F245cb + 0.9 F1234zeE + 0.033 F1234zeZ + 0.034 F1243zf | | Organics 0.033 F245cb + 0.033 F1234zeE + 0.9 F1234zeZ + 0.034 F1243zf | | Organics 0.034 F245cb + 0.033 F1234zeE + 0.033 F1234zeZ + 0.9 F1243zf | | Organics 0.25 F245cb + 0.25 F1234zeE + 0.25 F1234zeZ + 0.25 F1243zf | |
|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.6 | 0 | 4.8 | 0 | 2.2 | 0 | 5.7 | 0 | 4.4 |
| 0.05 | 5.8 | 0.05 | 5.8 | 0.05 | 3.3 | 0.05 | 6.6 | 0.05 | 5.4 |
| 0.1 | 5.8 | 0.1 | 5.8 | 0.1 | 3.3 | 0.1 | 6.7 | 0.1 | 5.4 |
| 0.15 | 5.8 | 0.15 | 6.8 | 0.15 | 3.3 | 0.15 | 6.6 | 0.15 | 5.4 |
| 0.2 | 5.8 | 0.2 | 5.8 | 0.2 | 3.3 | 0.2 | 6.6 | 0.2 | 5.4 |
| 0.25 | 5.8 | 0.25 | 5.8 | 0.25 | 3.3 | 0.25 | 6.6 | 0.25 | 5.4 |
| 0.3 | 5.8 | 0.3 | 5.8 | 0.3 | 3.3 | 0.3 | 6.6 | 0.3 | 5.4 |
| 0.35 | 5.8 | 0.35 | 5.8 | 0.35 | 3.3 | 0.35 | 6.6 | 0.35 | 5.4 |
| 0.4 | 5.8 | 0.4 | 5.8 | 0.4 | 3.3 | 0.4 | 6.6 | 0.4 | 5.4 |
| 0.45 | 5.8 | 0.45 | 5.8 | 0.45 | 3.3 | 0.45 | 6.6 | 0.45 | 5.4 |
| 0.5 | 5.8 | 0.5 | 5.7 | 0.5 | 3.3 | 0.5 | 6.6 | 0.5 | 5.4 |
| 0.55 | 5.8 | 0.55 | 5.7 | 0.55 | 3.3 | 0.55 | 6.6 | 0.55 | 5.4 |
| 0.6 | 5.8 | 0.6 | 5.6 | 0.6 | 3.3 | 0.6 | 6.6 | 0.6 | 5.4 |
| 0.65 | 5.8 | 0.65 | 5.5 | 0.65 | 3.3 | 0.65 | 6.5 | 0.65 | 5.4 |
| 0.7 | 5.8 | 0.7 | 5.4 | 0.7 | 3.2 | 0.7 | 6.4 | 0.7 | 5.4 |
| 0.75 | 5.8 | 0.75 | 5.2 | 0.75 | 3.2 | 0.75 | 6.3 | 0.75 | 5.3 |
| 0.8 | 5.8 | 0.8 | 4.8 | 0.8 | 3.1 | 0.8 | 6.0 | 0.8 | 5.0 |
| 0.85 | 5.7 | 0.85 | 4.3 | 0.85 | 2.9 | 0.85 | 5.5 | 0.85 | 4.6 |
| 0.9 | 4.9 | 0.9 | 3.6 | 0.9 | 2.5 | 0.9 | 4.7 | 0.9 | 3.9 |
| 0.95 | 3.5 | 0.95 | 2.6 | 0.95 | 2.0 | 0.95 | 3.3 | 0.95 | 2.8 |
| 1 | 1.2 | 1 | 1.2 | 1 | 1.2 | 1 | 1.2 | 1 | 1.2 |

EXAMPLE 8: TEMPERATURE AND PRESSURE RANGE OF PENTERNARY MIXTURES

| System with 5 compounds | Boiling point range Temperature ° C. | Pressure bar abs |
|---|---|---|
| HF-HCFO-1233xf-HFC-245cb-HCFO-1233zdE-HFO-1243zf | 0 to 40 | ~1.0 to ~10.0 |
| HF-HCFO-1233xf-HFC-245cb-HFO-1234zeE-HFO-1243zf | 0 to 40 | ~1.0 to ~10.2 |
| HF-HCFO-1233xf-HFC-245cb-HFO-1234zeZ-HFO-1243zf | 0 to 40 | ~1.1 to ~10.1 |
| HF-HCFO-1233xf-HFC-245cb-HFO-1234yf-HFO-1243zf | 0 to 40 | ~1.2 to ~11.4 |
| HF-HCFO-1233xf-HFO-1234yf-HFO-1234zeE-HFO-1243zf | 0 to 40 | ~1.2 to ~11.4 |
| HF-HCFO-1233xf-HFO-1234yf-HFO-1234zeZ-HFO-1243zf | 0 to 40 | ~1.2 to ~11.2 |
| HF-HCFO-1233xf-HFO-1234yf-HCFO-1233zdE-HFO-1243zf | 0 to 40 | ~1.0 to ~11.2 |
| HF-HCFO-1233xf-HCFO-1233zdE-HFO-1234zeE-HFO-1243zf | 0 to 40 | ~1.0 to ~10.1 |
| HF-HCFO-1233xf-HCFO-1233zdE-HFO-1234zeZ-HFO-1243zf | 0 to 40 | ~1.0 to ~9.9 |
| HF-HCFO-1233xf-HFO-1234zeE-HFO-1234zeZ-HFO-1243zf | 0 to 40 | ~1.0 to ~10.1 |
| HF-HFO-1234yf-HFO-1234zeE-HFO-1234zeZ-HFO-1243zf | 0 to 40 | ~1.3 to ~11.4 |
| HF-HFO-1234yf-HFO-1234zeE-HCFO-1233zdE-HFO-1243zf | 0 to 40 | ~1.0 to ~11.4 |
| HF-HFO-1234yf-HFO-1234zeZ-HCFO-1233zdE-HFO-1243zf | 0 to 40 | ~1.1 to ~11.2 |
| HF-HFO-1234yf-HFC-245cb-HFO-1234zeE-HFO-1243zf | 0 to 40 | ~2.5 to ~11.6 |
| HF-HFO-1234yf-HFC-245cb-HFO-1234zeZ-HFO-1243zf | 0 to 40 | ~1.3 to ~10.3 |
| HF-HFO-1234yf-HFC-245cb-HCFO-1233zdE-HFO-1243zf | 0 to 40 | ~1.1 to ~11.4 |
| HF-HFC-245cb-HCFO-1233zdE-HFO-1234zeE-HFO-1243zf | 0 to 40 | ~1.1 to ~10.2 |
| HF-HFC-245cb-HCFO-1233zdE-HFO-1234zeZ-HFO-1243zf | 0 to 40 | ~1.0 to ~10.1 |
| HF-HFC-245cb-HFO-1234zeE-HFO-1234zeZ-HFO-1243zf | 0 to 40 | ~1.2 to ~10.2 |
| HF-HCFO-1233zdE-HFO-1234zeE-HFO-1234zeZ-HFO-1243zf | 0 to 40 | ~1.0 to ~10.1 |

EXAMPLE 9: DECANTATION RANGE OF PENTERNARY MIXTURES

| System with 5 compounds | Decantation ranges Mass percentage of HF | | |
|---|---|---|---|
| | Isotherm 0° C. | Isotherm 25° C. | Isotherm 40° C. |
| HF-HCFO-1233xf-HFC-245cb-HCFO-1233zdE-HFO-1243zf | 5-75 | 5-70 | 5-65 |
| HF-HCFO-1233xf-HFC-245cb-HFO-1234zeE-HFO-1243zf | 10-75 | 10-65 | * |
| HF-HCFO-1233xf-HFC-245cb-HFO-1234zeZ-HFO-1243zf | 5-75 | 5-70 | 10-60 |
| HF-HCFO-1233xf-HFC-245cb-HFO-1234yf-HFO-1243zf | 5-75 | 10-70 | * |
| HF-HCFO-1233xf-HFO-1234yf-HFO-1234zeE-HFO-1243zf | 5-70 | 10-60 | * |
| HF-HCFO-1233xf-HFO-1234yf-HFO-1234zeZ-HFO-1243zf | 5-75 | 10-65 | 20-40 |
| HF-HCFO-1233xf-HFO-1234yf-HCFO-1233zdE-HFO-1243zf | 5-75 | 5-65 | 15-45 |
| HF-HCFO-1233xf-HCFO-1233zdE-HFO-1234zeE-HFO-1243zf | 5-75 | 5-65 | 15-45 |
| HF-HCFO-1233xf-HCFO-1233zdE-HFO-1234zeZ-HFO-1243zf | 5-75 | 5-70 | 10-60 |
| HF-HCFO-1233xf-HFO-1234zeE-HFO-1234zeZ-HFO-1243zf | 5-75 | 10-65 | 15-40 |
| HF-HFO-1234yf-HFO-1234zeE-HFO-1234zeZ-HFO-1243zf | 5-70 | 10-60 | * |
| HF-HFO-1234yf-HFO-1234zeE-HCFO-1233zdE-HFO-1243zf | 5-70 | 10-60 | * |
| HF-HFO-1234yf-HFO-1234zeZ-HCFO-1233zdE-HFO-1243zf | 5-75 | 10-65 | 15-45 |
| HF-HFO-1234yf-HFC-245cb-HFO-1234zeE-HFO-1243zf | 5-75 | 15-65 | * |
| HF-HFO-1234yf-HFC-245cb-HFO-1234zeZ-HFO-1243zf | 5-75 | 10-70 | * |
| HF-HFO-1234yf-HFC-245cb-HCFO-1233zdE-HFO-1243zf | 5-75 | 10-70 | * |
| HF-HFC-245cb-HCFO-1233zdE-HFO-1234zeE-HFO-1243zf | 5-75 | 10-65 | * |
| HF-HFC-245cb-HCFO-1233zdE-HFO-1234zeZ-HFO-1243zf | 5-75 | 5-70 | 10-60 |
| HF-HFC-245cb-HFO-1234zeE-HFO-1234zeZ-HFO-1243zf | 5-75 | 10-65 | * |
| HF-HCFO-1233zdE-HFO-1234zeE-HFO-1234zeZ-HFO-1243zf | 5-75 | 5-65 | 15-50 |

EXAMPLE 10: SYSTEM WITH SIX COMPOUNDS, ISOTHERM AT 25° C.

HF-HCFO-1233xf-HFO-1234yf-HFC-245cb-HFO-1234zeE-HFO-1243zf

| Organics 0.2 F1233xf + 0.2 F1234yf + 0.2 F245cb + 0.2 F1234zeE + 0.2 F1243zf | | Organics 0.96 F1233xf + 0.01 F1234yf + 0.01 F245cb + 0.01 F1234zeE + 0.01 F1243zf | | Organics 0.01 F1233xf + 0.96 F1234yf + 0.01 F245cb + 0.01 F1234zeE + 0.01 F1243zf | | Organics 0.01 F1233xf + 0.01 F1234yf + 0.96 F245cb + 0.01 F1234zeE + 0.01 F1243zf | | Organics 0.01 F1233xf + 0.01 F1234yf + 0.01 F245cb + 0.96 F1234zeE + 0.01 F1243zf | | Organics 0.01 F1233xf + 0.01 F1234yf + 0.01 F245cb + 0.01 F1234zeE + 0.96 F1243zf | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.9 | 0 | 1.7 | 0 | 6.7 | 0 | 4.7 | 0 | 4.9 | 0 | 5.8 |
| 0.05 | 5.9 | 0.05 | 2.8 | 0.05 | 7.7 | 0.05 | 5.8 | 0.05 | 5.8 | 0.05 | 6.7 |
| 0.1 | 5.9 | 0.1 | 2.8 | 0.1 | 7.7 | 0.1 | 5.8 | 0.1 | 5.9 | 0.1 | 6.8 |
| 0.15 | 5.9 | 0.15 | 2.8 | 0.15 | 7.7 | 0.15 | 5.8 | 0.15 | 5.8 | 0.15 | 6.8 |
| 0.2 | 5.9 | 0.2 | 2.8 | 0.2 | 7.7 | 0.2 | 5.8 | 0.2 | 5.8 | 0.2 | 6.8 |
| 0.25 | 5.9 | 0.25 | 2.8 | 0.25 | 7.7 | 0.25 | 5.8 | 0.25 | 5.8 | 0.25 | 6.8 |
| 0.3 | 5.9 | 0.3 | 2.8 | 0.3 | 7.7 | 0.3 | 5.8 | 0.3 | 5.8 | 0.3 | 6.8 |

-continued

| Organics 0.2 F1233xf + 0.2 F1234yf + 0.2 F245cb + 0.2 F1234zeE + 0.2 F1243zf | | Organics 0.96 F1233xf + 0.01 F1234yf + 0.01 F245cb + 0.01 F1234zeE + 0.01 F1243zf | | Organics 0.01 F1233xf + 0.96 F1234yf + 0.01 F245cb + 0.01 F1234zeE + 0.01 F1243zf | | Organics 0.01 F1233xf + 0.01 F1234yf + 0.96 F245cb + 0.01 F1234zeE + 0.01 F1243zf | | Organics 0.01 F1233xf + 0.01 F1234yf + 0.01 F245cb + 0.96 F1234zeE + 0.01 F1243zf | | Organics 0.01 F1233xf + 0.01 F1234yf + 0.01 F245cb + 0.01 F1234zeE + 0.96 F1243zf | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0.35 | 5.9 | 0.35 | 2.8 | 0.35 | 7.7 | 0.35 | 5.8 | 0.35 | 5.6 | 0.35 | 6.8 |
| 0.4 | 5.9 | 0.4 | 2.8 | 0.4 | 7.7 | 0.4 | 5.8 | 0.4 | 5.8 | 0.4 | 6.8 |
| 0.45 | 5.9 | 0.45 | 2.8 | 0.45 | 7.7 | 0.45 | 5.8 | 0.45 | 5.8 | 0.45 | 6.7 |
| 0.5 | 5.9 | 0.5 | 2.8 | 0.5 | 7.7 | 0.5 | 5.8 | 0.5 | 5.8 | 0.5 | 6.7 |
| 0.55 | 5.9 | 0.55 | 2.8 | 0.55 | 7.7 | 0.55 | 5.8 | 0.55 | 5.7 | 0.55 | 6.7 |
| 0.6 | 5.9 | 0.6 | 2.8 | 0.6 | 7.7 | 0.6 | 5.8 | 0.6 | 5.7 | 0.6 | 6.7 |
| 0.65 | 5.9 | 0.65 | 2.8 | 0.65 | 7.7 | 0.65 | 5.8 | 0.65 | 5.6 | 0.65 | 6.6 |
| 0.7 | 5.9 | 0.7 | 2.8 | 0.7 | 7.6 | 0.7 | 5.8 | 0.7 | 5.4 | 0.7 | 6.5 |
| 0.75 | 5.7 | 0.75 | 2.8 | 0.75 | 7.5 | 0.75 | 5.8 | 0.75 | 5.2 | 0.75 | 6.4 |
| 0.8 | 5.5 | 0.7 | 2.7 | 0.8 | 7.2 | 0.8 | 5.8 | 0.8 | 4.8 | 0.8 | 6.1 |
| 0.85 | 5.0 | 0.85 | 2.5 | 0.85 | 6.6 | 0.85 | 5.8 | 0.85 | 4.3 | 0.85 | 5.6 |
| 0.9 | 4.2 | 0.9 | 2.2 | 0.9 | 5.5 | 0.9 | 5.0 | 0.9 | 3.6 | 0.9 | 4.8 |
| 0.95 | 3.0 | 0.95 | 1.8 | 0.95 | 3.8 | 0.95 | 3.5 | 0.95 | 2.6 | 0.95 | 3.4 |
| 1 | 1.2 | 1 | 1.2 | 1 | 1.2 | 1 | 1.2 | 1 | 1.2 | 1 | 1.2 |

25

HF-HCFO-1233xf-HFO-1234yf-HFC-245cb-HFO-1234zeZ-HFO-1243zf

| Organics 0.2 F1233xf + 0.2 F1234yf + 0.2 F245cb + 0.2 F1234zeZ + 0.2 F1243zf | | Organics 0.96 F1233xf + 0.01 F1234yf + 0.01 F245cb + 0.01 F1234zeZ + 0.01 F1243zf | | Organics 0.01 F1233xf + 0.96 F1234yf + 0.01 F245cb + 0.01 F1234zeZ + 0.01 F1243zf | | Organics 0.01 F1233xf + 0.01 F1234yf + 0.96 F245cb + 0.01 F1234zeZ + 0.01 F1243zf | | Organics 0.01 F1233xf + 0.01 F1234yf + 0.01 F245cb + 0.96 F1234zeZ + 0.01 F1243zf | | Organics 0.01 F1233xf + 0.01 F1234yf + 0.01 F245cb + 0.01 F1234zeZ + 0.96 F1243zf | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.2 | 0 | 1.7 | 0 | 6.7 | 0 | 4.6 | 0 | 1.9 | 0 | 5.8 |
| 0.05 | 5.3 | 0.05 | 2.8 | 0.05 | 7.6 | 0.05 | 5.8 | 0.05 | 3.0 | 0.05 | 6.7 |
| 0.1 | 5.3 | 0.1 | 2.8 | 0.1 | 7.7 | 0.1 | 5.8 | 0.1 | 3.0 | 0.1 | 6.8 |
| 0.15 | 5.3 | 0.15 | 2.8 | 0.15 | 7.6 | 0.15 | 5.8 | 0.15 | 3.0 | 0.15 | 6.7 |
| 0.2 | 5.3 | 0.2 | 2.8 | 0.2 | 7.6 | 0.2 | 5.8 | 0.2 | 3.0 | 0.2 | 6.7 |
| 0.25 | 5.3 | 0.25 | 2.8 | 0.25 | 7.6 | 0.25 | 5.8 | 0.25 | 3.0 | 0.25 | 6.7 |
| 0.3 | 5.3 | 0.3 | 2.8 | 0.3 | 7.6 | 0.3 | 5.8 | 0.3 | 3.0 | 0.3 | 6.7 |
| 0.35 | 5.3 | 0.35 | 2.8 | 0.35 | 7.6 | 0.35 | 5.8 | 0.35 | 3.0 | 0.35 | 6.7 |
| 0.4 | 5.3 | 0.4 | 2.8 | 0.4 | 7.6 | 0.4 | 5.8 | 0.4 | 3.0 | 0.4 | 6.7 |
| 0.45 | 5.3 | 0.45 | 2.8 | 0.45 | 7.6 | 0.45 | 5.8 | 0.45 | 3.0 | 0.45 | 6.7 |
| 0.5 | 5.3 | 0.5 | 2.8 | 0.5 | 7.6 | 0.5 | 5.8 | 0.5 | 3.0 | 0.5 | 6.7 |
| 0.55 | 5.3 | 0.55 | 2.8 | 0.55 | 7.6 | 0.55 | 5.8 | 0.55 | 3.0 | 0.55 | 6.7 |
| 0.6 | 5.3 | 0.6 | 2.8 | 0.6 | 7.6 | 0.6 | 5.8 | 0.6 | 3.0 | 0.6 | 6.7 |
| 0.65 | 5.3 | 0.65 | 2.8 | 0.65 | 7.6 | 0.65 | 5.8 | 0.65 | 3.0 | 0.65 | 6.6 |
| 0.7 | 5.3 | 0.7 | 2.8 | 0.7 | 7.6 | 0.7 | 5.8 | 0.7 | 3.0 | 0.7 | 6.5 |
| 0.75 | 5.3 | 0.75 | 2.8 | 0.75 | 7.5 | 0.75 | 5.8 | 0.75 | 3.0 | 0.75 | 6.4 |
| 0.8 | 5.1 | 0.8 | 2.7 | 0.8 | 7.2 | 0.8 | 5.8 | 0.8 | 2.9 | 0.8 | 6.1 |
| 0.85 | 4.7 | 0.85 | 2.5 | 0.85 | 6.6 | 0.85 | 5.8 | 0.85 | 2.7 | 0.85 | 5.6 |
| 0.9 | 4.0 | 0.9 | 2.2 | 0.9 | 5.5 | 0.9 | 5.0 | 0.9 | 2.4 | 0.9 | 4.7 |
| 0.95 | 2.9 | 0.95 | 1.8 | 0.95 | 3.8 | 0.95 | 3.5 | 0.95 | 1.9 | 0.95 | 3.4 |
| 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HCFO-1233zdE-HFO-1243zf

| Organics 0.2 F1233xf + 0.2 F1234yf + 0.2 F245cb + 0.2 F1233zdE + 0.2 F1243zf | | Organics 0.96 F1233xf + 0.01 F1234yf + 0.01 F245cb + 0.01 F1233zdE + 0.01 F1243zf | | Organics 0.01 F1233xf + 0.96 F1234yf + 0.01 F245cb + 0.01 F1233zdE + 0.01 F1243zf | | Organics 0.01 F1233xf + 0.01 F1234yf + 0.96 F245cb + 0.01 F1233zdE + 0.01 F1243zf | | Organics 0.01 F1233xf + 0.01 F1234yf + 0.01 F245cb + 0.96 F1233zdE + 0.01 F1243zf | | Organics 0.01 F1233xf + 0.01 F1234yf + 0.01 F245cb + 0.01 F1233zdE + 0.96 F1243zf | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.2 | 0 | 1.7 | 0 | 6.7 | 0 | 4.6 | 0 | 1.5 | 0 | 5.8 |
| 0.05 | 5.3 | 0.05 | 2.8 | 0.05 | 7.6 | 0.05 | 5.8 | 0.05 | 2.6 | 0.05 | 6.7 |
| 0.1 | 5.3 | 0.1 | 2.8 | 0.1 | 7.7 | 0.1 | 5.8 | 0.1 | 2.6 | 0.1 | 6.8 |
| 0.15 | 5.3 | 0.15 | 2.8 | 0.15 | 7.6 | 0.15 | 5.8 | 0.15 | 2.6 | 0.15 | 6.7 |
| 0.2 | 5.3 | 0.2 | 2.8 | 0.2 | 7.6 | 0.2 | 5.8 | 0.2 | 2.6 | 0.2 | 6.7 |
| 0.25 | 5.3 | 0.25 | 2.8 | 0.25 | 7.6 | 0.25 | 5.8 | 0.25 | 2.6 | 0.25 | 6.7 |
| 0.3 | 5.3 | 0.3 | 2.8 | 0.3 | 7.6 | 0.3 | 5.8 | 0.3 | 2.6 | 0.3 | 6.7 |
| 0.35 | 5.3 | 0.35 | 2.8 | 0.35 | 7.6 | 0.35 | 5.8 | 0.35 | 2.6 | 0.35 | 6.7 |
| 0.4 | 5.3 | 0.4 | 2.8 | 0.4 | 7.6 | 0.4 | 5.8 | 0.4 | 2.6 | 0.4 | 6.7 |
| 0.45 | 5.3 | 0.45 | 2.8 | 0.45 | 7.6 | 0.45 | 5.8 | 0.45 | 2.6 | 0.45 | 6.7 |
| 0.5 | 5.3 | 0.5 | 2.8 | 0.5 | 7.6 | 0.5 | 5.8 | 0.5 | 2.6 | 0.5 | 6.7 |
| 0.55 | 5.3 | 0.55 | 2.8 | 0.55 | 7.6 | 0.55 | 5.8 | 0.55 | 2.6 | 0.55 | 6.7 |
| 0.6 | 5.3 | 0.6 | 2.8 | 0.6 | 7.6 | 0.6 | 5.8 | 0.6 | 2.6 | 0.6 | 5.7 |
| 0.65 | 5.3 | 0.65 | 2.8 | 0.65 | 7.6 | 0.65 | 5.8 | 0.65 | 2.6 | 0.65 | 6.6 |
| 0.7 | 5.3 | 0.7 | 2.8 | 0.7 | 7.6 | 0.7 | 5.8 | 0.7 | 2.6 | 0.7 | 6.5 |
| 0.75 | 5.2 | 0.75 | 2.8 | 0.75 | 7.5 | 0.75 | 5.8 | 0.75 | 2.6 | 0.75 | 6.4 |
| 0.8 | 5.0 | 0.8 | 2.7 | 0.8 | 7.2 | 0.8 | 5.8 | 0.8 | 2.5 | 0.8 | 6.1 |
| 0.85 | 4.6 | 0.85 | 2.5 | 0.85 | 6.6 | 0.85 | 5.8 | 0.85 | 2.3 | 0.85 | 5.6 |
| 0.9 | 3.9 | 0.9 | 2.2 | 0.9 | 5.5 | 0.9 | 5.0 | 0.9 | 2.0 | 0.9 | 4.7 |
| 0.95 | 2.8 | 0.95 | 1.8 | 0.95 | 3.8 | 0.95 | 3.5 | 0.95 | 1.7 | 0.95 | 3.4 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HFO-1234zeZ-HFO-1243zf

| Organics 0.2 F1233xf + 0.2 F1234yf + 0.2 F1243zf + 0.2 F1234zeE + 0.2 F1234zeZ | | Organics 0.96 F1233xf + 0.01 F1234yf + 0.01 F1243zf + 0.01 F1234zeE + 0.01 F1234zeZ | | Organics 0.01 F1233xf + 0.95 F1234yf + 0.01 F1243zf + 0.01 F1234zeE + 0.01 F1234zeZ | | Organics 0.01 F1233xf + 0.01 F1234yf + 0.96 F1243zf + 0.01 F1234zeE + 0.01 F1234zeZ | | Organics 0.01 F1233xf + 0.01 F1234yf + 0.01 F1243zf + 0.96 F1234zeE + 0.01 F1234zeZ | | Organics 0.01 F1233xf + 0.01 F1234yf + 0.01 F1243zf + 0.01 F1234zeE + 0.96 F1234zeZ | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.3 | 0 | 1.7 | 0 | 6.7 | 0 | 5.8 | 0 | 4.8 | 0 | 1.9 |
| 0.05 | 5.3 | 0.05 | 2.8 | 0.05 | 7.6 | 0.05 | 6.7 | 0.05 | 5.8 | 0.05 | 3.0 |
| 0.1 | 5.3 | 0.1 | 2.8 | 0.1 | 7.6 | 0.1 | 6.7 | 0.1 | 5.8 | 0.1 | 3.0 |
| 0.15 | 5.3 | 0.15 | 2.8 | 0.15 | 7.6 | 0.15 | 6.7 | 0.15 | 5.8 | 0.15 | 3.0 |
| 0.2 | 5.3 | 0.2 | 2.8 | 0.2 | 7.6 | 0.2 | 6.7 | 0.2 | 5.8 | 0.2 | 3.0 |
| 0.25 | 5.3 | 0.25 | 2.8 | 0.25 | 7.6 | 0.25 | 6.7 | 0.25 | 5.8 | 0.25 | 3.0 |
| 0.3 | 5.3 | 0.3 | 2.8 | 0.3 | 7.6 | 0.3 | 6.7 | 0.3 | 5.8 | 0.3 | 3.0 |
| 0.35 | 5.3 | 0.35 | 2.8 | 0.35 | 7.6 | 0.35 | 6.7 | 0.35 | 5.8 | 0.35 | 3.0 |
| 0.4 | 5.3 | 0.4 | 2.8 | 0.4 | 7.6 | 0.4 | 6.7 | 0.4 | 5.8 | 0.4 | 3.0 |
| 0.45 | 5.3 | 0.45 | 2.8 | 0.45 | 7.6 | 0.45 | 6.7 | 0.45 | 5.8 | 0.45 | 3.0 |
| 0.5 | 5.3 | 0.5 | 2.8 | 0.5 | 7.6 | 0.5 | 6.7 | 0.5 | 5.8 | 0.5 | 3.0 |
| 0.55 | 5.3 | 0.55 | 2.8 | 0.55 | 7.6 | 0.55 | 6.7 | 0.55 | 5.7 | 0.55 | 3.0 |
| 0.6 | 5.3 | 0.6 | 2.8 | 0.6 | 7.6 | 0.6 | 6.7 | 0.6 | 5.6 | 0.6 | 3.0 |
| 0.65 | 5.3 | 0.65 | 2.8 | 0.65 | 7.6 | 0.65 | 6.6 | 0.65 | 5.5 | 0.65 | 3.0 |
| 0.7 | 5.2 | 0.7 | 2.8 | 0.7 | 7.6 | 0.7 | 6.5 | 0.7 | 5.4 | 0.7 | 3.0 |
| 0.75 | 5.0 | 0.75 | 2.8 | 0.75 | 7.5 | 0.75 | 6.3 | 0.75 | 5.1 | 0.75 | 3.0 |
| 0.8 | 4.8 | 0.8 | 2.7 | 0.8 | 7.1 | 0.8 | 6.1 | 0.8 | 4.8 | 0.8 | 2.9 |
| 0.85 | 4.3 | 0.85 | 2.5 | 0.85 | 6.5 | 0.85 | 5.6 | 0.85 | 4.3 | 0.85 | 2.7 |
| 0.9 | 3.7 | 0.9 | 2.2 | 0.9 | 5.5 | 0.9 | 4.7 | 0.9 | 3.6 | 0.9 | 2.4 |
| 0.95 | 2.7 | 0.95 | 1.8 | 0.95 | 3.8 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeE-HCFO-1233zdE-HFO-1243zf

| Organics 0.2 F1233xf + 0.2 F1234yf + 0.2 F1243zf + 0.2 F1234zeE + 0.2 F1233zdE | | Organics 0.96 F1233xf + 0.01 F1234yf + 0.01 F1243zf + 0.01 F1234zeE + 0.01 F1233zdE | | Organics 0.01 F1233xf + 0.96 F1234yf + 0.01 F1243zf + 0.01 F1234zeE + 0.01 F1233zdE | | Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 6.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 6.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.7 | 0.6 | 5.6 | 0.6 | 2.6 |
| 0.65 | 5.2 | 0.65 | 2.8 | 0.65 | 7.6 | 0.65 | 6.6 | 0.65 | 5.5 | 0.65 | 2.6 |
| 0.7 | 5.1 | 0.7 | 2.8 | 0.7 | 7.6 | 0.7 | 6.5 | 0.7 | 5.4 | 0.7 | 2.6 |
| 0.75 | 5.0 | 0.75 | 2.8 | 0.75 | 7.5 | 0.75 | 6.3 | 0.75 | 5.1 | 0.75 | 2.6 |
| 0.8 | 4.7 | 0.8 | 2.6 | 0.8 | 7.1 | 0.8 | 6.1 | 0.8 | 4.8 | 0.8 | 2.4 |
| 0.85 | 4.3 | 0.85 | 2.5 | 0.85 | 6.5 | 0.85 | 5.6 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234yf-HFO-1234zeZ-HCFO-1233zdE-HFO-1243zf

| Organics 0.2 F1233xf + 0.2 F1234yf + 0.2 F1243zf + 0.2 F1234zeZ + 0.2 F1233zdE | | Organics 0.96 F1233xf + 0.01 F1234yf + 0.01 F1243zf + 0.01 F1234zeZ + 0.01 F1233zdE | | Organics 0.01 F1233xf + 0.96 F1234yf + 0.01 F1243zf + 0.01 F1234zeZ + 0.01 F1233zdE | | Organics 0.01 F1233xf + 0.01 F1234yf + 0.96 F1243zf + 0.01 F1234zeZ + 0.01 F1233zdE | | Organics 0.01 F1233xf + 0.01 F1234yf + 0.01 F1243zf + 0.96 F1234zeZ + 0.01 F1233zdE | | Organics 0.01 F1233xf + 0.01 F1234yf + 0.01 F1243zf + 0.01 F1234zeZ + 0.96 F1233zdE | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |
| 0.35 | 4.7 | 0.35 | 2.8 | 0.35 | 7.6 | 0.35 | 6.7 | 0.35 | 3.0 | 0.35 | 2.5 |
| 0.4 | 4.7 | 0.4 | 2.8 | 0.4 | 7.6 | 0.4 | 6.7 | 0.4 | 3.0 | 0.4 | 2.5 |
| 0.45 | 4.7 | 0.45 | 2.8 | 0.45 | 7.6 | 0.45 | 6.7 | 0.45 | 3.0 | 0.45 | 2.5 |
| 0.5 | 4.7 | 0.5 | 2.8 | 0.5 | 7.6 | 0.5 | 6.7 | 0.5 | 3.0 | 0.5 | 2.5 |
| 0.55 | 4.7 | 0.55 | 2.8 | 0.55 | 7.6 | 0.55 | 6.7 | 0.55 | 3.0 | 0.55 | 2.5 |
| 0.6 | 4.7 | 0.6 | 2.8 | 0.6 | 7.5 | 0.5 | 6.6 | 0.6 | 3.0 | 0.6 | 2.5 |
| 0.65 | 4.7 | 0.65 | 2.8 | 0.65 | 7.6 | 0.65 | 6.6 | 0.65 | 3.0 | 0.65 | 2.5 |
| 0.7 | 4.7 | 0.7 | 2.8 | 0.7 | 7.6 | 0.7 | 6.5 | 0.7 | 3.0 | 0.7 | 2.5 |
| 0.75 | 4.5 | 0.75 | 2.8 | 0.75 | 7.4 | 0.75 | 6.3 | 0.75 | 3.0 | 0.75 | 2.5 |
| 0.8 | 4.3 | 0.8 | 2.6 | 0.8 | 7.1 | 0.8 | 6.0 | 0.8 | 2.9 | 0.8 | 2.4 |
| 0.85 | 3.9 | 0.85 | 2.4 | 0.85 | 6.5 | 0.85 | 5.5 | 0.85 | 2.7 | 0.85 | 2.3 |
| 0.9 | 3.4 | 0.9 | 2.2 | 0.9 | 5.5 | 0.9 | 4.7 | 0.9 | 2.3 | 0.9 | 2.0 |
| 0.95 | 2.5 | 0.95 | 1.7 | 0.95 | 3.8 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFC-245cb-HFO-1234zeE-HFO-1234zeZ-HFO-1243zf

| Organics 0.2 F1233xf + 0.2 F245cb + 0.2 F1243zf + 0.2 F1234zeE + 0.2 F1234zeZ | | Organics 0.96 F1233xf + 0.01 F245cb + 0.01 F1243zf + 0.01 F1234zeE + 0.01 F1234zeZ | | Organics 0.01 F1233xf + 0.96 F245cd + 0.01 F1243zf + 0.01 F1234zeE + 0.01 F1234zeZ | | Organics 0.01 F1233xf + 0.01 F245cb + 0.96 F1243zf + 0.01 F1234zeE + 0.01 F1234zeZ | | Organics 0.01 F1233xf + 0.01 F245cb + 0.01 F1243zf + 0.96 F1234zeE + 0.01 F1234zeZ | | Organics 0.01 F1233xf + 0.01 F245cb + 0.01 F1243zf + 0.01 F1234zeE + 0.96 F1234zeZ | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.8 | 0 | 1.7 | 0 | 4.6 | 0 | 5.8 | 0 | 4.8 | 0 | 1.9 |
| 0.05 | 4.9 | 0.05 | 2.8 | 0.05 | 5.8 | 0.05 | 6.7 | 0.05 | 5.8 | 0.05 | 3.0 |
| 0.1 | 4.9 | 0.1 | 2.8 | 0.1 | 5.8 | 0.1 | 6.7 | 0.1 | 5.8 | 0.1 | 3.0 |
| 0.15 | 4.9 | 0.15 | 2.8 | 0.15 | 5.8 | 0.15 | 6.7 | 0.15 | 5.8 | 0.15 | 3.0 |
| 0.2 | 4.9 | 0.2 | 2.8 | 0.2 | 5.8 | 0.2 | 6.7 | 0.2 | 5.8 | 0.2 | 3.0 |
| 0.25 | 4.9 | 0.25 | 2.8 | 0.25 | 5.8 | 0.25 | 6.7 | 0.25 | 5.8 | 0.25 | 3.0 |
| 0.3 | 4.9 | 0.3 | 2.8 | 0.3 | 5.8 | 0.3 | 6.7 | 0.3 | 5.8 | 0.3 | 3.0 |
| 0.35 | 4.9 | 0.35 | 2.8 | 0.35 | 5.8 | 0.35 | 6.7 | 0.35 | 5.8 | 0.35 | 3.0 |
| 0.4 | 4.9 | 0.4 | 2.8 | 0.4 | 5.8 | 0.4 | 6.7 | 0.4 | 5.8 | 0.4 | 3.0 |
| 0.45 | 4.9 | 0.45 | 2.8 | 0.45 | 5.8 | 0.45 | 6.7 | 0.45 | 5.8 | 0.45 | 3.0 |
| 0.5 | 4.9 | 0.5 | 2.8 | 0.5 | 5.8 | 0.5 | 6.7 | 0.5 | 5.7 | 0.5 | 3.0 |
| 0.55 | 4.9 | 0.55 | 2.8 | 0.55 | 5.8 | 0.55 | 6.7 | 0.55 | 5.7 | 0.55 | 3.0 |
| 0.6 | 4.9 | 0.6 | 2.8 | 0.6 | 5.8 | 0.6 | 6.6 | 0.6 | 5.6 | 0.6 | 3.0 |
| 0.65 | 4.9 | 0.65 | 2.8 | 0.65 | 5.8 | 0.65 | 6.6 | 0.65 | 5.5 | 0.65 | 3.0 |
| 0.7 | 4.9 | 0.7 | 2.8 | 0.7 | 5.8 | 0.7 | 6.5 | 0.7 | 5.4 | 0.7 | 3.0 |
| 0.75 | 4.8 | 0.75 | 2.8 | 0.75 | 5.8 | 0.75 | 6.3 | 0.75 | 5.1 | 0.75 | 3.0 |
| 0.8 | 4.6 | 0.8 | 2.6 | 0.8 | 5.8 | 0.8 | 6.0 | 0.8 | 4.8 | 0.0 | 2.9 |
| 0.85 | 4.2 | 0.85 | 2.4 | 0.85 | 5.8 | 0.85 | 5.6 | 0.85 | 4.3 | 0.85 | 2.7 |
| 0.9 | 3.6 | 0.9 | 2.2 | 0.9 | 5.0 | 0.9 | 4.7 | 0.9 | 3.6 | 0.9 | 2.4 |
| 0.95 | 2.6 | 0.95 | 1.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HCFO-1233xf-HFC-245cb-HFO-1234zeE-HCFO-1233zdE-HFO-1243zf

| Organics 0.2 F1233xf + 0.2 F245cb + 0.2 F1243zf + 0.2 F1234zeE + 0.2 F1233zdE | | Organics 0.96 F1233xf + 0.01 F245cb + 0.01 F1243zf + 0.01 F1234zeE + 0.01 F1233zdE | | Organics 0.01 F1233xf + 0.96 F245cb + 0.01 F1243zf + 0.01 F1234zeE + 0.01 F1233zdE | | Organics 0.01 F1233xf + 0.01 F245cb + 0.96 F1243zf + 0.01 F1234zeE + 0.01 F1233zdE | | Organics 0.01 F1233xf + 0.01 F245cb + 0.01 F1243zf + 0.96 F1234zeE + 0.01 F1233zdE | | Organics 0.01 F1233xf + 0.01 F245cb + 0.01 F1243zf + 0.01 F1234zeE + 0.96 F1233zdE | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.8 | 0 | 1.7 | 0 | 4.6 | 0 | 5.8 | 0 | 4.8 | 0 | 1.5 |
| 0.05 | 4.9 | 0.05 | 2.8 | 0.05 | 5.8 | 0.05 | 6.7 | 0.05 | 5.8 | 0.05 | 2.6 |
| 0.1 | 4.9 | 0.1 | 2.8 | 0.1 | 5.8 | 0.1 | 6.7 | 0.1 | 5.8 | 0.1 | 2.6 |
| 0.15 | 4.9 | 0.15 | 2.8 | 0.15 | 5.8 | 0.15 | 6.7 | 0.15 | 5.8 | 0.15 | 2.6 |
| 0.2 | 4.9 | 0.2 | 2.8 | 0.2 | 5.8 | 0.2 | 6.7 | 0.2 | 5.8 | 0.2 | 2.6 |
| 0.25 | 4.9 | 0.25 | 2.8 | 0.25 | 5.8 | 0.25 | 6.7 | 0.25 | 5.8 | 0.25 | 2.6 |
| 0.3 | 4.9 | 0.3 | 2.8 | 0.3 | 5.8 | 0.3 | 6.7 | 0.3 | 5.8 | 0.3 | 2.6 |
| 0.35 | 4.9 | 0.35 | 2.8 | 0.35 | 5.8 | 0.35 | 6.7 | 0.35 | 5.8 | 0.35 | 2.6 |
| 0.4 | 4.9 | 0.4 | 2.8 | 0.4 | 5.8 | 0.4 | 6.7 | 0.4 | 5.8 | 0.4 | 2.6 |
| 0.45 | 4.9 | 0.45 | 2.8 | 0.45 | 5.8 | 0.45 | 6.7 | 0.45 | 5.8 | 0.45 | 2.6 |
| 0.5 | 4.9 | 0.5 | 2.8 | 0.5 | 5.8 | 0.5 | 6.7 | 0.5 | 5.7 | 0.5 | 2.6 |
| 0.55 | 4.9 | 0.55 | 2.8 | 0.55 | 5.8 | 0.55 | 6.7 | 0.55 | 5.7 | 0.55 | 2.6 |
| 0.6 | 4.9 | 0.6 | 2.8 | 0.6 | 5.8 | 0.6 | 6.6 | 0.6 | 5.6 | 0.6 | 2.6 |
| 0.65 | 4.9 | 0.65 | 2.8 | 0.65 | 5.8 | 0.65 | 6.6 | 0.65 | 5.5 | 0.65 | 2.5 |
| 0.7 | 4.9 | 0.7 | 2.8 | 0.7 | 5.8 | 0.7 | 6.5 | 0.7 | 5.4 | 0.7 | 2.5 |
| 0.75 | 4.7 | 0.75 | 2.8 | 0.75 | 5.8 | 0.75 | 6.3 | 0.75 | 5.1 | 0.75 | 2.5 |
| 0.8 | 4.5 | 0.8 | 2.6 | 0.8 | 5.8 | 0.8 | 6.0 | 0.8 | 4.8 | 0.8 | 2.4 |
| 0.85 | 4.1 | 0.85 | 2.4 | 0.85 | 5.8 | 0.85 | 5.6 | 0.85 | 4.3 | 0.85 | 2.3 |
| 0.9 | 3.5 | 0.9 | 2.2 | 0.9 | 5.0 | 0.9 | 4.7 | 0.9 | 3.6 | 0.9 | 2.0 |
| 0.95 | 2.6 | 0.95 | 1.7 | 0.95 | 3.5 | 0.95 | 3.3 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFC-245cb-HFO-1234zeZ-HCFO-1233zdE-HFO-1243zf

| Organics 0.2 F1233xf + 0.2 F245cb + 0.2 F1243zf + 0.2 F1234zeZ + 0.2 F1233zdE | | Organics 0.96 F1233xf + 0.01 F245cb + 0.01 F1243zf + 0.01 F1234zeZ + 0.01 F1233zdE | | Organics 0.01 F1233xf + 0.96 F245cb + 0.01 F1243zf + 0.01 F1234zeZ + 0.01 F1233zdE | | Organics 0.01 F1233xf + 0.01 F245cb + 0.96 F1243zf + 0.01 F1234zeZ + 0.01 F1233zdE | | Organics 0.01 F1233xf + 0.01 F245cb + 0.01 F1243zf + 0.96 F1234zeZ + 0.01 F1233zdE | | Organics 0.01 F1233xf + 0.01 F245cb + 0.01 F1243zf + 0.01 F1234zeZ + 0.96 F1233zdE | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.2 | 0 | 1.6 | 0 | 4.6 | 0 | 5.7 | 0 | 1.9 | 0 | 1.4 |
| 0.05 | 4.3 | 0.05 | 2.7 | 0.05 | 5.7 | 0.05 | 6.7 | 0.05 | 3.0 | 0.05 | 2.5 |
| 0.1 | 4.3 | 0.1 | 2.7 | 0.1 | 5.7 | 0.1 | 6.7 | 0.1 | 3.0 | 0.1 | 2.5 |
| 0.15 | 4.3 | 0.15 | 2.7 | 0.15 | 5.7 | 0.15 | 6.7 | 0.15 | 3.0 | 0.15 | 2.5 |
| 0.2 | 4.3 | 0.2 | 2.7 | 0.2 | 5.7 | 0.2 | 6.7 | 0.2 | 3.0 | 0.2 | 2.5 |
| 0.25 | 4.3 | 0.25 | 2.7 | 0.25 | 5.7 | 0.25 | 6.7 | 0.25 | 3.0 | 0.25 | 2.5 |
| 0.3 | 4.3 | 0.3 | 2.7 | 0.3 | 5.7 | 0.3 | 6.7 | 0.3 | 3.0 | 0.3 | 2.5 |
| 0.35 | 4.3 | 0.35 | 2.7 | 0.35 | 5.7 | 0.35 | 6.7 | 0.35 | 3.0 | 0.35 | 2.5 |
| 0.4 | 4.3 | 0.4 | 2.7 | 0.4 | 5.8 | 0.4 | 6.7 | 0.4 | 3.0 | 0.4 | 2.5 |
| 0.45 | 4.3 | 0.45 | 2.7 | 0.45 | 5.8 | 0.45 | 6.7 | 0.45 | 3.0 | 0.45 | 2.5 |
| 0.5 | 4.3 | 0.5 | 2.7 | 0.5 | 5.8 | 0.5 | 6.7 | 0.5 | 3.0 | 0.5 | 2.5 |
| 0.55 | 4.3 | 0.55 | 2.7 | 0.55 | 5.8 | 0.55 | 6.7 | 0.55 | 3.0 | 0.55 | 2.5 |
| 0.6 | 4.3 | 0.6 | 2.7 | 0.6 | 5.8 | 0.6 | 6.6 | 0.6 | 3.0 | 0.6 | 2.5 |
| 0.65 | 4.3 | 0.65 | 2.7 | 0.65 | 5.8 | 0.65 | 6.6 | 0.65 | 3.0 | 0.65 | 2.5 |
| 0.7 | 4.3 | 0.7 | 2.7 | 0.7 | 5.8 | 0.7 | 6.5 | 0.7 | 3.0 | 0.7 | 2.5 |
| 0.70 | 4.3 | 0.75 | 2.7 | 0.75 | 5.8 | 0.75 | 6.3 | 0.75 | 3.0 | 0.75 | 2.5 |
| 0.8 | 4.1 | 0.8 | 2.6 | 0.8 | 5.8 | 0.8 | 6.0 | 0.8 | 2.9 | 0.8 | 2.4 |
| 0.85 | 3.8 | 0.85 | 2.4 | 0.85 | 5.8 | 0.85 | 5.5 | 0.85 | 2.7 | 0.85 | 2.3 |
| 0.9 | 3.3 | 0.9 | 2.1 | 0.9 | 5.0 | 0.9 | 4.7 | 0.9 | 2.3 | 0.9 | 2.0 |
| 0.95 | 2.4 | 0.95 | 1.7 | 0.95 | 3.5 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HCFO-1233xf-HFO-1234zeE-HFO-1234zeZ-HCFO-1233zdE-HFO-1243zf

| Organics 0.2 F1233xf + 0.2 F1243zf + 0.2 F1233zdE + 0.2 F1234zeE + 0.2 F1234zeZ | | Organics 0.96 F1233xf + 0.01 F1243zf + 0.01 F1233zdE + 0.01 F1234zeE + 0.01 F1234zeZ | | Organics 0.01 F1233xf + 0.96 F1243zf + 0.01 F1233zdE + 0.01 F1234zeE + 0.01 F1234zeZ | | Organics 0.01 F1233xf + 0.01 F1243zf + 0.96 F1233zdE + 0.01 F1234zeE + 0.01 F1234zeZ | | Organics 0.01 F1233xf + 0.01 F1243zf + 0.01 F1233zdE + 0.96 F1234zeE + 0.01 F1234zeZ | | Organics 0.01 F1233xf + 0.01 F1243zf + 0.01 F1233zdE + 0.01 F1234zeE + 0.96 F1234zeZ | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.2 | 0 | 1.6 | 0 | 5.7 | 0 | 1.4 | 0 | 4.8 | 0 | 1.9 |
| 0.05 | 4.3 | 0.05 | 2.7 | 0.05 | 6.7 | 0.05 | 2.5 | 0.05 | 5.7 | 0.05 | 3.0 |
| 0.1 | 4.3 | 0.1 | 2.7 | 0.1 | 6.7 | 0.1 | 2.5 | 0.1 | 5.8 | 0.1 | 3.0 |
| 0.15 | 4.3 | 0.15 | 2.7 | 0.15 | 6.7 | 0.15 | 2.5 | 0.15 | 5.8 | 0.15 | 3.0 |
| 0.2 | 4.3 | 0.2 | 2.7 | 0.2 | 6.7 | 0.2 | 2.5 | 0.2 | 5.8 | 0.2 | 3.0 |
| 0.25 | 4.3 | 0.25 | 2.7 | 0.25 | 6.7 | 0.25 | 2.5 | 0.25 | 5.8 | 0.25 | 3.0 |
| 0.3 | 4.3 | 0.2 | 2.7 | 0.3 | 6.7 | 0.3 | 2.5 | 0.3 | 5.8 | 0.3 | 3.0 |
| 0.35 | 4.3 | 0.35 | 2.7 | 0.35 | 6.7 | 0.35 | 2.5 | 0.35 | 5.8 | 0.35 | 3.0 |
| 0.4 | 4.3 | 0.4 | 2.7 | 0.4 | 6.7 | 0.4 | 2.5 | 0.4 | 5.8 | 0.4 | 3.0 |
| 0.45 | 4.3 | 0.45 | 2.7 | 0.45 | 6.7 | 0.45 | 2.5 | 0.45 | 5.7 | 0.45 | 3.0 |
| 0.5 | 4.3 | 0.5 | 2.7 | 0.5 | 6.7 | 0.5 | 2.5 | 0.5 | 5.7 | 0.5 | 3.0 |
| 0.55 | 4.2 | 0.55 | 2.7 | 0.55 | 6.6 | 0.55 | 2.5 | 0.55 | 5.7 | 0.55 | 3.0 |
| 0.6 | 4.2 | 0.6 | 2.7 | 0.6 | 6.6 | 0.6 | 2.5 | 0.6 | 5.6 | 0.6 | 3.0 |
| 0.65 | 4.2 | 0.65 | 2.7 | 0.65 | 6.6 | 0.65 | 2.5 | 0.65 | 5.5 | 0.65 | 3.0 |
| 0.7 | 4.2 | 0.7 | 2.7 | 0.7 | 6.5 | 0.7 | 2.5 | 0.7 | 5.3 | 0.70 | 3.0 |
| 0.75 | 4.0 | 0.75 | 2.7 | 0.75 | 6.3 | 0.75 | 2.5 | 0.75 | 5.1 | 0.75 | 3.0 |
| 0.8 | 3.8 | 0.8 | 2.6 | 0.8 | 6.0 | 0.8 | 2.4 | 0.8 | 4.7 | 0.8 | 2.3 |
| 0.85 | 3.5 | 0.85 | 2.4 | 0.85 | 5.5 | 0.85 | 2.2 | 0.85 | 4.3 | 0.85 | 2.6 |
| 0.9 | 3.0 | 0.9 | 2.1 | 0.9 | 4.7 | 0.9 | 2.0 | 0.9 | 3.6 | 0.9 | 2.3 |
| 0.95 | 2.2 | 0.95 | 1.7 | 0.95 | 3.3 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ-HFO-1243zf

| Organics 0.2 F1234yf + 0.2 F245cb + 0.2 F1243zf + 0.2 F1234zeE + 0.2 F1234zeZ | | Organics 0.96 F1234yf + 0.01 F245cb + 0.01 F1243zf + 0.01 F1234zeE + 0.01 F1234zeZ | | Organics 0.01 F1234yf + 0.96 F245cb + 0.01 F1243zf + 0.01 F1234zeE + 0.01 F1234zeZ | | Organics 0.01 F1234yf + 0.01 F245cb + 0.96 F1243zf + 0.01 F1234zeE + 0.01 F1234zeZ | | Organics 0.01 F1234yf + 0.01 F245cb + 0.01 F1243zf + 0.96 F1234zeE + 0.01 F1234zeZ | | Organics 0.01 F1234yf + 0.01 F245cb + 0.01 F1243zf + 0.01 F1234zeE + 0.96 F1234zeZ | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.8 | 0 | 6.7 | 0 | 4.7 | 0 | 5.8 | 0 | 4.9 | 0 | 2.0 |
| 0.05 | 5.9 | 0.05 | 7.7 | 0.05 | 5.8 | 0.05 | 6.7 | 0.05 | 5.8 | 0.05 | 3.1 |
| 0.1 | 5.9 | 0.1 | 7.7 | 0.1 | 5.8 | 0.1 | 6.8 | 0.1 | 5.9 | 0.1 | 3.1 |
| 0.15 | 5.9 | 0.15 | 7.7 | 0.15 | 5.8 | 0.15 | 6.8 | 0.15 | 5.8 | 0.15 | 3.1 |
| 0.2 | 5.9 | 0.2 | 7.7 | 0.2 | 5.8 | 0.2 | 6.8 | 0.2 | 5.8 | 0.2 | 3.1 |
| 0.25 | 5.9 | 0.25 | 7.6 | 0.25 | 5.8 | 0.25 | 6.8 | 0.25 | 5.8 | 0.25 | 3.1 |
| 0.3 | 5.9 | 0.3 | 7.6 | 0.3 | 5.8 | 0.5 | 6.8 | 0.3 | 5.8 | 0.3 | 3.1 |
| 0.35 | 5.9 | 0.35 | 7.6 | 0.35 | 5.8 | 0.35 | 6.8 | 0.35 | 5.8 | 0.35 | 3.1 |
| 0.4 | 5.9 | 0.4 | 7.6 | 0.4 | 5.8 | 0.4 | 6.7 | 0.4 | 5.8 | 0.4 | 3.1 |
| 0.45 | 5.9 | 0.45 | 7.6 | 0.45 | 5.8 | 0.45 | 6.7 | 0.45 | 5.8 | 0.45 | 3.1 |
| 0.5 | 5.9 | 0.5 | 7.7 | 0.5 | 5.8 | 0.5 | 6.7 | 0.5 | 5.8 | 0.5 | 3.1 |
| 0.55 | 5.9 | 0.55 | 7.7 | 0.55 | 5.8 | 0.55 | 6.7 | 0.55 | 5.7 | 0.55 | 3.1 |
| 0.6 | 5.9 | 0.6 | 7.7 | 0.6 | 5.8 | 0.6 | 6.7 | 0.6 | 5.7 | 0.6 | 3.1 |
| 0.65 | 5.9 | 0.65 | 7.7 | 0.65 | 5.8 | 0.65 | 6.6 | 0.65 | 5.6 | 0.65 | 3.1 |
| 0.7 | 5.9 | 0.7 | 7.6 | 0.7 | 5.8 | 0.7 | 6.5 | 0.7 | 5.4 | 0.7 | 3.1 |
| 0.75 | 5.7 | 0.75 | 7.5 | 0.75 | 5.8 | 0.75 | 6.4 | 0.75 | 5.2 | 0.75 | 3.1 |
| 0.8 | 5.5 | 0.3 | 7.2 | 0.8 | 5.8 | 0.8 | 6.1 | 0.8 | 4.3 | 0.8 | 2.9 |
| 0.85 | 5.0 | 0.85 | 6.6 | 0.85 | 5.8 | 0.85 | 5.8 | 0.85 | 4.3 | 0.85 | 2.7 |
| 0.9 | 4.3 | 0.9 | 5.5 | 0.9 | 5.0 | 0.9 | 4.8 | 0.9 | 3.6 | 0.9 | 2.4 |
| 0.95 | 3.0 | 0.95 | 3.0 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFO-1234yf-HFC-245cb-HFO-1234zeE-HCFO-1233zdE-HFO-1243zf

| Organics 0.2 F1234yf + 0.2 F245cb + 0.2 F1243zf + 0.2 F1234zeE + 0.2 F1233zdE | | Organics 0.96 F1234yf + 0.01 F245cb + 0.01 F1243zf + 0.01 F1234zeE + 0.01 F1233zdE | | Organics 0.01 F1234yf + 0.96 F245cb + 0.01 F1243zf + 0.01 F1234zeE + 0.01 F1233zdE | | Organics 0.01 F1234yf + 0.01 F245cb + 0.96 F1243zf + 0.01 F1234zeE + 0.01 F1233zdE | | Organics 0.01 F1234yf + 0.01 F245cb + 0.01 F1243zf + 0.96 F1234zeE + 0.01 F1233zdE | | Organics 0.01 F1234yf + 0.01 F245cb + 0.01 F1243zf + 0.01 F1234zeE + 0.96 F1233zdE | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.8 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.8 |
| 0.4 | 5.9 | 0.4 | 7.7 | 0.4 | 5.8 | 0.4 | 6.7 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.5 |
| 0.55 | 5.0 | 0.85 | 6.6 | 0.85 | 5.8 | 0.85 | 5.8 | 0.85 | 4.3 | 0.85 | 2.3 |
| 0.9 | 4.2 | 0.9 | 5.5 | 0.9 | 5.0 | 0.9 | 4.8 | 0.9 | 3.6 | 0.9 | 2.1 |
| 0.95 | 3.0 | 0.95 | 3.8 | 0.95 | 3.5 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF-HFO-1234yf-HFC-245th-HFO-1234zeZ-HCFO-1233zdE-HFO-1243zf

| Organics 0.2 F1234yf + 0.2 F245cb + 0.2 F1243zf + 0.2 F1234zeZ + 0.2 F1233zdE | | Organics 0.96 F1234yf + 0.01 F245cb + 0.01 F1243zf + 0.01 F1234zeZ + 0.01 F1233zdE | | Organics 0.01 F1234yf + 0.01 F245cb + 0.01 F1243zf + 0.01 F1234zeZ + 0.96 F1233zdE | | Organics 0.01 F1234yf + 0.01 F245cb + 0.96 F1243zf + 0.01 F1234zeZ + 0.01 F1233zdE | | Organics 0.01 F1234yf + 0.01 F245cb + 0.01 F1243zf + 0.96 F1234zeZ + 0.01 F1233zdE | | Organics 0.01 F1234yf + 0.01 F245cb + 0.01 F1243zf + 0.01 F1234zeZ + 0.96 F1233zdE | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.6 |
| 0.8 | 5.0 | 0.8 | 7.2 | 0.8 | 5.8 | 0.8 | 6.1 | 0.8 | 2.9 | 0.8 | 2.5 |
| 0.85 | 4.6 | 0.85 | 6.6 | 0.85 | 5.8 | 0.85 | 5.6 | 0.85 | 2.7 | 0.85 | 2.3 |
| 0.9 | 3.9 | 0.9 | 5.5 | 0.9 | 5.0 | 0.9 | 4.7 | 0.9 | 2.4 | 0.9 | 2.0 |
| 0.95 | 2.9 | 0.95 | 3.8 | 0.95 | 3.5 | 0.95 | 3.4 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF-HFO-1234yf-HFO-1234zeE-HFO-1234zeZ-HCFO-1233zdE-HFO-1243zf

| Organics 0.2 F1234yf + 0.2 F1243zf + 0.2 F1233zdE + 0.2 F1234zeE + 0.2 F1234zeZ | | Organics 0.96 F1234yf + 0.01 F1243zf + 0.01 F1233zdE + 0.01 F1234zeE + 0.01 F1234zeZ | | Organics 0.01 F1234yf + 0.96 F1243zf + 0.01 F1233zdE + 0.01 F1234zeE + 0.01 F1234zeZ | | Organics 0.01 F1234yf + 0.01 F1243zf + 0.96 F1233zdE + 0.01 F1234zeE + 0.01 F1234zeZ | | Organics 0.01 F1234yf + 0.01 F1243zf + 0.01 F1233zdE + 0.96 F1234zeE + 0.01 F1234zeZ | | Organics 0.01 F1234yf + 0.01 F1243zf + 0.01 F1233zdE + 0.01 F1234zeE + 0.96 F1234zeZ | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.2 | 0 | 6.7 | 0 | 5.8 | 0 | 1.5 | 0 | 4.8 | 0 | 1.9 |
| 0.05 | 5.3 | 0.05 | 7.6 | 0.05 | 6.7 | 0.05 | 2.6 | 0.05 | 5.8 | 0.05 | 3.0 |
| 0.1 | 5.3 | 0.1 | 7.6 | 0.1 | 6.7 | 0.1 | 2.6 | 0.1 | 5.8 | 0.1 | 3.0 |
| 0.15 | 5.3 | 0.15 | 7.6 | 0.15 | 8.7 | 0.15 | 2.6 | 0.15 | 5.8 | 0.15 | 3.0 |
| 0.2 | 5.3 | 0.2 | 7.6 | 0.2 | 6.7 | 0.2 | 2.6 | 0.2 | 5.8 | 0.2 | 3.0 |
| 0.25 | 5.3 | 0.25 | 7.6 | 0.25 | 6.7 | 0.25 | 2.6 | 0.25 | 5.8 | 0.25 | 3.0 |
| 0.3 | 5.3 | 0.3 | 7.6 | 0.3 | 6.7 | 0.3 | 2.6 | 0.3 | 5.8 | 0.3 | 3.0 |
| 0.35 | 5.3 | 0.35 | 7.6 | 0.35 | 6.7 | 0.35 | 2.6 | 0.35 | 5.8 | 0.35 | 3.0 |
| 0.4 | 5.3 | 0.4 | 7.6 | 0.4 | 6.7 | 0.4 | 2.6 | 0.4 | 5.8 | 0.4 | 3.0 |
| 0.45 | 5.3 | 0.45 | 7.6 | 0.45 | 6.7 | 0.45 | 2.6 | 0.45 | 5.8 | 0.45 | 3.0 |
| 0.5 | 5.3 | 0.5 | 7.6 | 0.5 | 6.7 | 0.5 | 2.6 | 0.5 | 5.8 | 0.5 | 3.0 |
| 0.55 | 5.2 | 0.55 | 7.6 | 0.55 | 6.7 | 0.55 | 2.6 | 0.55 | 5.7 | 0.55 | 3.0 |
| 0.6 | 5.2 | 0.6 | 7.6 | 0.6 | 6.7 | 0.6 | 2.6 | 0.6 | 5.6 | 0.6 | 3.0 |
| 0.65 | 5.2 | 0.65 | 7.6 | 0.65 | 6.6 | 0.65 | 2.6 | 0.65 | 5.5 | 0.65 | 3.0 |
| 0.7 | 5.2 | 0.7 | 7.6 | 0.7 | 6.5 | 0.7 | 2.6 | 0.7 | 5.4 | 0.7 | 3.0 |
| 0.75 | 5.0 | 0.75 | 7.5 | 0.75 | 6.3 | 0.75 | 2.6 | 0.75 | 5.1 | 0.75 | 3.0 |
| 0.8 | 4.7 | 0.8 | 7.1 | 0.8 | 6.1 | 0.8 | 2.5 | 0.8 | 4.8 | 0.8 | 2.9 |
| 0.85 | 4.3 | 0.80 | 6.5 | 0.85 | 5.6 | 0.85 | 2.3 | 0.85 | 4.3 | 0.85 | 2.7 |
| 0.9 | 3.7 | 0.9 | 5.5 | 0.9 | 4.7 | 0.9 | 2.0 | 0.9 | 3.6 | 0.9 | 2.4 |
| 0.95 | 2.7 | 0.95 | 3.8 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF-HFC-245cb-HFO-1234zeE-HFO-1234zeZ-HCFO-1233zdE-HFO-1243zf

| Organics 0.2 F245cb + 0.2 F1243zf + 0.2 F1233zdE + 0.2 F1234zeE + 0.2 F1234zeZ | | Organics 0.96 F245cb + 0.01 F1243zf + 0.01 F1233zdE + 0.01 F1234zeE + 0.01 F1234zeZ | | Organics 0.01 F245cb + 0.96 F1243zf + 0.01 F1233zdE + 0.01 F1234zeE + 0.01 F1234zeZ | | Organics 0.01 F245cb + 0.01 F1243zf + 0.96 F1233zdE + 0.01 F1234zeE + 0.01 F1234zeZ | | Organics 0.01 F245cb + 0.01 F1243zf + 0.01 F1233zdE + 0.96 F1234zeE + 0.01 F1234zeZ | | Organics 0.01 F245cb + 0.01 F1243zf + 0.01 F1233zdE + 0.01 F1234zeE + 0.96 F1234zeZ | |
|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.8 | 0 | 4.6 | 0 | 5.8 | 0 | 1.5 | 0 | 4.8 | 0 | 1.9 |
| 0.05 | 4.9 | 0.05 | 5.8 | 0.05 | 6.7 | 0.05 | 2.6 | 0.05 | 5.8 | 0.05 | 3.0 |
| 0.1 | 4.9 | 0.1 | 5.8 | 0.1 | 6.7 | 0.1 | 2.6 | 0.1 | 5.8 | 0.1 | 3.0 |
| 0.15 | 4.9 | 0.15 | 5.8 | 0.15 | 6.7 | 0.15 | 2.6 | 0.15 | 5.8 | 0.15 | 3.0 |
| 0.2 | 4.9 | 0.2 | 5.8 | 0.2 | 6.7 | 0.2 | 2.6 | 0.2 | 5.8 | 0.2 | 3.0 |
| 0.25 | 4.9 | 0.25 | 5.8 | 0.25 | 6.7 | 0.25 | 2.6 | 0.25 | 5.8 | 0.25 | 3.0 |
| 0.3 | 4.9 | 0.3 | 5.8 | 0.3 | 6.7 | 0.3 | 2.6 | 0.3 | 5.8 | 0.3 | 3.0 |
| 0.35 | 4.9 | 0.35 | 5.8 | 0.35 | 6.7 | 0.35 | 2.6 | 0.35 | 5.8 | 0.35 | 3.0 |
| 0.4 | 4.9 | 0.4 | 5.8 | 0.4 | 6.7 | 0.4 | 2.6 | 0.4 | 5.8 | 0.4 | 3.0 |
| 0.45 | 4.9 | 0.45 | 5.8 | 0.45 | 6.7 | 0.45 | 2.6 | 0.45 | 5.8 | 0.45 | 3.0 |
| 0.5 | 4.9 | 0.5 | 5.8 | 0.5 | 6.7 | 0.5 | 2.6 | 0.5 | 5.7 | 0.5 | 3.0 |
| 0.55 | 4.9 | 0.55 | 5.8 | 0.55 | 6.7 | 0.55 | 2.6 | 0.55 | 5.7 | 0.55 | 3.0 |
| 0.6 | 4.9 | 0.6 | 5.8 | 0.6 | 6.6 | 0.6 | 2.6 | 0.6 | 5.6 | 0.6 | 3.0 |
| 0.65 | 4.9 | 0.65 | 5.8 | 0.65 | 6.6 | 0.65 | 2.6 | 0.65 | 5.5 | 0.65 | 3.0 |
| 0.7 | 4.9 | 0.7 | 5.8 | 0.7 | 6.5 | 0.7 | 2.6 | 0.7 | 5.4 | 0.7 | 3.0 |
| 0.75 | 4.8 | 0.75 | 5.8 | 0.75 | 6.3 | 0.75 | 2.6 | 0.75 | 5.1 | 0.75 | 3.0 |
| 0.8 | 4.5 | 0.8 | 5.8 | 0.8 | 6.0 | 0.8 | 2.4 | 0.8 | 4.8 | 0.8 | 2.9 |
| 0.85 | 4.2 | 0.85 | 5.0 | 0.85 | 5.6 | 0.85 | 2.3 | 0.85 | 4.3 | 0.85 | 2.7 |
| 0.9 | 3.5 | 0.9 | 5.0 | 0.9 | 4.7 | 0.9 | 2.0 | 0.9 | 3.6 | 0.9 | 2.4 |
| 0.95 | 2.6 | 0.95 | 3.5 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

EXAMPLE 11: TEMPERATURE AND PRESSURE RANGE OF SYSTEMS WITH 6 COMPOUNDS

| | Boiling point range | |
|---|---|---|
| System with 6 compounds | Temperature ° C. | Pressure bar abs |
| HF-HCFO-1233xf-HFO-1234yf-HFC-245cb-HFO-1234zeE-HFO-1243zf | 0 to 40 | ~1.0 to ~11.6 |
| HF-HCFO-1233xf-HFO-1234yf-HFC-245cb-HFO-1234zeZ-HFO-1243zf | 0 to 40 | ~1.0 to ~11.6 |
| HF-HCFO-1233xf-HFO-1234yf-HFC-245cb-HCFO-1233zdE-HFO-1243zf | 0 to 40 | ~0.9 to ~11.6 |
| HF-HCFO-1233xf-HFO-1234yf-HFO-1234zeE-HFO-1234zeZ-HFO-1243zf | 0 to 40 | ~1.0 to ~11.6 |
| HF-HCFO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HCFO-1233xf-HFC-245cb-HFO-1234zeE-HFO-1234zeZ-HFO-1243zf | 0 to 40 | ~1.0 to ~10.3 |
| HF-HCFO-1233xf-HFC-245cb-HFO-1234zeE-HCFO-1233zdE-HFO-1243zf | 0 to 40 | ~0.9 to ~10.3 |
| HF-HCFO-1233xf-HFC-245cb-HFO-1234zeZ-HCFO-1233zdE-HFO-1243zf | 0 to 40 | ~1.0 to ~10.3 |
| HF-HCFO-1233xf-HFO-1234zeE-HFO-1234zeZ-HCFO-1233zdE-HFO-1243zf | 0 to 40 | ~0.9 to ~10.3 |
| HF-HFO-1234yf-HFC-245cb-HFO-1234zeE-HFO-1234zeZ-HFO-1243zf | 0 to 40 | ~1.2 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |
| HF-HFC-245cb-HFO-1234zeE-HFO-1234zeZ-HCFO-1233zdE-HFO-1243zf | 0 to 40 | ~0.9 to ~10.3 |

EXAMPLE 12: DECANTATION RANGE OF SYSTEMS WITH 6 COMPOUNDS

| | Decantation ranges Mass percentage of HF | | |
|---|---|---|---|
| System with 6 compounds | Isotherm 0° C. | Isotherm 25° C. | Isotherm 40° C. |
| HF-HCFO-1233xf-HFO-1234yf-HFC-245cb-HFO-1234zeE-HFO-1243zf | 5-75 | 10-65 | * |
| HF-HCFO-1233xf-HFO-1234yf-HFC-245cb-HFO-1234zeZ-HFO-1243zf | 5-75 | 10-70 | 15-50 |
| HF-HCFO-1233xf-HFO-1234yf-HFC-245cb-HCFO-1233zdE-HFO-1243zf | 5-75 | 5-70 | 15-55 |
| HF-HCFO-1233xf-HFO-1234yf-HFO-1234zeE-HFO-1234zeZ-HFO-1243zf | 5-70 | 10-65 | * |
| HF-HCFO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HCFO-1233xf-HFC-245cb-HFO-1234zeE-HFO-1234zeZ-HFO-1243zf | 5-75 | 10-70 | 15-45 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |

-continued

| System with 6 compounds | Decantation ranges Mass percentage of HF | | |
|---|---|---|---|
| | Isotherm 0° C. | Isotherm 25° C. | Isotherm 40° C. |
| HF-HCFO-1233xf-HFO-1234zeE-HFO-1234zeZ-HCFO-1233zdE-HFO-1243zf | 5-75 | 5-65 | 10-55 |
| HF-HFO-1234yf-HFC-245cb-HFO-1234zeE-HFO-1234zeZ-HFO-1243zf | 5-75 | 10-65 | * |
| HF-HFO-1234yf-HFC-245cb-HFO-1234zeE-HCFO-1233zdE-HFO-1243zf | 5-75 | 10-65 | * |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |

| System with 6 compounds | Decantation ranges Mass percentage of HF | | |
|---|---|---|---|
| | Isotherm 0° C. | Isotherm 25° C. | Isotherm 40° C. |
| HF-HFC-245cb-HFO-1234zeE-HFO-1234zeZ-HCFO-1233zdE-HFO-1243zf | 5-75 | 5-70 | 15-50 |

EXAMPLE 13: SYSTEMS WITH SEVEN COMPOUNDS, ISOTHERM AT 25° C.

HF-HCFO-1233xf-HFC-245cb-HCFO-1233zdE-HFO-1234zeE-HFO-1234zeZ-HFO-1243zf

| Organics 0.15 F1233xf + 0.17 F245cb + 0.17 F1233zdE + 0.17 F1234zeE + 0.17 F1234zeZ + 0.17 F1243zf | | Organics 0.95 F1233xf + 0.01 F245cb + 0.01 F1233zdE + 0.01 F1234zeE + 0.01 F1234zeZ + 0.01 F1243zf | | Organics 0.01 F1233xf + 0.95 F245cb + 0.01 F1233zdE + 0.01 F1234zeE + 0.01 F1234zeZ + 0.01 F1243zf | | Organics 0.01 F1233xf + 0.01 F245cb + 0.95 F1233zdE + 0.01 F1234zeE + 0.01 F1234zeZ + 0.01 F1243zf | | Organics 0.01 F1233xf + 0.01 F245cb + 0.01 F1233zdE + 0.95 F1234zeE + 0.01 F1234zeZ + 0.01 F1243zf | | Organics 0.01 F1233xf + 0.01 F245cb + 0.01 F1233zdE + 0.01 F1234zeE + 0.01 F1234zeZ + 0.95 F1243zf | | Organics 0.01 F1233xf + 0.01 F245cb + 0.01 F1233zdE + 0.01 F1234zeE + 0.95 F1234zeZ + 0.01 F1243zf | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.5 | 0 | 1.7 | 0 | 4.5 | 0 | 1.5 | 0 | 4.8 | 0 | 5.7 | 0 | 1.9 |
| 0.05 | 4.6 | 0.05 | 2.8 | 0.05 | 5.7 | 0.05 | 2.6 | 0.05 | 5.7 | 0.05 | 6.7 | 0.05 | 3.0 |
| 0.1 | 4.6 | 0.1 | 2.8 | 0.1 | 5.7 | 0.1 | 2.6 | 0.1 | 5.8 | 0.1 | 6.7 | 0.1 | 3.0 |
| 0.15 | 4.6 | 0.15 | 2.8 | 0.15 | 5.7 | 0.15 | 2.6 | 0.15 | 5.8 | 0.15 | 6.7 | 0.15 | 3.0 |
| 0.2 | 4.6 | 0.2 | 2.8 | 0.2 | 5.7 | 0.2 | 2.6 | 0.2 | 5.8 | 0.2 | 6.7 | 0.2 | 3.0 |
| 0.25 | 4.6 | 0.25 | 2.8 | 0.25 | 5.8 | 0.25 | 2.6 | 0.25 | 5.8 | 0.25 | 6.7 | 0.25 | 3.0 |
| 0.3 | 4.6 | 0.3 | 2.8 | 0.3 | 5.8 | 0.3 | 2.6 | 0.3 | 5.8 | 0.3 | 6.7 | 0.3 | 3.0 |
| 0.35 | 4.6 | 0.35 | 2.8 | 0.35 | 5.8 | 0.35 | 2.6 | 0.35 | 5.8 | 0.35 | 6.7 | 0.35 | 3.0 |
| 0.4 | 4.6 | 0.4 | 2.8 | 0.4 | 5.8 | 0.4 | 2.6 | 0.4 | 5.8 | 0.4 | 6.7 | 0.4 | 3.0 |
| 0.45 | 4.6 | 0.45 | 2.8 | 0.45 | 5.8 | 0.45 | 2.6 | 0.45 | 5.7 | 0.45 | 6.7 | 0.45 | 3.0 |
| 0.5 | 4.6 | 0.5 | 2.8 | 0.5 | 5.8 | 0.5 | 2.6 | 0.5 | 5.7 | 0.5 | 6.7 | 0.5 | 3.0 |
| 0.55 | 4.6 | 0.55 | 2.8 | 0.55 | 5.8 | 0.55 | 2.6 | 0.55 | 5.7 | 0.55 | 6.6 | 0.55 | 3.0 |
| 0.5 | 4.6 | 0.6 | 2.8 | 0.6 | 5.8 | 0.6 | 2.6 | 0.6 | 5.6 | 0.6 | 6.6 | 0.6 | 3.0 |
| 0.65 | 4.6 | 0.55 | 2.8 | 0.65 | 5.8 | 0.65 | 2.6 | 0.65 | 5.5 | 0.65 | 6.6 | 0.65 | 3.0 |
| 0.7 | 4.6 | 0.7 | 2.8 | 0.7 | 5.8 | 0.7 | 2.6 | 0.7 | 5.3 | 0.7 | 6.6 | 0.7 | 3.0 |
| 0.75 | 4.5 | 0.75 | 2.8 | 0.75 | 5.8 | 0.75 | 2.6 | 0.75 | 5.1 | 0.75 | 6.2 | 0.75 | 3.0 |
| 0.8 | 4.2 | 0.8 | 2.6 | 0.8 | 5.8 | 0.8 | 2.4 | 0.8 | 4.8 | 0.8 | 6.0 | 0.8 | 2.9 |
| 0.85 | 3.9 | 0.85 | 2.4 | 0.85 | 5.8 | 0.85 | 2.3 | 0.85 | 4.3 | 0.85 | 5.5 | 0.85 | 2.7 |
| 0.9 | 3.3 | 0.9 | 2.2 | 0.9 | 4.9 | 0.9 | 2.0 | 0.9 | 3.6 | 0.9 | 4.7 | 0.9 | 2.4 |
| 0.95 | 2.5 | 0.95 | 1.8 | 0.95 | 3.5 | 0.95 | 1.7 | 0.95 | 2.6 | 0.95 | 3.3 | 0.95 | 1.9 |
| 1 | 1.2 | 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HCFO-1233zdE-HFO-1234zeE-HFO-1243zf

| Organics 0.15 F1233xf + 0.17 F1234yf + 0.17 F245cb + 0.17 F1233zdE + 0.17 F1234zeE + 0.17 F1243zf | | Organics 0.01 F1233xf + 0.95 F1234yf + 0.01 F245cb + 0.01 F1233zdE + 0.01 F1234zeE + 0.01 F1243zf | | Organics 0.01 F1233xf + 0.01 F1234yf + 0.95 F245cb + 0.01 F1233zdE + 0.01 F1234zeE + 0.01 F1243zf | | Organics 0.01 F1233xf + 0.01 F1234yf + 0.01 F245cb + 0.95 F1233zdE + 0.01 F1234zeE + 0.01 F1243zf | | Organics 0.01 F1233xf + 0.01 F1234yf + 0.01 F245cb + 0.01 F1233zdE + 0.95 F1234zeE + 0.01 F1243zf | | Organics 0.01 F1233xf + 0.01 F1234yf + 0.01 F245cb + 0.01 F1233zdE + 0.01 F1234zeE + 0.95 F1243zf | | Organics 0.95 F1233xf + 0.01 F1234yf + 0.01 F245cb + 0.01 F1233zdE + 0.01 F1234zeE + 0.01 F1243zf | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.4 | 0 | 6.6 | 0 | 4.6 | 0 | 1.5 | 0 | 4.8 | 0 | 5.8 | 0 | 1.7 |
| 0.05 | 5.4 | 0.05 | 7.6 | 0.05 | 5.8 | 0.05 | 2.6 | 0.05 | 5.8 | 0.05 | 6.7 | 0.05 | 2.8 |
| 0.1 | 5.4 | 0.1 | 7.6 | 0.1 | 5.8 | 0.1 | 2.6 | 0.1 | 5.8 | 0.1 | 6.7 | 0.1 | 2.8 |
| 0.15 | 5.4 | 0.15 | 7.6 | 0.15 | 5.8 | 0.15 | 2.6 | 0.15 | 5.8 | 0.15 | 6.7 | 0.15 | 2.8 |
| 0.2 | 5.4 | 0.2 | 7.6 | 0.2 | 5.8 | 0.2 | 2.6 | 0.2 | 5.8 | 0.2 | 6.7 | 0.2 | 2.8 |
| 0.25 | 5.4 | 0.25 | 7.6 | 0.25 | 5.8 | 0.25 | 2.6 | 0.25 | 5.8 | 0.25 | 6.7 | 0.25 | 2.8 |

-continued

| Organics 0.15 F1233xf + 0.17 F1234yf + 0.17 F245cb + 0.17 F1233zdE + 0.17 F1234zeE + 0.17 F1243zf | | Organics 0.01 F1233xf + 0.95 F1234yf + 0.01 F245cb + 0.01 F1233zdE + 0.01 F1234zeE + 0.01 F1243zf | | Organics 0.01 F1233xf + 0.01 F1234yf + 0.95 F245cb + 0.01 F1233zdE + 0.01 F1234zeE + 0.01 F1243zf | | Organics 0.01 F1233xf + 0.01 F1234yf + 0.01 F245cb + 0.95 F1233zdE + 0.01 F1234zeE + 0.01 F1243zf | | Organics 0.01 F1233xf + 0.01 F1234yf + 0.01 F245cb + 0.01 F1233zdE + 0.95 F1234zeE + 0.01 F1243zf | | Organics 0.01 F1233xf + 0.01 F1234yf + 0.01 F245cb + 0.01 F1233zdE + 0.01 F1234zeE + 0.95 F1243zf | | Organics 0.95 F1233xf + 0.01 F1234yf + 0.01 F245cb + 0.01 F1233zdE + 0.01 F1234zeE + 0.01 F1243zf | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0.3 | 5.4 | 0.3 | 7.6 | 0.3 | 5.8 | 0.3 | 2.6 | 0.3 | 5.8 | 0.3 | 6.7 | 0.3 | 2.8 |
| 0.35 | 5.4 | 0.35 | 7.6 | 0.35 | 5.8 | 0.35 | 2.6 | 0.35 | 5.8 | 0.35 | 6.7 | 0.35 | 2.8 |
| 0.4 | 5.4 | 0.4 | 7.6 | 0.4 | 5.8 | 0.4 | 2.6 | 0.4 | 5.8 | 0.4 | 6.7 | 0.4 | 2.8 |
| 0.45 | 5.4 | 0.45 | 7.6 | 0.45 | 5.8 | 0.45 | 2.6 | 0.45 | 5.8 | 0.45 | 6.7 | 0.45 | 2.8 |
| 0.5 | 5.4 | 0.5 | 7.6 | 0.5 | 5.8 | 0.5 | 2.6 | 0.5 | 5.8 | 0.5 | 6.7 | 0.5 | 2.8 |
| 0.55 | 5.4 | 0.55 | 7.6 | 0.55 | 5.8 | 0.55 | 2.6 | 0.55 | 5.7 | 0.55 | 6.7 | 0.55 | 2.8 |
| 0.6 | 5.4 | 0.6 | 7.6 | 0.6 | 5.8 | 0.6 | 2.6 | 0.6 | 5.6 | 0.6 | 6.7 | 0.6 | 2.8 |
| 0.65 | 5.4 | 0.65 | 7.6 | 0.65 | 5.8 | 0.65 | 2.6 | 0.65 | 5.5 | 0.65 | 6.6 | 0.65 | 2.8 |
| 0.7 | 5.4 | 0.7 | 7.6 | 0.7 | 5.8 | 0.7 | 2.6 | 0.7 | 5.4 | 0.7 | 6.5 | 0.7 | 2.8 |
| 0.75 | 5.3 | 0.75 | 7.4 | 0.75 | 5.8 | 0.75 | 2.6 | 0.75 | 5.1 | 0.75 | 6.3 | 0.75 | 2.8 |
| 0.8 | 5.0 | 0.8 | 7.1 | 0.8 | 5.8 | 0.8 | 2.5 | 0.8 | 4.8 | 0.8 | 6.1 | 0.8 | 2.7 |
| 0.85 | 4.6 | 0.85 | 6.5 | 0.85 | 5.8 | 0.85 | 2.3 | 0.85 | 4.3 | 0.85 | 5.6 | 0.85 | 2.5 |
| 0.9 | 3.9 | 0.9 | 5.5 | 0.9 | 5.0 | 0.9 | 2.1 | 0.9 | 3.6 | 0.9 | 4.7 | 0.9 | 2.2 |
| 0.95 | 2.8 | 0.95 | 3.8 | 0.95 | 3.5 | 0.95 | 1.7 | 0.95 | 2.6 | 0.95 | 3.4 | 0.95 | 1.8 |
| 1 | 1.2 | 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HCFO-1233zdE-HFO-1234zeZ-HFO-1243zf

| Organics 0.15 F1233xf + 0.17 F1234yf + 0.17 F245cb + 0.17 F1243zf + 0.17 F1233zdE + 0.17 F1234zeZ | | Organics 0.01 F1233xf + 0.95 F1234yf + 0.01 F245cb + 0.01 F1243zf + 0.01 F1233zdE + 0.01 F1234zeZ | | Organics 0.01 F1233xf + 0.01 F1234yf + 0.95 F245cb + 0.01 F1243zf + 0.01 F1233zdE + 0.01 F1234zeZ | | Organics 0.01 F1233xf + 0.01 F1234yf + 0.01 F245cb + 0.95 F1243zf + 0.01 F1233zdE + 0.01 F1234zeZ | | Organics 0.01 F1233xf + 0.01 F1234yf + 0.01 F245cb + 0.01 F1243zf + 0.95 F1233zdE + 0.01 F1234zeZ | | Organics 0.01 F1233xf + 0.01 F1234yf + 0.01 F245cb + 0.01 F1243zf + 0.01 F1233zdE + 0.95 F1234zeZ | | Organics 0.95 F1233xf + 0.01 F1234yf + 0.01 F245cb + 0.01 F1243zf + 0.01 F1233zdE + 0.01 F1234zeZ | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.8 | 0 | 6.6 | 0 | 4.6 | 0 | 5.7 | 0 | 1.5 | 0 | 1.9 | 0 | 1.7 |
| 0.05 | 4.9 | 0.05 | 7.6 | 0.05 | 5.8 | 0.05 | 6.7 | 0.05 | 2.6 | 0.05 | 3.0 | 0.05 | 2.8 |
| 0.1 | 4.9 | 0.1 | 7.6 | 0.1 | 5.8 | 0.1 | 6.7 | 0.1 | 2.6 | 0.1 | 3.0 | 0.1 | 2.8 |
| 0.15 | 4.9 | 0.15 | 7.6 | 0.15 | 5.8 | 0.15 | 6.7 | 0.15 | 2.6 | 0.15 | 3.0 | 0.15 | 2.8 |
| 0.2 | 4.9 | 0.2 | 7.6 | 0.2 | 5.8 | 0.2 | 6.7 | 0.2 | 2.6 | 0.2 | 3.0 | 0.2 | 2.8 |
| 0.25 | 4.9 | 0.25 | 7.6 | 0.25 | 5.8 | 0.25 | 6.7 | 0.25 | 2.6 | 0.25 | 3.0 | 0.25 | 2.8 |
| 0.3 | 4.9 | 0.3 | 7.6 | 0.3 | 5.8 | 0.3 | 6.7 | 0.3 | 2.6 | 0.3 | 3.0 | 0.3 | 2.8 |
| 0.35 | 4.9 | 0.35 | 7.6 | 0.35 | 5.8 | 0.35 | 6.7 | 0.35 | 2.6 | 0.35 | 3.0 | 0.35 | 2.8 |
| 0.4 | 4.9 | 0.4 | 7.6 | 0.4 | 5.8 | 0.4 | 6.7 | 0.4 | 2.6 | 0.4 | 3.0 | 0.4 | 2.8 |
| 0.45 | 4.9 | 0.45 | 7.6 | 0.45 | 5.8 | 0.45 | 6.7 | 0.45 | 2.6 | 0.45 | 3.0 | 0.45 | 2.8 |
| 0.5 | 4.9 | 0.5 | 7.6 | 0.5 | 5.8 | 0.5 | 6.7 | 0.5 | 2.6 | 0.5 | 3.0 | 0.5 | 2.8 |
| 0.55 | 4.9 | 0.55 | 7.6 | 0.55 | 5.3 | 0.55 | 6.7 | 0.55 | 2.6 | 0.55 | 3.0 | 0.55 | 2.8 |
| 0.6 | 4.9 | 0.6 | 7.6 | 0.6 | 5.8 | 0.6 | 6.6 | 0.6 | 2.6 | 0.6 | 3.0 | 0.6 | 2.8 |
| 0.65 | 4.9 | 0.65 | 7.6 | 0.65 | 5.8 | 0.65 | 6.6 | 0.65 | 2.6 | 0.65 | 3.0 | 0.65 | 2.8 |
| 0.7 | 4.9 | 0.7 | 7.6 | 0.7 | 5.8 | 0.7 | 6.5 | 0.7 | 2.6 | 0.7 | 3.0 | 0.7 | 2.8 |
| 0.75 | 4.9 | 0.75 | 7.4 | 0.75 | 5.8 | 0.75 | 6.3 | 0.75 | 2.6 | 0.75 | 3.0 | 0.75 | 2.8 |
| 0.8 | 4.7 | 0.8 | 7.1 | 0.8 | 5.8 | 0.8 | 6.0 | 0.8 | 2.5 | 0.8 | 2.9 | 0.8 | 2.7 |
| 0.85 | 4.3 | 0.85 | 6.5 | 0.85 | 5.8 | 0.85 | 5.5 | 0.85 | 2.3 | 0.85 | 2.7 | 0.85 | 2.5 |
| 0.9 | 3.7 | 0.9 | 5.5 | 0.9 | 5.0 | 0.9 | 4.7 | 0.9 | 2.0 | 0.9 | 2.4 | 0.9 | 2.2 |
| 0.95 | 2.7 | 0.95 | 3.8 | 0.95 | 3.5 | 0.95 | 3.3 | 0.95 | 1.7 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF-HCFO-1233xf-HFO-1234yf-HFC-245cb-HFO-
1234zeE-HFO-1234zeZ-HFO-1243zf

| Organics 0.15 F1233xf + 0.17 F1234yf + 0.17 F245cb + 0.17 F1243zf + 0.17 F1234zeE + 0.17 F1234zeZ | | Organics 0.01 F1233xf + 0.95 F1234yf + 0.01 F243cb + 0.01 F1243zf + 0.01 F1234zeE + 0.01 F1234zeZ | | Organics 0.01 F1233xf + 0.01 F1234yf + 0.95 F245cb + 0.01 F1243zf + 0.01 F1234zeE + 0.01 F1234zeZ | | Organics 0.01 F1233xf + 0.01 F1234yf + 0.01 F245cb + 0.95 F1243zf + 0.01 F1234zeE + 0.01 F1234zeZ | | Organics 0.01 F1233xf + 0.01 F1234yf + 0.01 F245cb + 0.01 F1243zf + 0.95 F1234zeE + 0.01 F1234zeZ | | Organics 0.01 F1233xf + 0.01 F1234yf + 0.01 F245cb + 0.01 F1243zf + 0.01 F1234zeE + 0.95 F1234zeZ | | Organics 0.95 F1233xf + 0.01 F1234yf + 0.01 F245cb + 0.01 F1243zf + 0.01 F1234zeE + 0.01 F1234zeZ | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.4 | 0 | 6.5 | 0 | 4.6 | 0 | 5.8 | 0 | 4.8 | 0 | 2.0 | 0 | 1.7 |
| 0.05 | 5.5 | 0.05 | 7.6 | 0.05 | 5.8 | 0.05 | 6.7 | 0.05 | 5.8 | 0.05 | 3.1 | 0.05 | 2.8 |
| 0.1 | 5.5 | 0.1 | 7.6 | 0.1 | 5.8 | 0.1 | 6.7 | 0.1 | 5.8 | 0.1 | 3.1 | 0.1 | 2.8 |
| 0.15 | 5.5 | 0.15 | 7.6 | 0.15 | 5.8 | 0.15 | 6.7 | 0.15 | 5.8 | 0.15 | 3.1 | 0.15 | 2.8 |
| 0.2 | 5.5 | 0.2 | 7.6 | 0.2 | 5.8 | 0.2 | 6.7 | 0.2 | 5.8 | 0.2 | 3.1 | 0.2 | 2.8 |
| 0.25 | 5.5 | 0.25 | 7.6 | 0.25 | 5.8 | 0.25 | 6.7 | 0.25 | 5.8 | 0.25 | 3.1 | 0.25 | 2.8 |
| 0.3 | 5.5 | 0.3 | 7.6 | 0.3 | 5.8 | 0.3 | 6.7 | 0.3 | 5.8 | 0.3 | 3.1 | 0.3 | 2.8 |
| 0.35 | 5.5 | 0.35 | 7.6 | 0.35 | 5.8 | 0.35 | 6.7 | 0.35 | 5.8 | 0.35 | 3.1 | 0.35 | 2.8 |
| 0.4 | 5.5 | 0.4 | 7.6 | 0.4 | 5.8 | 0.4 | 6.7 | 0.4 | 5.8 | 0.4 | 3.1 | 0.4 | 2.8 |
| 0.45 | 5.5 | 0.45 | 7.6 | 0.45 | 5.8 | 0.45 | 6.7 | 0.45 | 5.8 | 0.45 | 3.1 | 0.45 | 2.8 |
| 0.5 | 5.5 | 0.5 | 7.6 | 0.5 | 5.8 | 0.5 | 6.7 | 0.5 | 5.8 | 0.5 | 3.1 | 0.5 | 2.8 |
| 0.55 | 5.5 | 0.55 | 7.6 | 0.55 | 5.8 | 0.55 | 6.7 | 0.55 | 5.7 | 0.55 | 3.1 | 0.55 | 2.8 |
| 0.6 | 5.5 | 0.6 | 7.6 | 0.6 | 5.8 | 0.6 | 6.7 | 0.6 | 5.6 | 0.6 | 3.1 | 0.6 | 2.8 |
| 0.65 | 5.5 | 0.65 | 7.6 | 0.55 | 5.8 | 0.65 | 6.6 | 0.65 | 5.5 | 0.65 | 3.1 | 0.65 | 2.8 |
| 0.7 | 5.5 | 0.7 | 7.6 | 0.7 | 5.8 | 0.7 | 6.5 | 0.7 | 5.4 | 0.7 | 3.1 | 0.7 | 2.8 |
| 0.75 | 5.3 | 0.75 | 7.4 | 0.75 | 5.8 | 0.75 | 6.3 | 0.75 | 5.1 | 0.75 | 3.1 | 0.75 | 2.8 |
| 0.8 | 5.1 | 0.8 | 7.1 | 0.8 | 5.8 | 0.8 | 6.1 | 0.8 | 4.8 | 0.8 | 2.9 | 0.8 | 2.7 |
| 0.85 | 4.6 | 0.85 | 6.5 | 0.85 | 5.8 | 0.85 | 5.6 | 0.85 | 4.3 | 0.85 | 2.7 | 0.85 | 2.5 |
| 0.9 | 3.9 | 0.9 | 5.5 | 0.9 | 5.0 | 0.9 | 4.7 | 0.9 | 3.6 | 0.9 | 2.4 | 0.9 | 2.2 |
| 0.95 | 2.8 | 0.95 | 3.8 | 0.95 | 3.5 | 0.95 | 3.4 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF-HCFO-1233xf-HFO-1234yf-HCFO-1233zdE-HFO-
1234zeE-HFO-1234zeZ-HFO-1243zf

| Organics 0.15 F1233xf + 0.17 F1234yf + 0.17 F1233zdE + 0.17 F1243zf + 0.17 F1234zeE + 0.17 F1234zeZ | | Organics 0.01 F1233xf + 0.95 F1234yf + 0.01 F1233zdE + 0.01 F1243zf + 0.01 F1234zeE + 0.01 F1234zeZ | | Organics 0.01 F1233xf + 0.01 F1234yf + 0.95 F1233zdE + 0.01 F1243zf + 0.01 F1234zeE + 0.01 F1234zeZ | | Organics 0.01 F1233xf + 0.01 F1234yf + 0.01 F1233zdE + 0.95 F1243zf + 0.01 F1234zeE + 0.01 F1234zeZ | | Organics 0.01 F1233xf + 0.01 F1234yf + 0.01 F1233zdE + 0.01 F1243zf + 0.95 F1234zeE + 0.01 F1234zeZ | | Organics 0.01 F1233xf + 0.01 F1234yf + 0.01 F1233zdE + 0.01 F1243zf + 0.01 F1234zeE + 0.95 F1234zeZ | | Organics 0.95 F1233xf + 0.01 F1234yf + 0.01 F1233zdE + 0.01 F1243zf + 0.01 F1234zeE + 0.01 F1234zeZ | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 3.9 | 0 | 6.6 | 0 | 1.9 | 0 | 5.7 | 0 | 4.8 | 0 | 1.9 | 0 | 1.7 |
| 0.05 | 5.0 | 0.05 | 7.6 | 0.05 | 2.6 | 0.05 | 6.7 | 0.05 | 5.8 | 0.05 | 3.0 | 0.05 | 2.8 |
| 0.1 | 4.9 | 0.1 | 7.6 | 0.1 | 2.6 | 0.1 | 6.7 | 0.1 | 5.8 | 0.1 | 3.0 | 0.1 | 2.8 |
| 0.15 | 4.9 | 0.15 | 7.6 | 0.15 | 2.6 | 0.15 | 6.7 | 0.15 | 5.8 | 0.15 | 3.0 | 0.15 | 2.8 |
| 0.2 | 4.9 | 0.2 | 7.6 | 0.2 | 2.6 | 0.2 | 6.7 | 0.2 | 5.8 | 0.2 | 3.0 | 0.3 | 2.8 |
| 0.25 | 4.9 | 0.25 | 7.6 | 0.25 | 2.6 | 0.25 | 6.7 | 0.25 | 5.8 | 0.25 | 3.0 | 0.25 | 2.8 |
| 0.3 | 4.9 | 0.3 | 7.6 | 0.3 | 2.6 | 0.3 | 6.7 | 0.3 | 5.8 | 0.3 | 3.0 | 0.3 | 2.8 |
| 0.35 | 4.9 | 0.35 | 7.6 | 0.35 | 2.6 | 0.35 | 6.7 | 0.35 | 5.8 | 0.35 | 3.0 | 0.35 | 2.8 |
| 0.4 | 4.9 | 0.4 | 7.6 | 0.4 | 2.6 | 0.4 | 6.7 | 0.4 | 5.8 | 0.4 | 3.0 | 0.4 | 2.8 |
| 0.45 | 4.9 | 0.45 | 7.6 | 0.45 | 2.6 | 0.45 | 6.7 | 0.45 | 5.8 | 0.45 | 3.0 | 0.45 | 2.8 |
| 0.5 | 4.9 | 0.5 | 7.6 | 0.5 | 2.6 | 0.5 | 6.7 | 0.5 | 5.7 | 0.5 | 3.0 | 0.5 | 2.8 |
| 0.55 | 4.9 | 0.55 | 7.6 | 0.55 | 2.6 | 0.55 | 6.7 | 0.55 | 5.7 | 0.55 | 3.0 | 0.55 | 2.8 |
| 0.6 | 4.9 | 0.6 | 7.6 | 0.6 | 2.6 | 0.6 | 6.6 | 0.6 | 5.6 | 0.6 | 3.0 | 0.5 | 2.8 |
| 0.65 | 4.9 | 0.65 | 7.6 | 0.65 | 2.6 | 0.65 | 6.5 | 0.65 | 5.5 | 0.65 | 3.0 | 0.65 | 2.8 |
| 0.7 | 4.8 | 0.7 | 7.6 | 0.7 | 2.6 | 0.7 | 6.5 | 0.7 | 5.3 | 0.7 | 3.0 | 0.7 | 2.8 |
| 0.75 | 4.7 | 0.75 | 7.4 | 0.75 | 2.6 | 0.75 | 6.3 | 0.75 | 5.1 | 0.75 | 3.0 | 0.75 | 2.8 |
| 0.8 | 4.4 | 0.8 | 7.1 | 0.8 | 2.5 | 0.8 | 6.0 | 0.8 | 4.8 | 0.8 | 2.9 | 0.8 | 2.6 |
| 0.85 | 4.0 | 0.85 | 6.5 | 0.85 | 2.3 | 0.85 | 5.5 | 0.85 | 4.3 | 0.85 | 2.7 | 0.85 | 2.5 |
| 0.9 | 3.4 | 0.9 | 5.5 | 0.9 | 2.0 | 0.9 | 4.7 | 0.9 | 3.6 | 0.9 | 2.4 | 0.9 | 2.2 |
| 0.95 | 2.5 | 0.95 | 3.8 | 0.95 | 1.7 | 0.95 | 3.3 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF-HFO-1234yf-HFC-245cb-HCFO-1233zdE-HFO-1234zeE-HFO-1234zeZ-HFO-1243zf

| Organics 0.15 F1234yf + 0.17 F245cb + 0.17 F1233zdE + 0.17 F1234zeE + 0.17 F1234zeZ + 0.17 F1243zf | | Organics 0.95 F1234yf + 0.01 F245cb + 0.01 F1233zdE + 0.01 F1234zeE + 0.01 F1234zeZ + 0.01 F1243zf | | Organics 0.01 F1234yf + 0.95 F245cb + 0.01 F1233zdE + 0.01 F1234zeE + 0.01 F1234zeZ + 0.01 F1243zf | | Organics 0.01 F1234yf + 0.01 F245cb + 0.95 F1233zdE + 0.01 F1234zeE + 0.01 F1234zeZ + 0.01 F1243zf | | Organics 0.01 F1234yf + 0.01 F245cb + 0.01 F1233zdE + 0.95 F1234zeE + 0.01 F1234zeZ + 0.01 F1243zf | | Organics 0.01 F1234yf + 0.01 F245cb + 0.01 F1233zdE + 0.01 F1234zeE + 0.01 F1234zeZ + 0.95 F1243zf | | Organics 0.01 F1234yf + 0.01 F245cb + 0.01 F1233zdE + 0.01 F1234zeE + 0.95 F1234zeZ + 0.01 F1243zf | |
|---|---|---|---|---|---|---|---|---|---|---|---|---|---|
| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
| 0 | 4.3 | 0 | 6.6 | 0 | 4.6 | 0 | 1.5 | 0 | 4.8 | 0 | 5.8 | 0 | 2.0 |
| 0.05 | 5.3 | 0.05 | 7.6 | 0.05 | 5.8 | 0.05 | 2.6 | 0.05 | 5.8 | 0.05 | 6.7 | 0.05 | 3.1 |
| 0.1 | 5.3 | 0.1 | 7.6 | 0.1 | 5.8 | 0.1 | 2.6 | 0.1 | 5.8 | 0.1 | 6.7 | 0.1 | 3.1 |
| 0.15 | 5.3 | 0.15 | 7.6 | 0.15 | 5.8 | 0.15 | 2.6 | 0.15 | 5.8 | 0.15 | 6.7 | 0.15 | 3.1 |
| 0.2 | 5.3 | 0.2 | 7.6 | 0.2 | 5.8 | 0.2 | 2.6 | 0.2 | 5.8 | 0.2 | 6.7 | 0.2 | 3.1 |
| 0.25 | 5.3 | 0.25 | 7.6 | 0.25 | 5.8 | 0.25 | 2.6 | 0.25 | 5.8 | 0.25 | 6.7 | 0.25 | 3.1 |
| 0.3 | 5.3 | 0.3 | 7.6 | 0.3 | 5.8 | 0.3 | 2.6 | 0.3 | 5.8 | 0.3 | 6.7 | 0.3 | 3.1 |
| 0.35 | 5.3 | 0.35 | 7.6 | 0.35 | 5.8 | 0.35 | 2.6 | 0.35 | 5.8 | 0.35 | 6.7 | 0.35 | 3.1 |
| 0.4 | 5.3 | 0.4 | 7.6 | 0.4 | 5.8 | 0.4 | 2.6 | 0.4 | 5.8 | 0.4 | 6.7 | 0.4 | 3.1 |
| 0.45 | 5.3 | 0.45 | 7.6 | 0.45 | 5.8 | 0.45 | 2.6 | 0.45 | 5.8 | 0.45 | 6.7 | 0.45 | 3.1 |
| 0.5 | 5.3 | 0.5 | 7.6 | 0.5 | 5.8 | 0.5 | 2.6 | 0.5 | 5.8 | 0.5 | 6.7 | 0.5 | 3.1 |
| 0.55 | 5.3 | 0.55 | 7.6 | 0.55 | 5.8 | 0.55 | 2.6 | 0.55 | 5.7 | 0.55 | 6.7 | 0.55 | 3.1 |
| 0.6 | 5.3 | 0.6 | 7.6 | 0.6 | 5.8 | 0.6 | 2.6 | 0.6 | 5.6 | 0.6 | 6.7 | 0.5 | 3.1 |
| 0.65 | 5.3 | 0.65 | 7.6 | 0.65 | 5.8 | 0.65 | 2.6 | 0.65 | 5.5 | 0.65 | 6.6 | 0.65 | 3.1 |
| 0.7 | 5.3 | 0.7 | 7.6 | 0.7 | 5.8 | 0.7 | 2.6 | 0.7 | 5.4 | 0.7 | 6.5 | 0.7 | 3.1 |
| 0.75 | 5.2 | 0.75 | 7.4 | 0.75 | 5.8 | 0.75 | 2.6 | 0.75 | 5.1 | 0.75 | 6.3 | 0.75 | 3.1 |
| 0.8 | 4.9 | 0.8 | 7.1 | 0.8 | 5.8 | 0.8 | 2.5 | 0.8 | 4.3 | 0.8 | 6.1 | 0.8 | 2.9 |
| 0.85 | 4.5 | 0.85 | 6.5 | 0.85 | 5.8 | 0.85 | 2.3 | 0.85 | 4.3 | 0.85 | 5.6 | 0.85 | 2.7 |
| 0.9 | 3.9 | 0.9 | 5.5 | 0.9 | 5.0 | 0.9 | 2.1 | 0.9 | 3.6 | 0.9 | 4.7 | 0.9 | 2.4 |
| 0.95 | 2.8 | 0.95 | 3.8 | 0.95 | 3.5 | 0.95 | 1.7 | 0.95 | 2.6 | 0.95 | 3.4 | 0.95 | 1.9 |
| 1 | 1.2 | 1 | 1.2 | 1 | 1.2 | 1 | 1.2 | 1 | 1.2 | 1 | 1.2 | 1 | 1.2 |

HF-HFF-1243zf-HCFC-244bb-HFC-245fa-Trifluoropropyne-HFO-1225yeZ-HFO-1225zc

| MASS-FRAC HF | Organics 0.15 F1243zf + 0.17 F244bb + 0.17 F245fa + 0.17 TFP + 0.17 F1225yeZ + 0.17 F1225zc TOTAL PRESSURE bar | Organics 0.95 F1243zf + 0.01 F244bb + 0.01 F245fa + 0.01 TFP + 0.01 F1225yeZ + 0.01 F1225zc TOTAL PRESSURE bar | Organics 0.01 F1243zf + 0.95 F244bb + 0.01 F245fa + 0.01 TFP + 0.01 F1225yeZ + 0.01 F1225zc TOTAL PRESSURE bar | Organics 0.01 F1243zf + 0.01 F244bb + 0.95 F245fa + 0.01 TFP + 0.01 F1225yeZ + 0.01 F1225zc TOTAL PRESSURE bar | Organics 0.01 F1243zf + 0.01 F244bb + 0.01 F245fa + 0.95 TFP + 0.01 F1225yeZ + 0.01 F1225zc TOTAL PRESSURE bar | Organics 0.01 F1243zf + 0.01 F244bb + 0.01 F245fa + 0.01 TFP + 0.95 F1225yeZ + 0.01 F1225zc TOTAL PRESSURE bar | Organics 0.01 F1243zf + 0.01 F244bb + 0.01 F245fa + 0.01 TFP + 0.01 F1225yeZ + 0.95 F1225zc TOTAL PRESSURE bar |
|---|---|---|---|---|---|---|---|
| 0 | 5.5 | 5.8 | 1.0 | 1.8 | 11.3 | 5.2 | 5.3 |
| 0.05 | 6.5 | 6.8 | 2.1 | 2.9 | 12.1 | 6.2 | 6.3 |
| 0.1 | 6.5 | 6.8 | 2.1 | 2.9 | 12.0 | 6.2 | 6.3 |
| 0.15 | 6.4 | 6.8 | 2.1 | 2.9 | 11.9 | 6.2 | 6.3 |
| 0.2 | 6.4 | 6.8 | 2.1 | 2.9 | 11.8 | 6.2 | 6.3 |
| 0.25 | 6.4 | 6.8 | 2.1 | 2.9 | 11.7 | 6.2 | 6.3 |
| 0.3 | 6.4 | 6.8 | 2.1 | 2.9 | 11.6 | 6.2 | 6.3 |
| 0.35 | 6.4 | 6.8 | 2.1 | 2.9 | 11.5 | 6.2 | 6.3 |
| 0.4 | 6.4 | 6.8 | 2.1 | 2.9 | 11.5 | 6.2 | 6.3 |
| 0.45 | 6.4 | 6.8 | 2.1 | 2.9 | 11.5 | 6.2 | 6.3 |
| 0.5 | 6.3 | 6.7 | 2.1 | 2.9 | 11.5 | 6.2 | 6.3 |
| 0.55 | 6.3 | 6.7 | 2.1 | 2.9 | 11.5 | 6.2 | 6.2 |
| 0.6 | 6.3 | 6.7 | 2.1 | 2.9 | 11.6 | 6.2 | 6.1 |
| 0.65 | 6.2 | 6.6 | 2.1 | 2.9 | 11.6 | 6.2 | 6.0 |
| 0.7 | 6.2 | 6.6 | 2.1 | 2.9 | 11.7 | 6.1 | 5.9 |
| 0.75 | 6.0 | 6.4 | 2.0 | 2.8 | 11.6 | 5.9 | 5.6 |
| 0.8 | 5.7 | 6.1 | 2.0 | 2.8 | 11.3 | 5.6 | 5.2 |
| 0.85 | 5.2 | 5.6 | 2.0 | 2.6 | 10.5 | 5.1 | 4.7 |
| 0.9 | 4.4 | 4.8 | 1.9 | 2.3 | 8.9 | 4.2 | 3.9 |
| 0.95 | 3.1 | 3.4 | 1.6 | 1.6 | 6.0 | 3.0 | 2.7 |
| 1 | 1.2 | 1.2 | 1.2 | 1.2 | 1.2 | 1.2 | 1.2 |

EXAMPLE 14: TEMPERATURE AND PRESSURE RANGE OF SYSTEM WITH 7 COMPOUNDS

| | Boiling point range | |
|---|---|---|
| System with 7 compounds | Temperature ° C. | Pressure bar abs |
| HC-HCFO-1233xf-HFO-1234yf-HFC-245cb-HCFO-1233zdE-HFO-1234zeE-HFO-1243zf | 0 to 40 | ~1.0 to ~11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HFC-245cb-HFO-1234zeE-HFO-1234zeZ-HFO-1243zf | 0 to 40 | ~1.1 to ~11.6 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HCFO-1233xf-HFC-245cb-HCFO-1233zdE-HFO-1234zeE-HFO-1234zeZ-HFO-1243zf | 0 to 40 | ~0.9 to ~10.3 |
| HF-HFO-1234yf-HFC-245b-HCFO-1233zdE-HFO-1234zeE-HFO-1234zeZ-HFO-1243zf | 0 to 40 | ~1.0 to ~11.6 |
| HF-HFF-1243zf-HCFC-244bb-HFC-245fa-Trifluoropropyne-HFO-1225yeZ-HFO-1225zc | 0 to 40 | ~0.7 to ~17.5 |

EXAMPLE 15: DECANTATION RANGE OF SYSTEMS WITH 7 COMPOUNDS

| | Decantation ranges Mass percentage of HF Temperature | | |
|---|---|---|---|
| System with 7 compounds | 0° C. | 25° C. | 40° C. |
| HC-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeE-HFO-1243zf | 5-70 | 5-70 | 10-60 |
| HF-HCFO-1233xf-HFO-1234yf-HFC-245cb-HFO-1234zeE-HFO-1234zeZ-HFO-1243zf | 5-75 | 10-65 | * |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HCFO-1233xf-HFC-245cb-HCFO-1233zdE-HFO-1234zeE-HFO-1234zeZ-HFO-1243zf | 5-75 | 5-70 | 10-55 |
| HF-HFO-1234yf-HFC-245b-HCFO-1233zdE-HFO-1234zeE-HFO-1234zeZ-HFO-1243zf | 5-75 | 10-65 | * |
| HF-HFF-1243zf-HCFC-244bb-HFC-245fa-Trifluoropropyne-HFO-1225yeZ-HFO-1225zc | 5-75 | 10-70 | * |

EXAMPLE 16: SYSTEMS WITH 8 COMPOUNDS

HF-HCFO-1233xf-HFO-1234yf-HFC-245cb-HCFO-1233zdE-HFO-1234zeE-HFO-1234zeZ-HFO-1243zf

| Organics | Organics | Organics | Organics | Organics | Organics | Organics |
|---|---|---|---|---|---|---|
| 0.01 F1233xf + 0.94 F1234yf + 0.01 F245cb + 0.01 F1233zdE + 0.01 F1234zeE + 0.01 F1234zeZ + 0.01 F1243zf | 0.01 F1233xf + 0.01 F1234yf + 0.94 F245cb + 0.01 F1233zdE + 0.01 F1234zeE + 0.01 F1234zeZ + 0.01 F1243zf | 0.01 F1233xf + 0.01 F1234yf + 0.01 F245cb + 0.94 F1233zdE + 0.01 F1234zeE + 0.01 F1234zeZ + 0.01 F1243zf | 0.01 F1233xf + 0.01 F1234yf + 0.01 F245cb + 0.01 F1233zdE + 0.94 F1234zeE + 0.01 F1234zeZ + 0.01 F1243zf | 0.01 F1233xf + 0.01 F1234yf + 0.01 F245cb + 0.01 F1233zdE + 0.01 F1234zeE + 0.94 F1234zeZ + 0.01 F1243zf | 0.01 F1233xf + 0.01 F1234yf + 0.01 F245cb + 0.01 F1233zdE + 0.01 F1234zeE + 0.01 F1234zeZ + 0.94 F1243zf | 0.16 F1233xf + 0.14 F1234yf + 0.14 F245cb + 0.14 F1233zdE + 0.14 F1234zeE + 0.14 F1234zeZ + 0.14 F1243zf |

| MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar | MASS-FRAC HF | TOTAL PRESSURE bar |
|---|---|---|---|---|---|---|---|---|---|---|---|---|---|
| 0 | 6 | 0 | 4.6 | 0 | 1.5 | 0 | 4.8 | 0 | 2.0 | 0 | 5.7 | 0 | 3.9 |
| 0.05 | 7.6 | 0.05 | 5.8 | 0.05 | 2.6 | 0.05 | 5.8 | 0.05 | 3.1 | 0.05 | 6.7 | 0.05 | 5.0 |
| 0.1 | 7.6 | 0.1 | 5.8 | 0.1 | 2.6 | 0.1 | 5.8 | 0.1 | 3.1 | 0.1 | 6.7 | 0.1 | 5.0 |
| 0.15 | 7.6 | 0.15 | 5.8 | 0.15 | 2.6 | 0.15 | 5.8 | 0.15 | 3.1 | 0.15 | 6.7 | 0.15 | 5.0 |
| 0.2 | 7.6 | 0.2 | 5.8 | 0.2 | 2.6 | 0.2 | 5.8 | 0.2 | 3.1 | 0.2 | 6.7 | 0.2 | 5.0 |
| 0.25 | 7.6 | 0.25 | 5.8 | 0.25 | 2.6 | 0.25 | 5.8 | 0.25 | 3.1 | 0.25 | 6.7 | 0.25 | 5.0 |
| 0.3 | 7.6 | 0.3 | 5.8 | 0.3 | 2.6 | 0.3 | 5.8 | 0.3 | 3.1 | 0.3 | 6.7 | 0.3 | 5.0 |
| 0.35 | 7.6 | 0.35 | 5.8 | 0.35 | 2.6 | 0.35 | 5.8 | 0.35 | 3.1 | 0.35 | 6.7 | 0.35 | 5.0 |
| 0.4 | 7.6 | 0.4 | 5.8 | 0.4 | 2.6 | 0.4 | 5.8 | 0.4 | 3.1 | 0.4 | 6.7 | 0.4 | 5.0 |
| 0.45 | 7.6 | 0.45 | 5.8 | 0.45 | 2.6 | 0.45 | 5.8 | 0.45 | 3.1 | 0.45 | 6.7 | 0.45 | 5.0 |
| 0.5 | 7.6 | 0.5 | 5.8 | 0.5 | 2.6 | 0.5 | 5.7 | 0.5 | 3.1 | 0.5 | 6.7 | 0.5 | 5.0 |
| 0.55 | 7.6 | 0.55 | 5.8 | 0.55 | 2.6 | 0.55 | 5.7 | 0.55 | 3.1 | 0.55 | 6.7 | 0.55 | 5.0 |
| 0.6 | 7.6 | 0.6 | 5.8 | 0.6 | 2.6 | 0.6 | 5.6 | 0.6 | 3.1 | 0.6 | 6.6 | 0.6 | 5.0 |
| 0.65 | 7.6 | 0.65 | 5.8 | 0.65 | 2.6 | 0.65 | 5.5 | 0.65 | 3.1 | 0.65 | 6.6 | 0.65 | 5.0 |
| 0.7 | 7.5 | 0.7 | 5.8 | 0.7 | 2.6 | 0.7 | 5.4 | 0.7 | 3.1 | 0.7 | 6.5 | 0.7 | 5.0 |
| 0.75 | 7.4 | 0.75 | 5.8 | 0.75 | 2.6 | 0.75 | 5.1 | 0.75 | 3.1 | 0.75 | 6.3 | 0.75 | 4.9 |
| 0.8 | 7.1 | 0.8 | 5.8 | 0.8 | 2.5 | 0.8 | 4.8 | 0.8 | 2.9 | 0.8 | 6.0 | 0.8 | 4.6 |
| 0.85 | 6.5 | 0.85 | 5.8 | 0.85 | 2.3 | 0.85 | 4.3 | 0.85 | 2.7 | 0.85 | 5.5 | 0.85 | 4.2 |
| 0.9 | 5.5 | 0.9 | 5.0 | 0.9 | 2.1 | 0.9 | 3.6 | 0.9 | 2.4 | 0.9 | 4.7 | 0.9 | 3.9 |
| 0.95 | 3.0 | 0.95 | 3.5 | 0.95 | 1.7 | 0.95 | 2.6 | 0.95 | 1.9 | 0.95 | 3.3 | 0.95 | 2.6 |
| 1 | 1.2 | 1 | 1.2 | 1 | 1.2 | 1 | 1.2 | 1 | 1.2 | 1 | 1.2 | 1 | 1.2 |

EXAMPLE 17: TEMPERATURE AND PRESSURE RANGE OF SYSTEM WITH 8 COMPOUNDS

| System with 8 compounds | Boiling point range | |
|---|---|---|
| | Temperature °C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ~1.0 to ~11.5 |

EXAMPLE 18: DECANTATION RANGES OF SYSTEM WITH 8 COMPOUNDS

| System with 8 compounds | Decantation ranges Mass percentage of HF Temperature | | |
|---|---|---|---|
| | 0° C. | 25° C. | 40° C. |
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |

EXAMPLE 19: SYSTEMS WITH 13 COMPOUNDS

HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc

| MASSFRAC HF | Organics 0.087 012346F + 0.087 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.88 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
|---|---|---|---|---|---|
| 0 | 4.5 | 6.5 | 1.0 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.8 | 4.3 | 2.5 |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

EXAMPLE 20: TEMPERATURE AND
PRESSURE RANGE OF SYSTEM WITH 13
COMPOUNDS

| | Boiling point range | |
|---|---|---|
| System with 13 compounds | Temperature ° C. | Pressure bar abs |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 0 to 40 | ~0.7 to ~18.0 |

EXAMPLE 21: DECANTATION RANGES OF
SYSTEM WITH 13 COMPOUNDS

| | Decantation ranges Mass percentage of HF Temperature | | |
|---|---|---|---|
| System with 13 compounds | 0° C. | 25° C. | 40° C. |
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 5-75% | 10-70% | 15-60% |

The invention claimed is:

1. An azeotropic or quasi-azeotropic composition comprising hydrogen fluoride, 3,3,3-trifluoropropene, and one or more compounds selected from the group consisting of 1,1,1,2,2-pentafluoropropane, 2,3,3,3-tetrafluoropropene, E-3,3,3-trifluoro-1-chloropropene, 3,3,3-trifluoro-2-chloropropene, and 1,3,3,3-tetrafluoropropene, in which the boiling point of said composition is between −20° C. and 80° C. and at a pressure of between 0.1 and 44 bar absolute.

2. An azeotropic or quasi-azeotropic composition comprising hydrogen fluoride, 3,3,3-trifluoropropene, and one or more compounds selected from the group consisting of 1,1,1,2,2-pentafluoropropane, 2,3,3,3-tetrafluoropropene, 1,3,3,3-tetrafluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane, in which the boiling point of said composition is between −20° C. and 80° C. and at a pressure of between 0.1 and 44 bar absolute.

3. The composition as claimed in claim 1, in which the composition comprises hydrogen fluoride, 3,3,3-trifluoropropene and at least one or more organic compounds chosen from E-1,3,3,3-tetrafluoropropene, Z-1,3,3,3-tetrafluoropropene, 3,3,3-trifluoro-2-chloropropene, E-3,3,3-trifluoro-1-chloropropene, 1,1,1,2,2-pentafluoropropane and 2,3,3,3-tetrafluoropropene.

4. The composition as claimed in claim 1, in which the composition is heteroazeotropic or quasi-heteroazeotropic.

5. The composition as claimed in claim 1, in which the composition comprises hydrogen fluoride, 3,3,3-trifluoropropene, E-1,3,3,3-tetrafluoropropene and optionally one or more organic compounds chosen from Z-1,3,3,3-tetrafluoropropene, 3,3,3-trifluoro-2-chloropropene, E-3,3,3-trifluoro-1-chloropropene, 1,1,1,2,2-pentafluoropropane and 2,3,3,3-tetrafluoropropene.

6. The composition as claimed in claim 1, in which the composition comprises hydrogen fluoride, 3,3,3-trifluoropropene, Z-1,3,3,3-tetrafluoropropene and optionally one or more organic compounds chosen from 3,3,3-trifluoro-2-chloropropene, E-3,3,3-trifluoro-1-chloropropene, 1,1,1,2,2-pentafluoropropane and 2,3,3,3-tetrafluoropropene.

7. The composition as claimed in claim 1, in which the composition comprises hydrogen fluoride, 3,3,3-trifluoropropene, 3,3,3-trifluoro-2-chloropropene and optionally one or more organic compounds chosen from E-3,3,3-trifluoro-1-chloropropene, 1,1,1,2,2-pentafluoropropane and 2,3,3,3-tetrafluoropropene.

8. The composition as claimed in claim 1, in which the composition comprises hydrogen fluoride, 3,3,3-trifluoropropene, E-3,3,3-trifluoro-1-chloropropene and optionally one or more organic compounds chosen from 1,1,1,2,2-pentafluoropropane and 2,3,3,3-tetrafluoropropene.

9. The composition as claimed in claim 1, in which the composition comprises hydrogen fluoride, 3,3,3-trifluoropropene, 1,1,1,2,2-pentafluoropropane and optionally 2,3,3,3-tetrafluoropropene.

10. The composition as claimed in claim 1, in which the composition comprises hydrogen fluoride, 3,3,3-trifluoropropene and 2,3,3,3-tetrafluoropropene.

11. The composition as claimed in claim 1, in which the composition comprises from 1% to 85% by weight of hydrogen fluoride and from 99% to 15% by weight of the sum of the organic compounds.

12. The composition as claimed in claim 1, in which the composition comprises from 5% to 80% by weight of hydrogen fluoride and from 95% to 20% by weight of the sum of the organic compounds.

13. The composition as claimed in claim 1, in which the boiling point of said composition is between 0° C. and 40° C. and at a pressure of between 0.7 and 18 bar absolute.

14. The composition as claimed in claim 1, in which the boiling point of said composition is between 0° C. and 40° C. and at a pressure of between 0.9 and 12.5 bar absolute.

15. The composition as claimed in claim 1, comprising two or more compounds selected from the group consisting of 1,1,1,2,2-pentafluoropropane, 2,3,3,3-tetrafluoropropene, E-3,3,3-trifluoro-1-chloropropene, 3,3,3-trifluoro-2-chloropropene, and 1,3,3,3-tetrafluoropropene.

16. An azeotropic or quasi-azeotropic composition comprising hydrogen fluoride, 3,3,3-trifluoropropene and three or more compounds selected from the group consisting of 1,1,1,2,2-pentafluoropropane, 2,3,3,3-tetrafluoropropene, E-3,3,3-trifluoro-1-chloropropene, 3,3,3-trifluoro-2-chloropropene, and 1,3,3,3-tetrafluoropropene.

* * * * *